(12) United States Patent
Kim et al.

(10) Patent No.: US 11,359,229 B2
(45) Date of Patent: Jun. 14, 2022

(54) MOLECULAR VERIFICATION SYSTEMS

(71) Applicant: President and Fellows of Harvard College, Cambridge, MA (US)

(72) Inventors: Jongmin Kim, Cambridge, MA (US); Jocelyn Yoshiko Kishi, Cambridge, MA (US); Peng Yin, Cambridge, MA (US); Steven Henry Strassmann, Cambridge, MA (US); Thomas E. Schaus, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 475 days.

(21) Appl. No.: 16/334,643

(22) PCT Filed: Sep. 19, 2017

(86) PCT No.: PCT/US2017/052234
§ 371 (c)(1),
(2) Date: Mar. 19, 2019

(87) PCT Pub. No.: WO2018/057502
PCT Pub. Date: Mar. 29, 2018

(65) Prior Publication Data
US 2021/0277452 A1 Sep. 9, 2021

Related U.S. Application Data

(60) Provisional application No. 62/502,522, filed on May 5, 2017, provisional application No. 62/407,331, filed on Oct. 12, 2016, provisional application No. 62/396,932, filed on Sep. 20, 2016.

(51) Int. Cl.
*C12Q 1/68* (2018.01)
*C12Q 1/6818* (2018.01)
*G06Q 30/00* (2012.01)

(52) U.S. Cl.
CPC ......... *C12Q 1/6818* (2013.01); *G06Q 30/018* (2013.01)

(58) Field of Classification Search
CPC .. C12Q 1/6813; C12Q 1/6834; C12Q 1/6818; G06Q 30/018
See application file for complete search history.

(56) References Cited

U.S. PATENT DOCUMENTS

| | | |
|---|---|---|
| 5,543,507 A | 8/1996 | Cook et al. |
| 9,273,349 B2 | 3/2016 | Nguyen et al. |
| 9,284,602 B2 | 3/2016 | Zhang et al. |
| 10,024,796 B2 | 7/2018 | Lin et al. |
| 10,036,059 B2 | 7/2018 | Zhang et al. |
| 2002/0065609 A1 | 5/2002 | Ashby |
| 2004/0166520 A1 | 8/2004 | Connolly |
| 2005/0045063 A1 | 3/2005 | Niggemann et al. |
| 2005/0112610 A1 | 5/2005 | Lee et al. |
| 2006/0063196 A1 | 3/2006 | Akeson et al. |
| 2006/0286569 A1 | 12/2006 | Bar-Or et al. |
| 2006/0286570 A1 | 12/2006 | Rowlen et al. |
| 2007/0031829 A1 | 2/2007 | Yasuno et al. |
| 2007/0042419 A1 | 2/2007 | Barany et al. |
| 2007/0048761 A1 | 3/2007 | Reep et al. |
| 2008/0299559 A1 | 12/2008 | Kwok et al. |
| 2009/0042191 A1 | 2/2009 | Hayward et al. |
| 2011/0129834 A1 | 6/2011 | Chen et al. |
| 2011/0300640 A1 | 12/2011 | Josten et al. |
| 2012/0014977 A1 | 1/2012 | Furihata et al. |
| 2012/0021410 A1 | 1/2012 | Yin et al. |
| 2012/0165219 A1 | 6/2012 | van der Zaag et al. |
| 2012/0231972 A1 | 9/2012 | Golyshin et al. |
| 2012/0253689 A1 | 10/2012 | Rogan |
| 2013/0072390 A1 | 3/2013 | Wang et al. |
| 2013/0225623 A1 | 8/2013 | Buxbaum et al. |
| 2013/0244894 A1 | 9/2013 | Mercolino |
| 2013/0261019 A1 | 10/2013 | Lin et al. |
| 2014/0081665 A1 | 3/2014 | Holmes et al. |
| 2014/0087377 A1 | 3/2014 | Park et al. |
| 2014/0141984 A1 | 5/2014 | Swartz et al. |
| 2014/0255921 A1 | 9/2014 | Moysey et al. |
| 2014/0349288 A1 | 11/2014 | Church et al. |
| 2015/0107475 A1* | 4/2015 | Jung ............... B42D 25/378 101/483 |
| 2015/0111780 A1 | 4/2015 | Mercolino |
| 2016/0024558 A1 | 1/2016 | Hardenbol et al. |
| 2016/0312272 A1 | 10/2016 | Barish et al. |
| 2017/0327888 A1 | 11/2017 | Ong et al. |
| 2018/0010174 A1 | 1/2018 | Schaus et al. |
| 2019/0106733 A1 | 4/2019 | Kishi et al. |

(Continued)

FOREIGN PATENT DOCUMENTS

| | | |
|---|---|---|
| CN | 1836050 A | 9/2006 |
| CN | 101541975 A | 9/2009 |
| WO | WO 01/94625 A2 | 12/2001 |

(Continued)

OTHER PUBLICATIONS

Extended European Search Report dated May 27, 2020, for Application No. 17853744.5.

(Continued)

*Primary Examiner* — Jezia Riley
(74) *Attorney, Agent, or Firm* — Wolf, Greenfield & Sacks, P.C.

(57) ABSTRACT

Provided herein are molecular verification (authentication) systems, methods and compositions that use molecular (DNA/RNA) circuitry to enable specific molecularly encrypted solutions.

23 Claims, 29 Drawing Sheets

Specification includes a Sequence Listing.

(56) References Cited

U.S. PATENT DOCUMENTS

2021/0019973 A1 1/2021 Yin et al.

FOREIGN PATENT DOCUMENTS

| WO | WO 2004/046321 A2 | 6/2004 |
|----|----|----|
| WO | WO 2007/002016 A2 | 1/2007 |
| WO | WO 2007/117256 A1 | 10/2007 |
| WO | WO 2010/107416 A1 | 9/2010 |
| WO | WO 2011/156434 A2 | 12/2011 |
| WO | WO 2012/058638 A2 | 3/2012 |
| WO | WO 2012/058488 A1 | 5/2012 |
| WO | WO 2012/071428 A2 | 5/2012 |
| WO | WO 2012/112804 A1 | 8/2012 |
| WO | WO 2013/012434 A1 | 1/2013 |
| WO | WO 2013/140107 A1 | 9/2013 |
| WO | WO 2013/188912 A1 | 12/2013 |
| WO | WO 2014/071361 A1 | 5/2014 |
| WO | WO 2014/074648 A2 | 5/2014 |
| WO | WO 2014/130388 A1 | 8/2014 |
| WO | WO 2014/135838 A1 | 9/2014 |
| WO | WO 2014/164958 A1 | 10/2014 |
| WO | WO 2015/095633 A1 | 6/2015 |
| WO | WO 2015/178978 A2 | 11/2015 |
| WO | WO 2016/011089 A1 | 1/2016 |
| WO | WO 2016/032562 A1 | 3/2016 |
| WO | WO 2016/123419 A1 | 8/2016 |
| WO | WO 2017/143006 A1 | 8/2017 |
| WO | WO 2019/183359 A1 | 9/2019 |

OTHER PUBLICATIONS

[No Author Listed], New COVID-19 Variants. Centers for Disease Control and Prevention. Updated Jan. 15, 2021. 3 pages.

Baccouche et al., Dynamic DNA-toolbox reaction circuits: a walk-through. Methods. May 15, 2014;67(2):234-49. doi: 10.1016/j.ymeth.2014.01.015. Epub Feb. 2, 2014.

Forster et al., A human gut bacterial genome and culture collection for improved metagenomic analyses. Nat Biotechnol. 2019;37(2):186?192. doi:10.1038/s41587-018-0009-7.

Montagne et al., Programming an in vitro DNA oscillator using a molecular networking strategy. Mol Syst Biol. Feb. 1, 2011;7:466. doi: 10.1038/msb.2010.120. Erratum in: Mol Syst Biol. Mar. 8, 2011;7:476. Mol Syst Biol. 2011;7. doi:10.1038/msb.2011.12.

Sah et al., Complete Genome Sequence of a 2019 Novel Coronavirus (SARS-CoV-2) Strain Isolated in Nepal. Microbiol Resour Announc. Mar. 12, 2020;9(11):e00169-20. doi: 10.1128/MRA.00169-20.

Zeberg et al., The major genetic risk factor for severe COVID-19 is inherited from Neanderthals. Nature. Nov. 2020;587(7835):610-612. doi: 10.1038/s41586-020-2818-3. Epub Sep. 30, 2020.

Zhu et al., Toehold-mediated strand displacement reaction triggered isothermal DNA amplification for highly sensitive and selective fluorescent detection of single-base mutation. Biosens Bioelectron. Sep. 15, 2014;59:276-81. doi: 10.1016/j.bios.2014.03.051. Epub Apr. 1, 2014.

Beliveau et al., Versatile design and synthesis platform for visualizing genomes with Oligopaint FISH probes. Proc Natl Acad Sci U S A. Dec. 26, 2012;109(52):21301-6. doi:10.1073/pnas.1213818110. Epub Dec. 11, 2012.

Dreyfus et al., A Supply chain management perspective on mitigating the risks of counterfeit products. Michigan State University. Oct. 2013. https://globaledge.msu.edu/Content/Uploads/Supply-Chain-Bgrounder_V8_FINAL_.pdf.

Jungmann et al., Nanoscale imaging in DNA nanotechnology. Wiley Interdiscip Rev Nanomed Nanobiotechnol. Jan.-Feb. 2012;4(1):66-81. doi:10.1002/wnan.173. Epub Nov. 23, 2011.

Li et al., Multiplexed detection of pathogen DNA with DNA-based fluorescence nanobarcodes. Nat Biotechnol. Jul. 2005;23(7):885-9. Epub Jun. 12, 2005.

Yin et al., Programming biomolecular self-assembly pathways. Nature. Jan. 17, 2008;451(7176):318-22. doi:10.1038/nature06451.

Zhang et al., Control of DNA strand displacement kinetics using toehold exchange. J Am Chem Soc. Dec. 2, 2009;131(47):17303-14. doi: 10.1021/ja906987s.

Chen et al., Conditionally fluorescent molecular probes for detecting single base changes in double-stranded DNA. Nat Chem. 2013;5(9):782-9. Author Manuscript, 16 pages.

Fredriksson et al., Protein detection using proximity-dependent DNA ligation assays. Nat Biotechnol. May 2002;20(5):473-7.

Green et al., Toehold switches: de-novo-designed regulators of gene expression. Cell. Nov. 6, 2014;159(4):925-39. doi: 10.1016/j.cell.2014.10.002. Epub Oct. 23, 2014. Author Manuscript, 28 pages.

Jungmann et al., Single-molecule kinetics and super-resolution microscopy by fluorescence imaging of transient binding on DNA origami. Nano Lett. Nov. 10, 2010;10(11):4756-61.

Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014.

Pardee et al., Paper-based synthetic gene networks. Cell. Nov. 6, 2014;159(4):940-54. doi: 10.1016/j.cell.2014.10.004. Epub Oct. 23, 2014. Author Manuscript, 28 pages.

Schaus et al, A DNA nanoscope via auto-cycling proximity recording. Nat Commun. Sep. 25, 2017;8(1):696(1-9).

Tribioli et al., Long-term room temperature storage of high-quality embryonic stem cell genomic DNA extracted with a simple and rapid procedure. J Biomol Tech. Sep. 2006;17(4):249-51.

Yan et al., Isothermal amplified detection of DNA and RNA. Mol Biosyst. May 2014;10(5):970-1003. doi: 10.1039/c3mb70304e.

Zhang et al., Optimizing the specificity of nucleic acid hybridization. Nat Chem. Epub Jan. 22, 2012, 7 pages.

Zhang et al., Dynamic DNA nanotechnology using strand-displacement reactions. Nat Chem. 2011;3(2):103-13.

Extended European Search Report dated Nov. 18, 2021 for Application No. EP 19771822.4.

Fujimo et al., Quick, selective and reversible photocrosslinking reaction between 5-methylcytosine and 3-cyanovinylcarbazole in DNA double strand. Int J Mol Sci. Mar. 12, 2013;14(3):5765-74.

Kishi et al., Programmable autonomous synthesis of single-stranded DNA. Nat Chem. Feb. 2018;10(2):155-164. Epub Nov. 6, 2017.

* cited by examiner

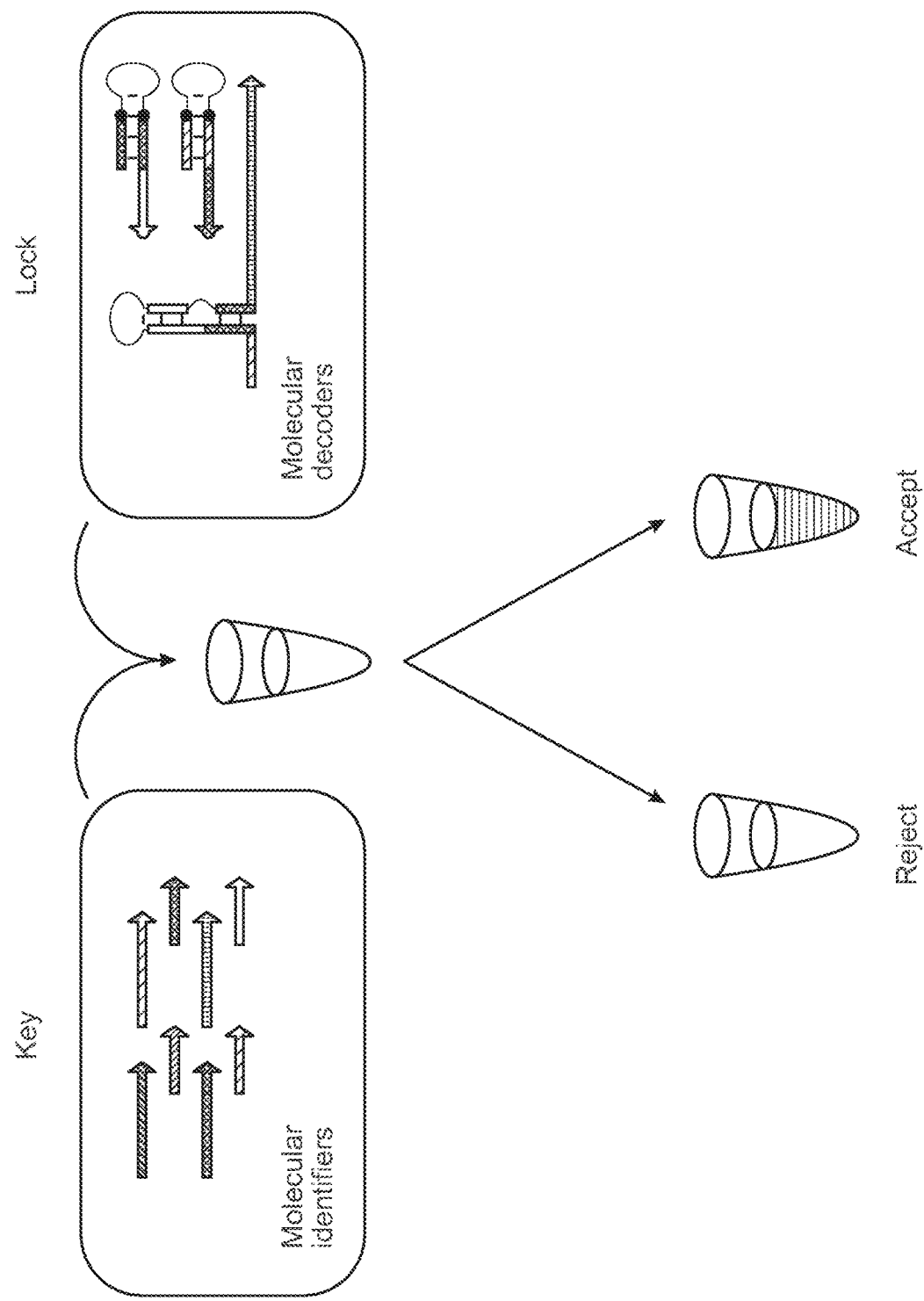

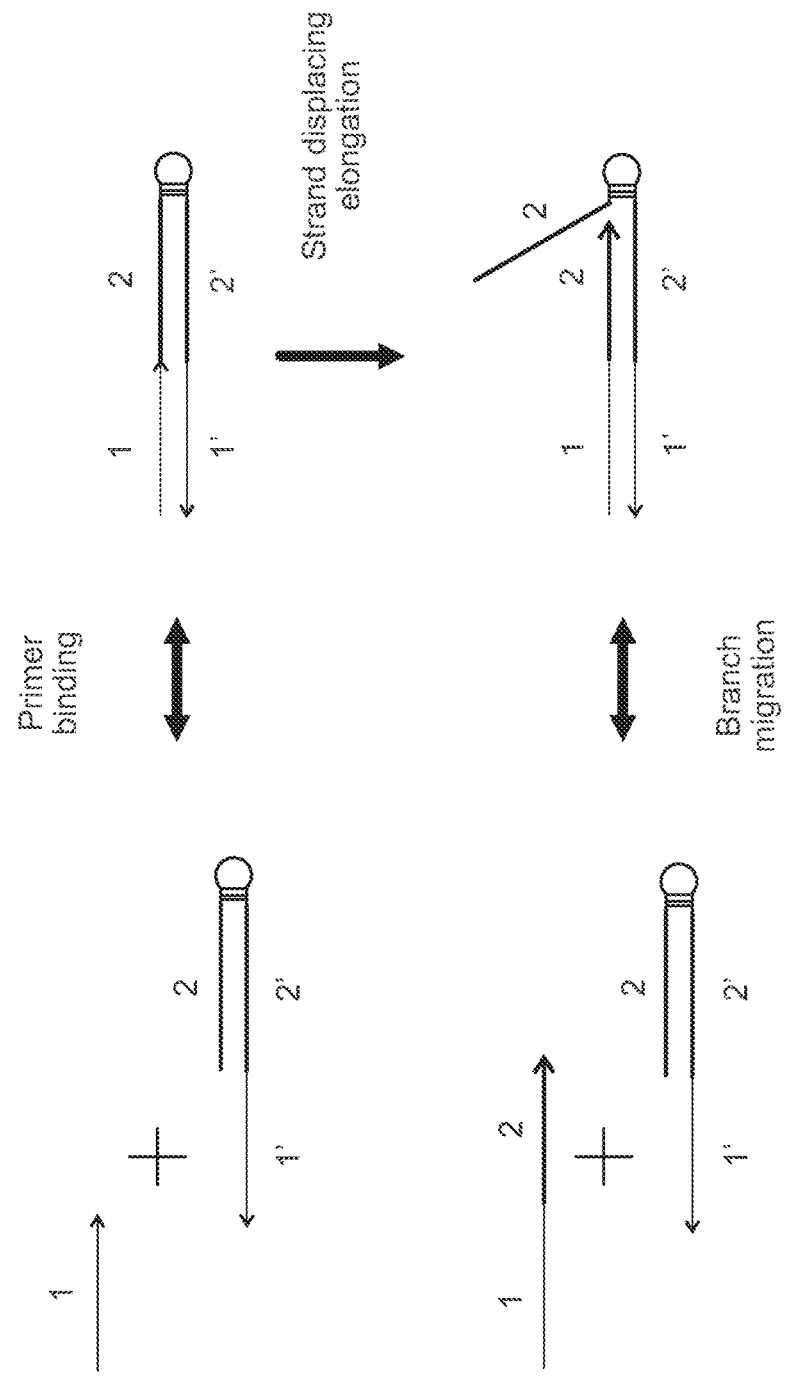

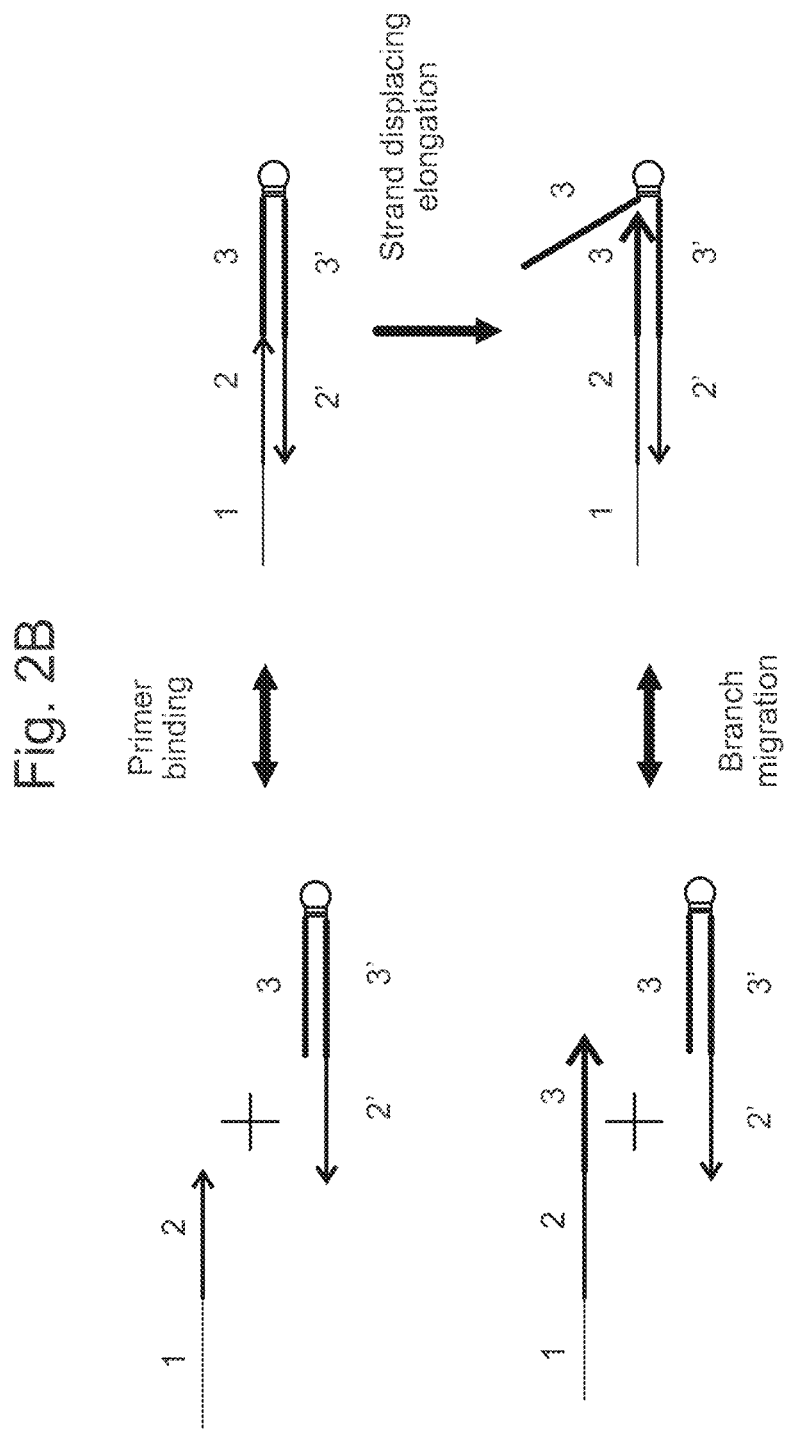

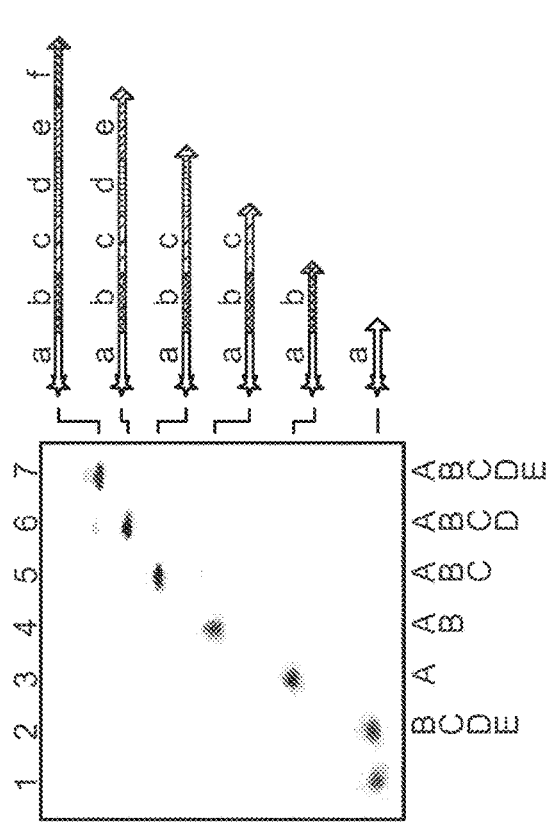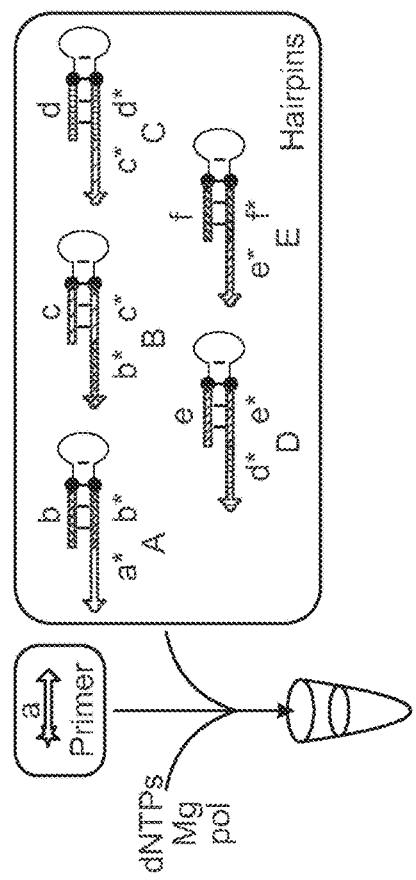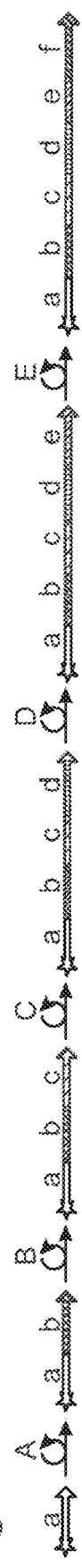
Fig. 3A
Fig. 3C
Fig. 3B

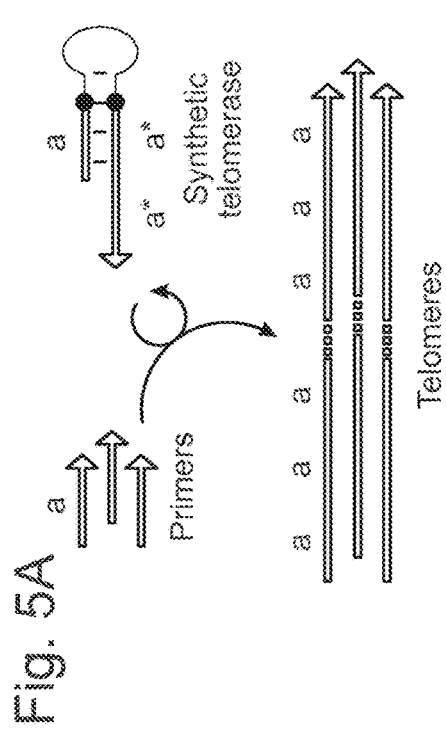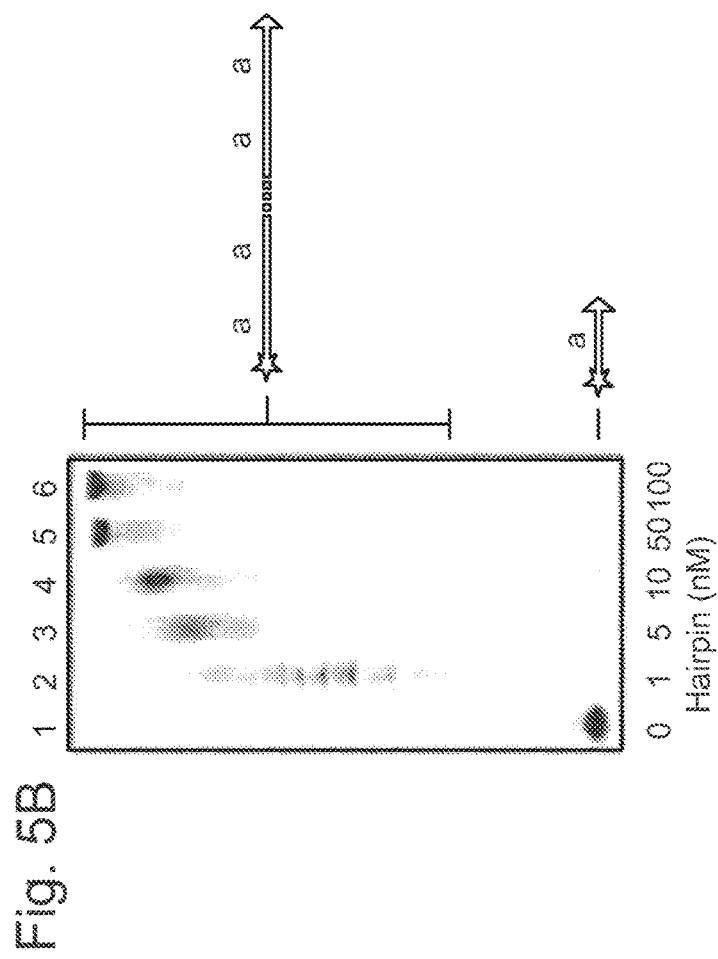

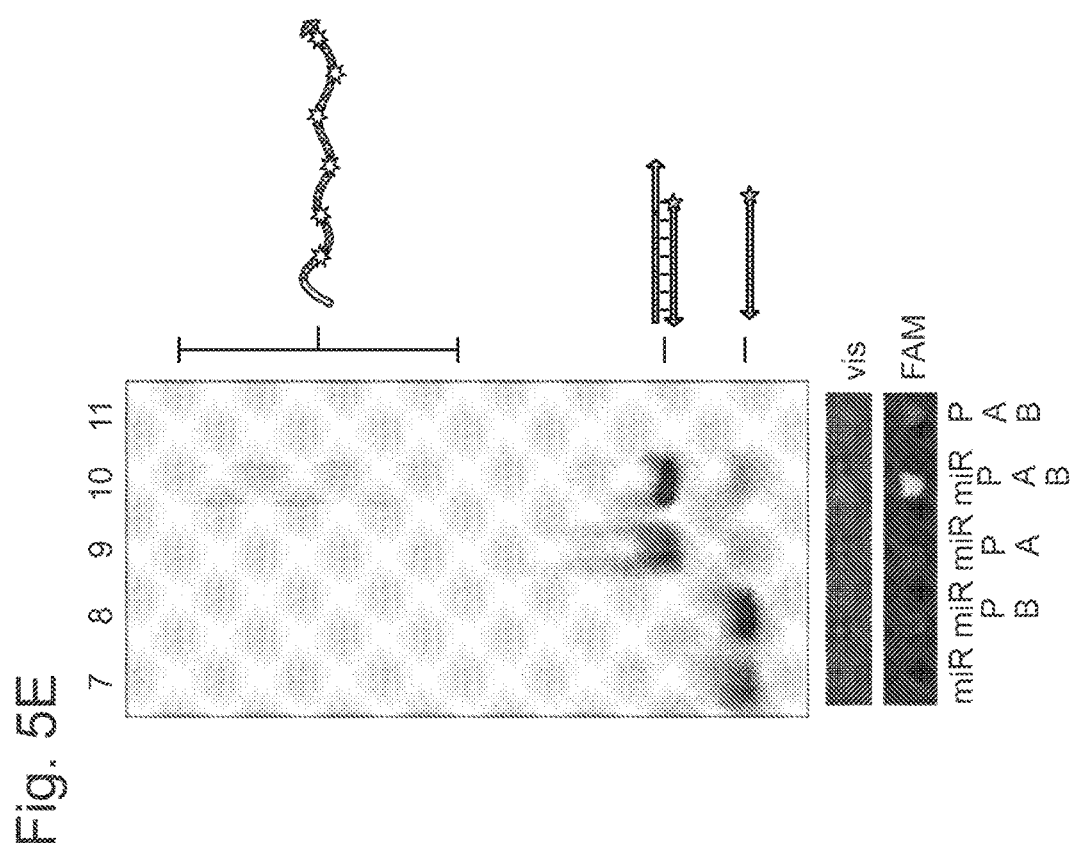

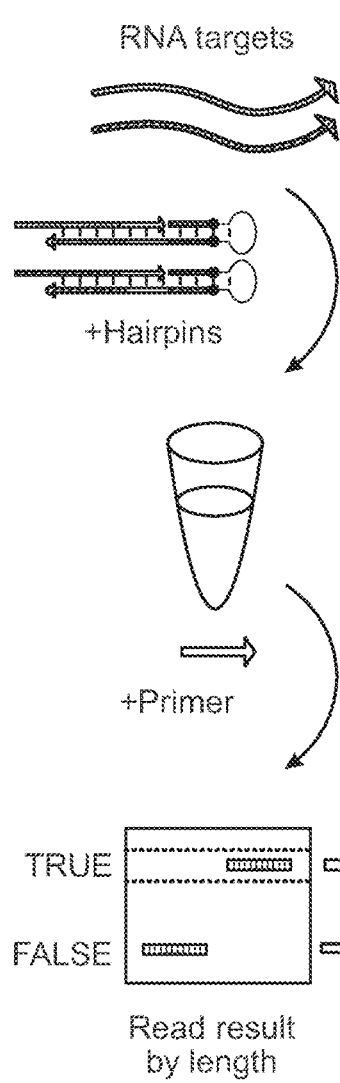
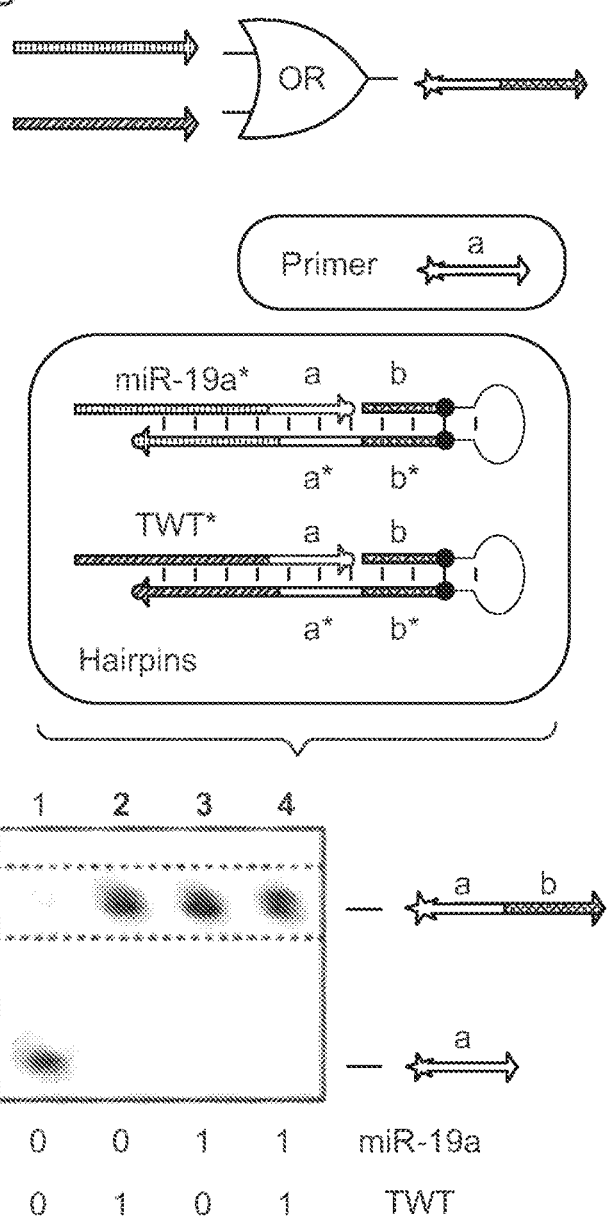

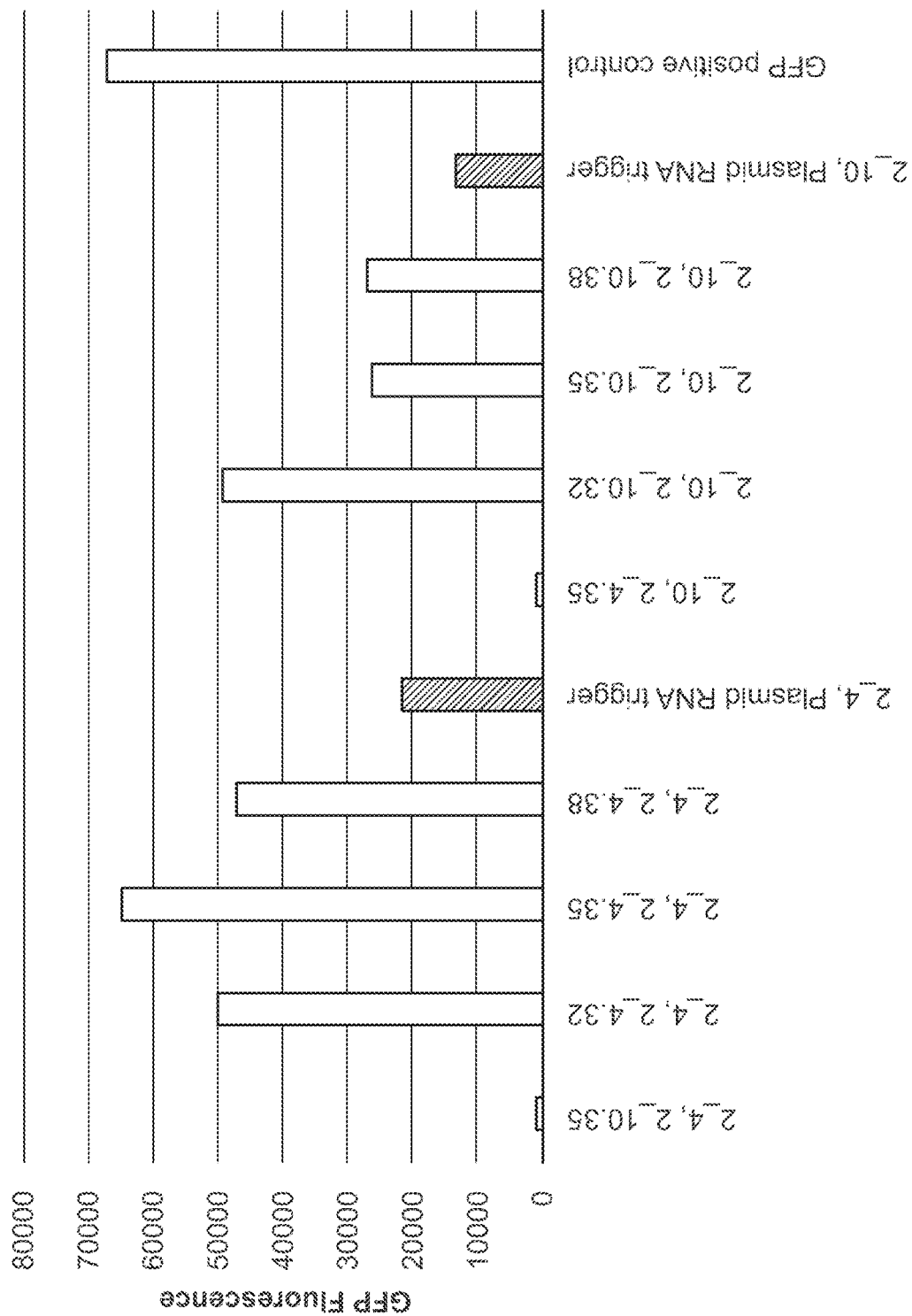

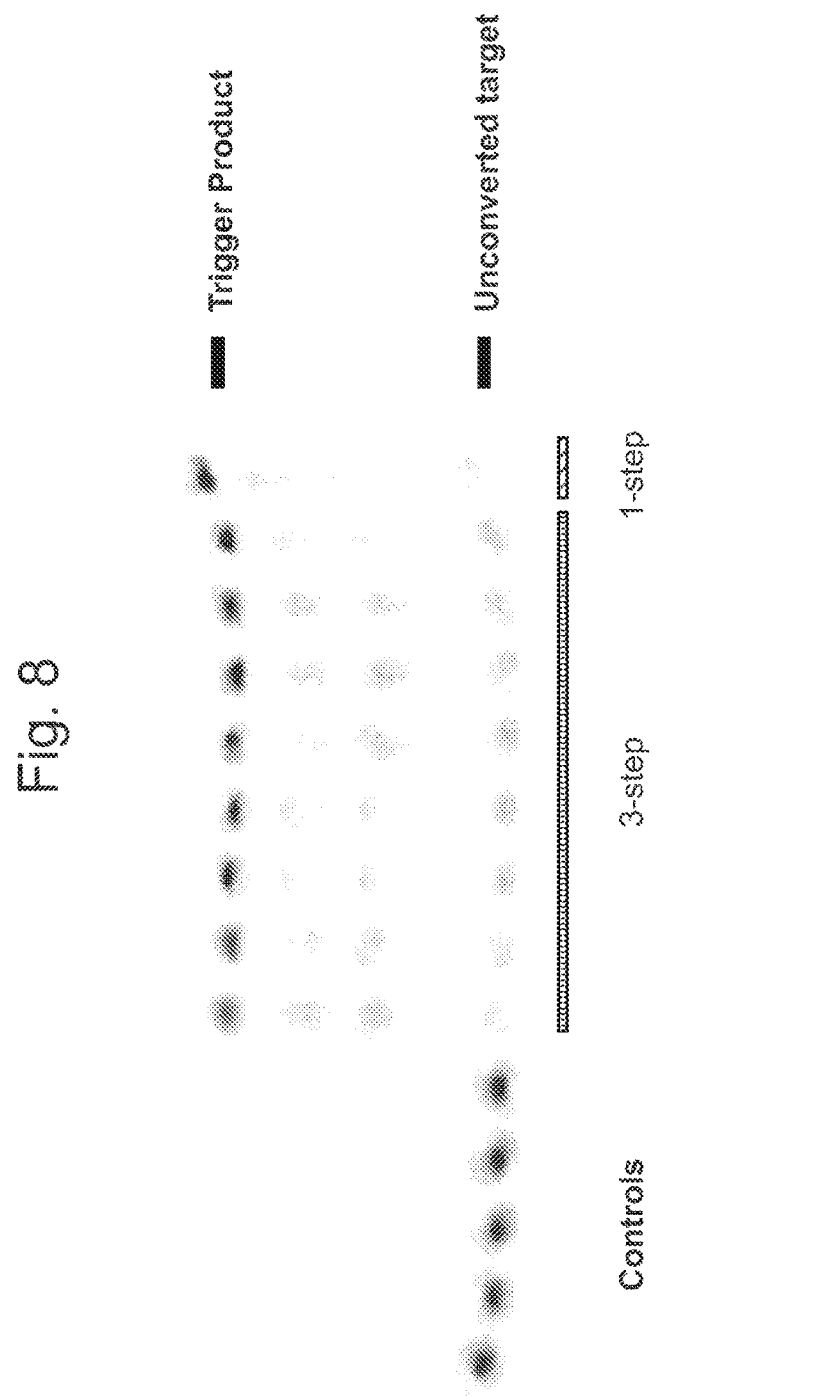

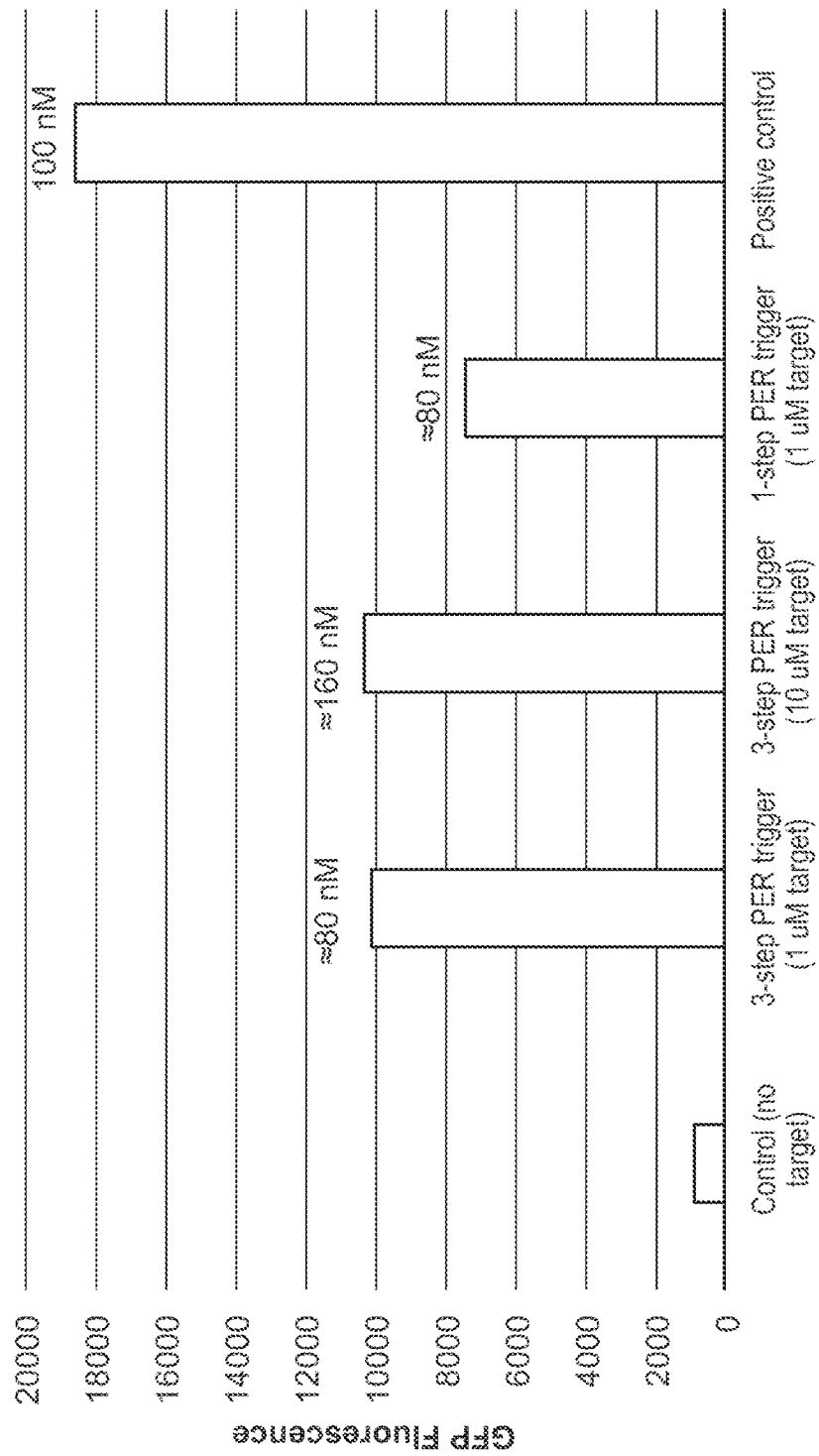

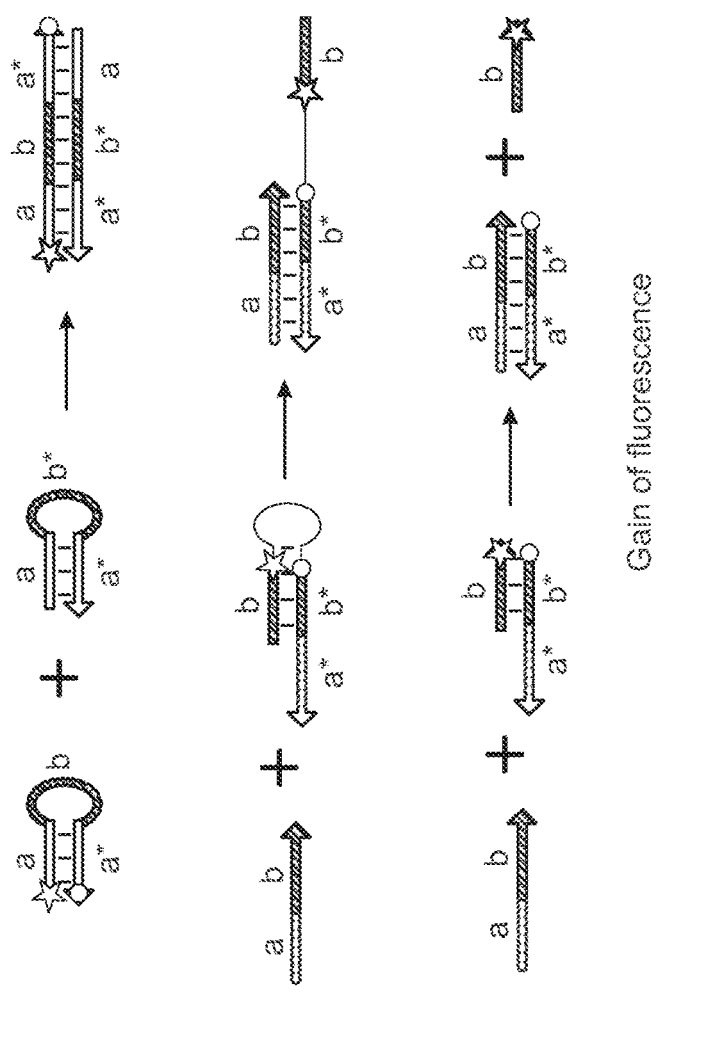
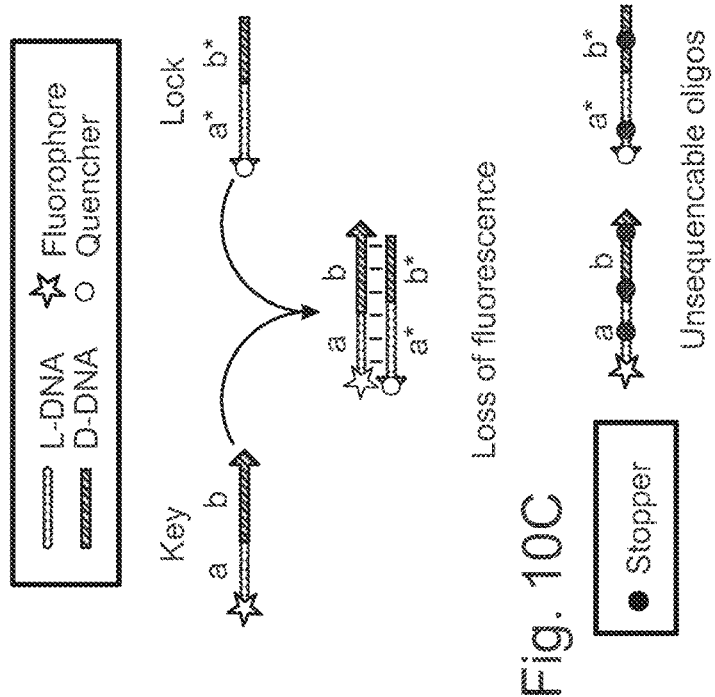
Fig. 10A  Fig. 10B  Fig. 10C

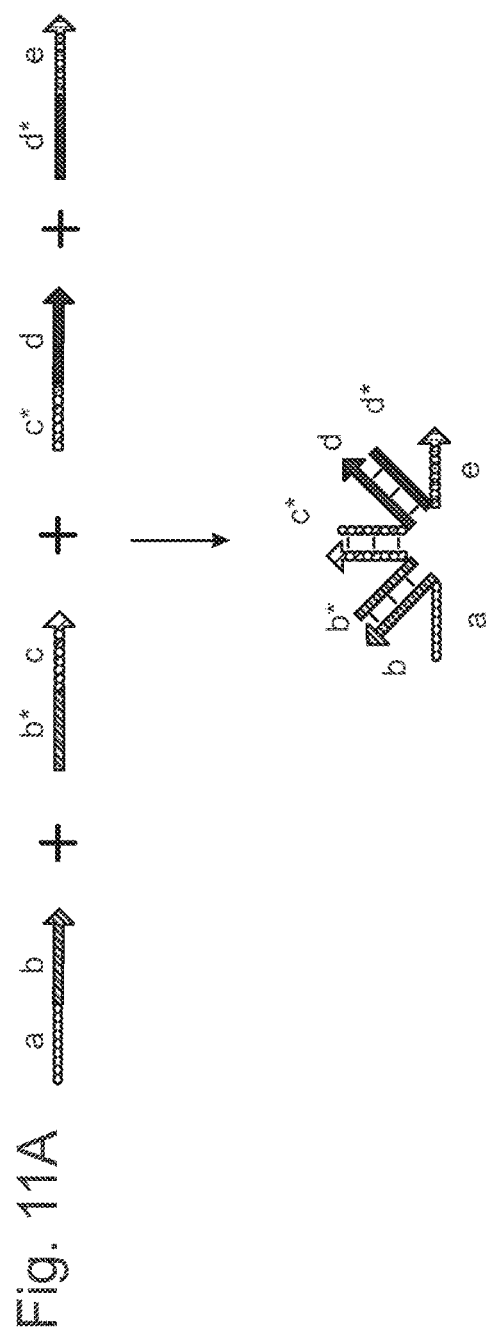
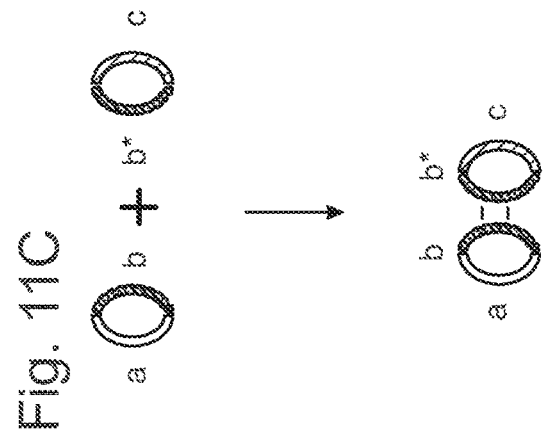
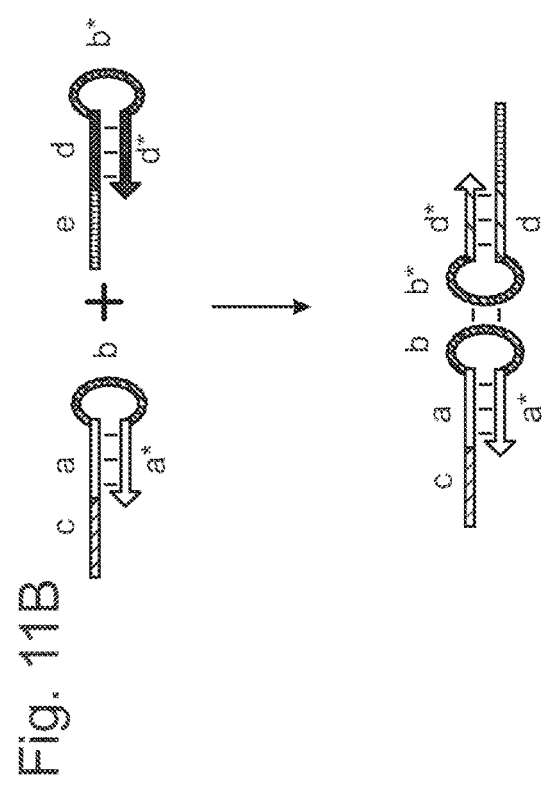
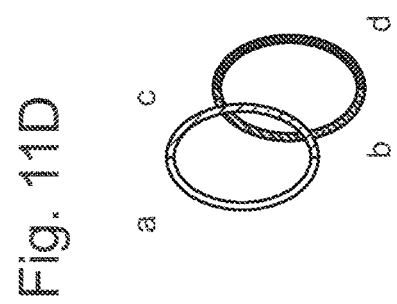
Fig. 11A
Fig. 11B
Fig. 11C
Fig. 11D

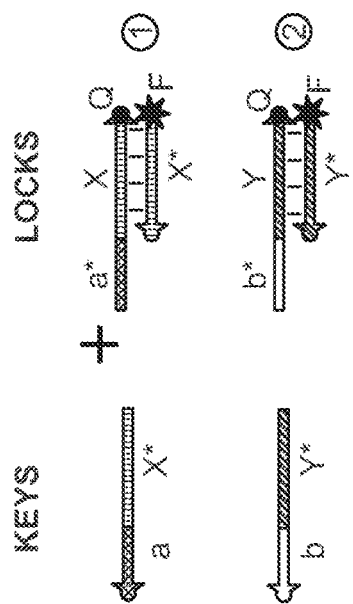
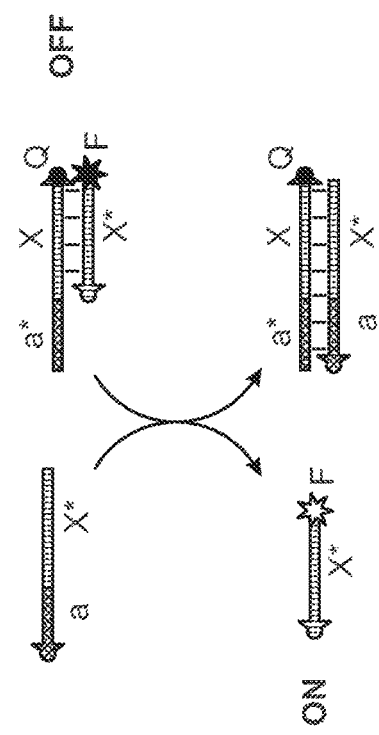
Figs. 12A
Figs. 12B

Fig. 14B After spray results:

Accept

FAKE

FAKE

SEQUENCE LISTING

```
<160> NUMBER OF SEQ ID NOS: 17

<210> SEQ ID NO 1
<211> LENGTH: 108
<212> TYPE: DNA
<213> ORGANISM: Artificial Sequence
<220> FEATURE:
<223> OTHER INFORMATION: Synthetic polynucleotide

<400> SEQUENCE: 1
gcgctaatac gactcactat agggagtaag ataatgaagg taggtatgtt aaactttaga      60
acagaggaga taaagatgaa catacctacg aacctggcgg cagcgcaa                  108

<210> SEQ ID NO 2
<211> LENGTH: 108
<212> TYPE: DNA
<213> ORGANISM: Artificial Sequence
<220> FEATURE:
<223> OTHER INFORMATION: Synthetic polynucleotide

<400> SEQUENCE: 2
gcgctaatac gactcactat agggattgaa tatgatagaa gtttagtagt agacaataga      60
acagaggaga tattgatgac tactaaacta aacctggcgg cagcgcaa                  108

<210> SEQ ID NO 3
<211> LENGTH: 97
<212> TYPE: DNA
<213> ORGANISM: Artificial Sequence
<220> FEATURE:
<223> OTHER INFORMATION: Synthetic polynucleotide

<400> SEQUENCE: 3
gcgctaatac gactcactat agggctcgat cactaatctg atcgagacga acatacctac      60
cttcattatc ttacttgtta gcataacccc ttggggc                               97

<210> SEQ ID NO 4
<211> LENGTH: 97
<212> TYPE: DNA
<213> ORGANISM: Artificial Sequence
<220> FEATURE:
<223> OTHER INFORMATION: Synthetic polynucleotide

<400> SEQUENCE: 4
gcgctaatac gactcactat agggatacac atagaatcat gtgtataaca ctactaaact      60
tctatcatat tcaatcacta gcataacccc ttggggc                               97

<210> SEQ ID NO 5
```

```
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 5
acgaacatac ctaccttcat tatcttactt gt                                    32

<210> SEQ ID NO 6
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 6
acgaacatac ctaccttcat tatcttactc cccac                                 35

<210> SEQ ID NO 7
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 7
acatttaaca tacctacctt cattatctta ctccccac                              38

<210> SEQ ID NO 8
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 8
aacactacta aacttctatc atattcaatc ac                                    32

<210> SEQ ID NO 9
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 9
aacactacta aacttctatc atattcaatc cccac                                 35

<210> SEQ ID NO 10
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 10
aactctacta ctaaacttct atcatattca atccccac                              38

<210> SEQ ID NO 11
<211> LENGTH: 43
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
```

```
<222> LOCATION: (43)..(43)
<223> OTHER INFORMATION: 3' inverted dT

<400> SEQUENCE: 11
acctaccttc gggccttttg gcccgaaggt aggtatgttc gtt                43

<210> SEQ ID NO 12
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (40)..(40)
<223> OTHER INFORMATION: 3' inverted dT

<400> SEQUENCE: 12
attatcttgg gccttttggc ccaagataat gaaggtaggt                   40

<210> SEQ ID NO 13
<211> LENGTH: 43
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: 3' inverted dT

<400> SEQUENCE: 13
actccccacg ggccttttgg cccgtgggga gtaagataat gat                43

<210> SEQ ID NO 14
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (42)..(42)
<223> OTHER INFORMATION: 3' inverted dT

<400> SEQUENCE: 14
acctaccttc gggccttttg gcccgaaggt aggtatgttc gt                 42

<210> SEQ ID NO 15
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(39)
<223> OTHER INFORMATION: 3' inverted dT

<400> SEQUENCE: 15
attatcttgg gccttttggc ccaagataat gaaggtagt                    39

<210> SEQ ID NO 16
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
```

```
<221> NAME/KEY: misc_feature
<222> LOCATION: (42)..(42)
<223> OTHER INFORMATION: 3' inverted dT

<400> SEQUENCE: 16
actccccacg ggccttttgg cccgtgggga gtaagataat gt              42

<210> SEQ ID NO 17
<211> LENGTH: 77
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (77)..(77)
<223> OTHER INFORMATION: 3' inverted dT

<400> SEQUENCE: 17
acctaccttc attatcttac tccccacggg ccttttggcc cgtggggagt aagataatga   60
aggtaggtat gttcgtt                                                  77
```

MOLECULAR VERIFICATION SYSTEMS

RELATED APPLICATIONS

This application is a national stage filing under 35 U.S.C. § 371 of international application number PCT/US2017/052234, filed Sep. 19, 2017, which was published under PCT Article 21(2) in English and claims the benefit under U.S.C. § 119(e) of U.S. provisional application No. 62/396,932, filed Sep. 20, 2016, U.S. provisional application No. 62/407,331, filed Oct. 12, 2016, and U.S. provisional application No. 62/502,522, filed May 5, 2017, each of which is incorporated by reference herein in its entirety.

FEDERALLY SPONSORED RESEARCH

This invention was made with government support under N00014-16-1-2410, N00014-14-1-0610 and N00014-13-1-0593 awarded by U.S. Department of Defense, Office of Naval Research. The government has certain rights in the invention.

BACKGROUND

Increasingly sophisticated security measures are being used to limit access to sensitive information, applications, and venues. For example, many software platforms now use two-step verification to ensure only the proper individuals have access to the system. In addition to having a password, a person must simultaneously provide a secondary form of evidence that he or she should have access to the system, such as by entering a one-time password (OTP) sent to their phone.

Biometric analyses as a method of securely identifying an individual's identity have also come to the forefront with the advent of fingerprint scanners in devices, such as smartphones, or at the entry into venues, such as amusement parks. Other types of biometric analyses look at an individual's characteristics such as eyes, hands, or faces. Many of these methods, however, can be easily fooled. For example, a high resolution photograph of a hand can reveal the features necessary to mimic fingerprints and thus gain access to otherwise secure information. Some of these current methods may also be considered invasive, and easily compromised to reveal sensitive personal information.

SUMMARY

Provided herein are molecular verification (authentication) systems, methods and compositions that use molecular (DNA/RNA) circuitry to enable specific molecularly encrypted solutions. Molecular identifiers ('keys') used in conjunction with molecular decoders ('locks') serve as a system of molecular encryption to uniquely identify particular entities (e.g., a person or product) in possession of the correct key solution (see, e.g., FIG. 1). Unlike current verification systems, the molecular verification systems of the present disclosure do not require the use of personal biometric features, and thus eliminate the sensitive and sometimes invasive nature of biometric analysis and storage. Yet, the molecular verification systems provided herein maintain the powerful capability of robustly and uniquely detecting specific molecular characteristics.

Although current biometric analyses can be quite powerful in their ability to distinguish between the statistics of individuals, they also have several functional disadvantages. One disadvantage is that biometric analyses must be tailored to every individual, thus even if the verification procedure is intended to apply to a large group of people (e.g., a commercial, governmental or academic organization), it must be adapted to fit each individual and is, therefore, difficult to disperse effectively. Another disadvantage is that biometric analyses typically require a database and server to verify individual biometrics, thus offering another security vulnerability. Yet another disadvantage is that these biometric analyses tend to store indefinitely sensitive, personal information. The molecular verification systems as provided herein enable identity verification without the storage and retrieval vulnerabilities of current security measures.

Thus, the present disclosure provides systems and methods for using a set of oligonucleotides and an associated molecular verification solution as a key and lock system for robust and secure identification. Digital hardware and software are unnecessary, which further reduces the potential for the security of a system to be compromised. Further, in many cases, the reactants can be dried for convenient, long term storage and transportation before verification is performed.

The verification/authentication systems of the present disclosure generally include key component(s) and lock component(s). It should be understood that in any of the embodiments herein, the key component(s) may be applied to or associated with a product, while the lock component(s) is maintained in a solution that is combined with or added to the product. Likewise, in any of the embodiments herein, the lock component(s) may be applied to or associated with a product, while the key component(s) is maintained in a solution that is combined with or added to the product.

Some aspects of the present disclosure provide kits or compositions, comprising (a) a composition comprising a set of catalytic molecules, each catalytic hairpin molecule comprising (i) an unpaired 3' toehold domain, (ii) a paired stem domain formed by intramolecular nucleotide base pairing between a 3' subdomain of the molecule and a 5' subdomain of the molecule, and optionally (iii) a loop domain, (b) a composition comprising a primer key that is complementary to and binds to the 3' toehold domain of one of the catalytic molecules, (c) a composition comprising a RNA toehold switch lock comprising (i) an unpaired toehold domain that comprises a sequence complementary to the 3' subdomain of one of the catalytic molecules, (ii) a hairpin comprising a paired stem domain comprising an initiation codon located 3' of the unpaired toehold domain and a sequence complementary to the 3' toehold domain of one of the catalytic molecules, and a loop domain comprising a ribosome binding site, and (iii) a coding domain encoding a reporter protein.

Other aspects of the present disclosure provide methods comprising: combining in a first reaction buffer comprising a polymerase having strand displacement activity, and deoxyribonucleotide triphosphates (dNTPs) (a) a set of catalytic molecules, each catalytic hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a loop domain, and (b) a primer key that is complementary to and binds to the 3' toehold domain of one of the catalytic molecules; incubating the first reaction mixture under conditions that result in nucleic acid polymerization, strand displacement and annealing, for a time sufficient to produce a single-stranded nucleic acid trigger; combining in a second reaction buffer (c) the single-stranded nucleic acid trigger, and (d) a RNA toehold switch lock comprising (i) an unpaired toehold domain that comprises a sequence complementary to the 3' subdomain of one of the catalytic molecules, (ii) a hairpin comprising a paired stem domain comprising an initiation codon located 3' of the unpaired toehold domain and a sequence complementary to the 3' toehold domain of one of the catalytic molecules, and a loop domain comprising a ribosome binding site, and (iii) a coding domain encoding a reporter protein, thereby forming a second reaction mixture; and incubating the second reaction mixture under conditions that result in nucleic acid hybridization, RNA transcription and protein translation, for a time sufficient to express the reporter protein.

Yet other aspects of the present disclosure provide kits or compositions comprising (a) a composition comprising a nucleic acid strand linked to a fluorescent molecule and having a 5' domain and a 3' domain, and (b) a composition comprising a nucleic acid strand linked to a quenching molecule and having (i) a 5' domain complementary to the 3' domain of the nucleic acid strand of (a) and (ii) a 3' domain complementary to the 5' domain of the nucleic acid strand of (a).

Still other aspects of the present disclosure provide kits or compositions comprising (a) a composition comprising a nucleic acid hairpin molecule having a loop domain and a stem domain formed by pairing of a 5' end domain and a 3' end domain, wherein one end domain includes a fluorescent molecule and the other end includes a quenching molecule; and (b) a composition comprising a nucleic acid hairpin molecule having a loop domain and a stem domain formed by pairing of a 5' end domain and a 3' end domain, wherein one end domain comprises a sequence complementary to a sequence of the 5' end domain of the hairpin molecule of (a), the other end domain comprises a sequence complementary to a sequence of the 3' end domain of the hairpin molecule of (a), and the loop domain comprises a sequence complementary to a sequence of the loop domain of (a).

Some aspects of the present disclosure provide kits or compositions comprising (a) a composition comprising a catalytic molecule having (i) an unpaired toehold domain, (ii) a paired stem domain comprising a fluorescent molecule opposing a quenching molecule, and optionally (iii) a loop domain, and (b) a composition comprising a nucleic acid strand having two adjacent domains, one domain complementary to the toehold domain of the catalytic molecule of (a) and the other domain complementary to the stem domain of the catalytic molecule of (a).

In some embodiments, provided herein are methods comprising combining in a reaction buffer comprising the composition of (a) and the composition (b), and incubating the reaction buffer under conditions that result in nucleic acid hybridization.

Another aspect of the present disclosure provides kits comprising (a) a first nucleic acid strand comprising a 5' domain and a 3' domain; (b) a second nucleic acid strand comprising a 5' domain that is complementary to the 3' domain of the first nucleic acid strand; (c) a third nucleic acid strand comprising (i) a 5' domain that is complementary to the 3' domain of the first nucleic acid strand and (ii) a 3' domain that is complementary to the 5' domain of the first nucleic acid strand; (d) a fourth nucleic acid strand comprising a 5' domain and a 3' domain; (e) a fifth nucleic acid strand comprising a 5' domain that is complementary to the 3' domain of the fourth nucleic acid strand; (f) a sixth nucleic acid strand comprising (i) a 5' domain that is complementary to the 3' domain of the fourth nucleic acid strand and (ii) a 3' domain that is complementary to the 5' domain of the fourth nucleic acid strand; (g) quencher molecules; and (h) fluorescent molecules, wherein the 3' domain of the first nucleic acid strand and the 3' domain of the fourth nucleic acid strand have nucleotide compositions that are different from each other.

In some embodiments, at least one of the quencher molecules is linked to the 3' domain of the first nucleic acid strand and/or is linked to the 3' domain of the fourth nucleic acid strand. In some embodiments, the fluorescent molecule is linked to the 5' domain of the second nucleic acid strand and/or is linked to the 5' domain of the fifth nucleic acid strand. In some embodiments, a first solution comprises the first nucleic acid strand bound to the second nucleic acid strand is present. In some embodiments, a second solution comprises the fourth nucleic acid strand bound to the fifth nucleic acid strand is present.

Still other aspects of the present disclosure provide solutions comprising (a) a first nucleic acid strand comprising a 5' domain and a 3' domain linked to a quencher molecule; (b) a second nucleic acid strand comprising a 5' domain linked to a fluorescent molecule and bound to the 3' domain of the first nucleic acid strand; (c) a third nucleic acid strand comprising (i) a 5' domain that is complementary to the 3' domain of the first nucleic acid strand and (ii) a 3' domain that is complementary to the 5' domain of the first nucleic acid strand; (d) a fourth nucleic acid strand comprising a 5' domain and a 3' domain linked to a quencher molecule; (e) a fifth nucleic acid strand comprising a 5' domain linked to a fluorescent molecule and bound to the 3' domain of the fourth nucleic acid strand; and (f) a sixth nucleic acid strand comprising (i) a 5' domain that is complementary to the 3' domain of the fourth nucleic acid strand and (ii) a 3' domain that is complementary to the 5' domain of the fourth nucleic acid strand; wherein the 3' domain of the first nucleic acid strand and the 3' domain of the fourth nucleic acid strand have nucleotide compositions that are different from each other.

Further aspects of the present disclosure provide substrates, comprising (a) at least one discrete region comprising (i) a first nucleic acid strand comprising a 5' domain and a 3' domain linked to a quencher molecule, and (ii) a second nucleic acid strand comprising a 5' domain linked to a fluorescent molecule and bound to the 3' domain of the first nucleic acid strand; and (b) at least one discrete region comprising (i) a third nucleic acid strand comprising a 5' domain and a 3' domain linked to a quencher molecule, and (ii) a fourth nucleic acid strand comprising a 5' domain linked to a fluorescent molecule and bound to the 3' domain of the third nucleic acid strand, wherein the 3' domain of the first nucleic acid strand and the 3' domain of the third nucleic acid strand have nucleotide compositions that are different from each other.

Additional aspects of the present disclosure provide methods comprising patterning a substrate with a graphic design; depositing onto the graphic design in a predetermined pattern at least one of: (a) a first nucleic acid strand comprising a 5' domain and a 3' domain linked to a quencher molecule, and a second nucleic acid strand comprising a 5' domain linked to a fluorescent molecule and bound to the 3' domain of the first nucleic acid strand; and (b) a third nucleic acid strand comprising a 5' domain and a 3' domain linked to a quencher molecule, and a fourth nucleic acid strand comprising a 5' domain linked to a fluorescent molecule and bound to the 3' domain of the third nucleic acid strand.

In some embodiments, the methods further comprise depositing onto the graphic design at least one of: (c) a fifth nucleic acid strand comprising (i) a 5' domain that is complementary to the 3' domain of the first nucleic acid strand and (ii) a 3' domain that is complementary to the 5' domain of the first nucleic acid strand; and (d) a sixth nucleic acid strand comprising (i) a 5' domain that is complementary to the 3' domain of the third nucleic acid strand and (ii) a 3' domain that is complementary to the 5' domain of the third nucleic acid strand. In an embodiment, the graphic design is assayed for fluorescence. In some embodiments, the assay comprises exposing the graphic design to a transilluminator, optionally through a filter unit.

BRIEF DESCRIPTION OF THE DRAWINGS

FIG. 1 shows an example of a molecular verification system. A nucleic acid (e.g., DNA) primer 'key' triggers a molecular cascade to open the nucleic acid (e.g., RNA) toehold switch 'lock.' In this example, the lock encodes a reporter molecule that is expressed only in the presence of the correct key. Thus, an entity associated with the correct key activates a color change.

FIGS. 2A-2B show individual steps (cycles) of a multi-step of a multi-step primer exchange reaction (PER).

FIGS. 3A-3C show an example of a PER pathway using a primer and five catalytic hairpin molecules, resulting in the production of a trigger key that includes six domains.

FIGS. 5A-5E show an example of another molecular verification system that uses as the lock a catalytic hairpin system to encode recruitment of fluorescent molecules.

FIGS. 6A-6E show examples of a molecular verification system that implements logic computation using primer exchange reactions.

FIG. 7 shows that the efficacy of DNA trigger keys is comparably to plasmid-expressed RNA trigger keys.

FIG. 8 shows a gel demonstrating that a 3-letter code with only dATP, dTTP and dCTP, for example, may be used to synthesize a trigger key.

FIG. 9 shows that a trigger key synthesized via PER successfully activates toehold switch locks.

FIGS. 10A-10C show examples of chimeric and modified nucleic acids (oligonucleotides) for a replication protection verification system. FIG. 10A shows a molecular verification system comprised of two complementary chimeric oligonucleotides, one linked to a fluorescent molecule (star) and one linked to a quenching molecule. Hybridization of one oligonucleotide to the other oligonucleotide results in a loss of fluorescent signal. The chimeric oligonucleotides each include an L-DNA domain that inhibits enzymatic sequencing. FIG. 10B shows a molecular verification system comprised of two complementary catalytic hairpin molecules, one of which is linked to a fluorescent molecule and a quenching molecule such that fluorescence is quenched in the absence of binding to its complementary catalytic hairpin molecule. A fluorescent signal is produced only upon hybridization of the catalytic hairpin molecules to each other. FIG. 10C shows a variation on the molecular verification system of FIG. 10A whereby stopper molecules are included in the chimeric oligonucleotides to inhibit replication and sequencing.

FIGS. 11A-11D show examples of mechanisms that can be used to bring signal sequence domains together, for example, to bring together a primer key and a lock. FIG. 11A shows multiple sequences coming together through association of complementary domains such that the 'a' and 'e' domains are co-localized to trigger other processes. FIG. 11B shows two hairpin loops coming together by loop-loop interaction (b-b*). FIG. 11C shows two circular sequences coming together by loop-loop interaction (b-b*). FIG. 11D shows two circular sequences topologically linked.

FIGS. 12A-12D show a basic toehold exchange lock/key mechanism. In FIG. 12A, the 'X* a' strand binds to an exposed 'a*' toehold on an annealed complex that initially co-localizes a fluorophore (F) with a matching quencher (Q) in solution. The fluorescent signal is blocked in this configuration. When the strand displaces through the 'X' domain, it release the fluorophore-containing strand from the quencher, resulting in a fluorescent solution. FIG. 12B shows the key/lock pairs used in Example 7. The two lock solutions containing annealed fluorophore (F) and quencher (Q)-containing strands are denoted as '1' and '2' with circles around them. FIG. 12C shows the fluorescence measured from key mixtures containing ethanol concentrations from 0% to 70% mixed with equal volumes of annealed lock solutions (containing the fluorophore/quencher pair 1 depicted in FIG. 12B). The key solutions containing no key strand (light grey) or the wrong key strand (medium grey, corresponding to the key strand for fluorophore/quencher pair 2 depicted in FIG. 12B) had very little fluorescence under all ethanol conditions. When the key solution contained the correct key strand for the fluorophore/quencher pair (black bars), substantial fluorescence was measured. FIG. 12D shows a plot of the fluorescence given the correct key divided by the fluorescence given no key strand. Significant differentiation (>30× ON/OFF ratio) of successful key lock pairs was observed under the full range of ethanol conditions tested.

FIGS. 14A-14B show schematics of a graphic design application described in Example 7. FIG. 14A shows a schematic of the graphic design used in, and the results of, one of the experiments. FIG. 14B shows a schematic for interpreting the results.

FIG. 18A shows the attachment of additional fluorophores and quenchers (here, two of each), which results in a doubling of the signal output (X*). FIG. 18B shows an instance where multiple fluorophore strands are removed from the same quencher strand, resulting in increased fluorescent signaling (X1* and X2* are both labeled with fluorophores).

FIG. 19A shows an initial setup, where all of the hairpins are present in solution as the lock component of the system, each hairpin containing a fluorophore and quencher, for example. FIG. 19B shows they hybridization chain reaction (HCR), as a fixed number of fluorophores are activated from a single key strand. FIG. 19C shows the final product containing fluorophores.

FIG. 20A shows a series of unique unmodified key strands as well as a test strip, which is used generate a unique barcode pattern which is then verified on a manufacturer's website. FIG. 20B shows a system where the given unmodified key system is time-sensitive; the expiration date and serial number ensure that the correct product is authenticated.

DETAILED DESCRIPTION

Figure 4:
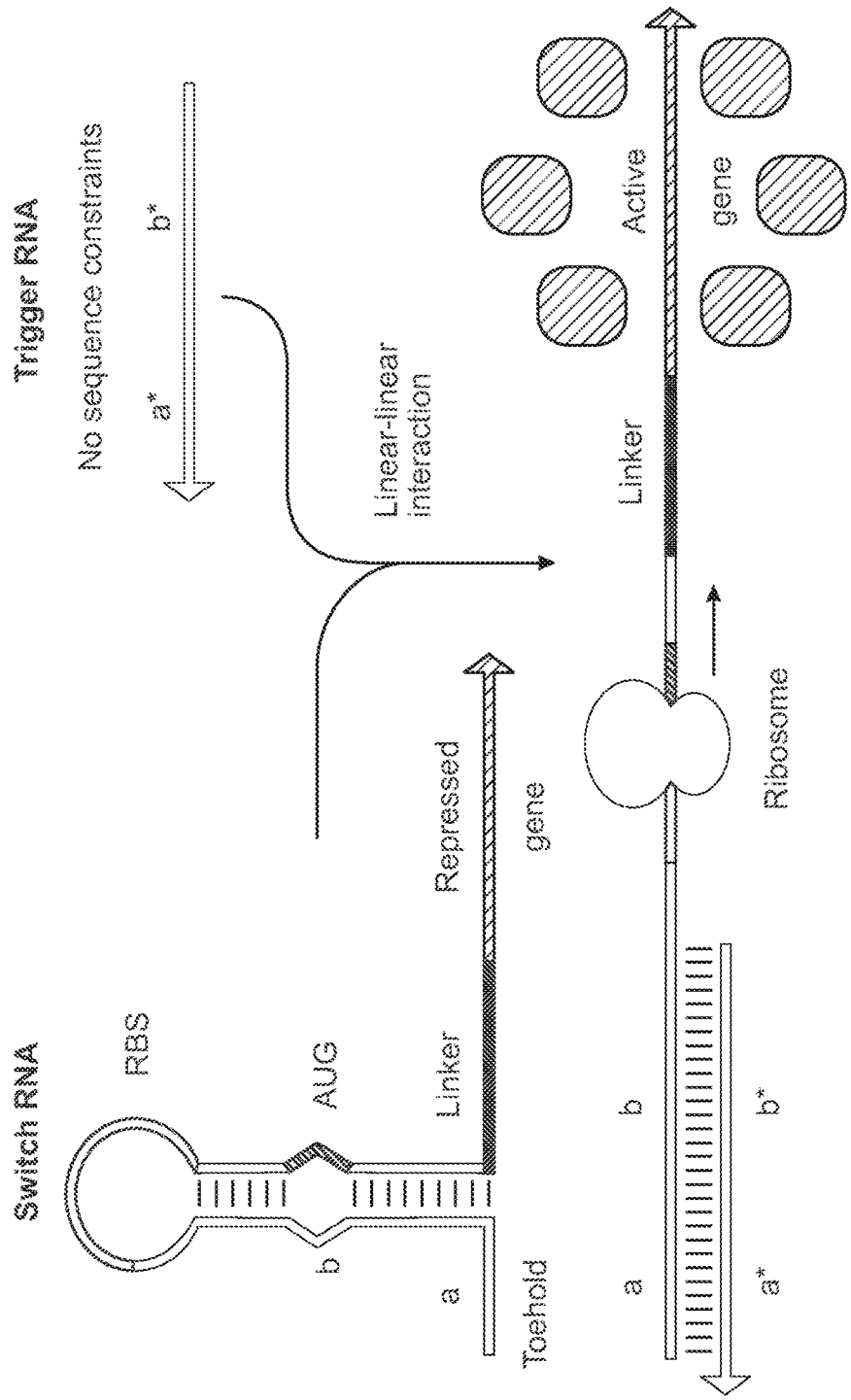
FIG. 4 shows a schematic of the toehold switch lock. The corresponding taRNA has the sequence 5'-b*-a*-3' where domains a* and b* are the reverse complements of domains a and b, respectively. Toehold switch locks are RNA-dependent translation activators. In the presence of its cognate nucleic acid trigger key, a toehold switch lock changes its conformation to enable translation of the downstream open reading frame encoding, for example, a reporter protein.

Provided herein are molecular verification systems (e.g., compositions, methods and kits) that can be used to authenticate the identity of a person, a group of people or compositions, for example. Unique molecular keys are provided to the entity requiring identify verification and presented to an entity in possession of a molecular lock system. In some embodiments, a molecular verification system uses four main components: (1) a primer key and (2) catalytic molecules, which are used to synthesize a (3) trigger key that can open a (4) toehold switch lock. As shown in FIG. 1, primer keys may be referred to as molecular identifiers, and catalytic molecules and toehold switch locks together may be referred to as molecular decoders.

Primer Keys

A "primer key," generally, is a nucleic acid (e.g., single-stranded nucleic acid, also referred to as an oligonucleotide) having a nucleotide sequence (domain) complementary to a domain located on a nucleic acid "lock." In some embodiments, the lock is a catalytic molecule. In other embodiments, the lock is a toehold switch. In yet other embodiments, the lock is a simply a complementary nucleic acid comprising (e.g., linked to) a functional molecule, such as a fluorescent molecule or a quenching molecule.

In some embodiments, a primer key is a nucleic acid (e.g., single-stranded oligonucleotide) having a nucleotide sequence (primer domain) complementary to toehold domain of a catalytic molecule or a toehold domain of a toehold switch lock. A primer key can function, in some embodiments, as a typical primer in that when bound to another nucleic acid (e.g., catalytic molecule or toehold switch), is the starting point for polymerization in the presence of a polymerase. Thus, in some embodiments, a primer key binds to a catalytic molecule to initiate a primer exchange reaction. As discussed in greater detail below, the extension product released at the end of a primer exchange reaction is referred to as a 'trigger key.' A trigger key is able to open (linearize) a toehold switch lock.

In other embodiments, a primer key is simply a single-stranded nucleic acid having at least one domain complementary to a lock.

Primer keys, in some embodiments, are shorter than conventional nucleic acid primers. This helps to prevent security breaches by hindering 'decoding' of the primer key sequence. It is difficult to amplify short nucleic acid sequences for subsequent sequencing analysis. Thus, in some embodiments, a primer key (or a primer domain of a primer key, which is the nucleotide sequence that binds to the toehold domain of a catalytic molecule or a toehold switch lock) has length of less than 18 nucleotides in length. For example, a primer key may have a length of 4-17, 4-16, 4-15, 4-14, 4-13, 4-12, 4-11, 4-10, 4-9, 4-8, 5-17, 5-16, 5-15, 5-14, 5-13, 5-12, 5-11, 5-10, 5-9, 5-8, 6-17, 6-16, 6-15, 6-14, 6-13, 6-12, 6-11, 6-10, 6- 9, 6-8, 7-17, 7-16, 7-15, 7-14, 7-13, 7-12, 7-11, 7-10, 7-9, 7-8, 8-17, 8-16, 8-15, 8-14, 8-13, 8-12, 8-11, 8-10, 8-9, 9-17, 9-18, 9-15, 9-14, 9-13, 9-12, 9-11, 9-10, 10-17, 10-16, 10-15, 10-14, 10-13, 10-12, 10-11, 10-10, 10-9 or 10-8 nucleotides. In some embodiments, a primer key has length of 4, 5, 6, 7, 8, 9, 10, 11, 12, 13, 14, 15, 16, 17 or 18 nucleotides. In some embodiments, a primer key has length of less than 15 nucleotides in length.

In some embodiments, for example, in embodiments where a primer exchange reaction is not used, a primer key (or a primer domain of a primer key) has a length of greater than 15 nucleotides. In some embodiments, a primer key (or a primer domain of a primer key) has a length of 10-50 nucleotides. For example, a primer key (or a primer domain of a primer key) may have a length of 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45 or 45-50 nucleotides. In some embodiments, a primer key (or a primer domain of a primer key) has a length of 10, 15, 20, 25, 30, 35, 40, 45 or 50 nucleotides. In some embodiments, a primer key (or a primer domain of a primer key) has a length of 15, 16, 17, 18, 19, 20, 21, 22, 23, 24 or 25 nucleotides. A primer key (or a primer domain of a primer key), in some embodiments, is longer than 50 nucleotides, or shorter than 10 nucleotides. It should be understood that the length of a primer key (or a primer domain of a primer key) depends, at least in part, on the length of a toehold domain of a catalytic molecule or a toehold switch lock.

A primer key may be present in an aqueous solution or in dried (lyophilized) form. In some embodiments, a primer key is present in an ink solution, for example, carried in a pen by a person requiring identity authentication. In some embodiments, a primer key is present in an alcohol (e.g., ethanol) solution, such as a fragrance (e.g., perfume) that contains a certain percentage of alcohol. For example, an alcohol (e.g., ethanol) solution may include at least 5%, 10%, 20%, 30%, 40%, 50%, 60%, 70%, 80%, 90%, or 100% alcohol. In some embodiments, a primer key is present in a 70% alcohol (e.g., ethanol) solution. In some embodiments, a primer key in solution (e.g., aqueous buffer) is applied to (e.g., sprayed onto) a product or other composition/entity and dried for long term storage and transportation. In this way, products (e.g., commercial products) may be 'coded' with a unique identity. In some embodiments, the primer key is not mixed in with product (e.g., perfume), and may be present on a tag (such as a paper) that is attached to the vessel (i.e., container) containing the product. In such embodiments, the lock solution, in liquid form, may be applied to the tag comprising the key, and a visible color change indicates a lock-key match. The system may also be set up in reverse: the keys may be present in liquid form and the locks may be present on a tag. In some embodiments, the tag is not connected to the vessel.

In some embodiments, a primer key is combined with additional molecules to further conceal the identity of the primer key sequence. Such additional molecules include, for example, random sequence oligonucleotides, proteins, or peptides.

In some embodiments, the ratio of primer key to additional molecules is varied.

In some embodiments, the concentration of a primer key is varied. For example, a threshold concentration or an exact concentration of a primer key may be required to successfully bind to a catalytic molecule or toehold switch lock (open a lock). For example, exactly 2 pM of a specific primer key may be required to open a lock, and a higher or lower concentration will fail to open the lock.

Primer keys, in some embodiments, include within the nucleotide sequence of the primer key, molecules that inhibit replication and/or sequencing. For example, in some embodiments, a primer key includes "stoppers," such as spacers, synthetic nucleotides and modified nucleotides. Examples of modified nucleotides or nucleotide domains (more than one contiguous nucleotide) include, but are not limited to, XNA, PNA and LNA. Other stoppers (molecules or modifications that terminates polymerization) are described elsewhere herein. In some embodiments, the primer keys may comprise unmodified (i.e., naturally occurring) nucleotide bases.

In some embodiments, a primer key includes a L-DNA. D-DNA is the naturally occurring form of DNA which forms the canonical right helix, although its mirror image L-DNA can be chemically synthesized. Chimeric molecules, comprised partially of D-DNA and partially of L-DNA can also be synthesized. L-DNA domains are not typically recognized by polymerases. They can, therefore, serve, in some embodiments, as effective inhibitors for enzymatic sequencing methods. Thus, provided herein are chimeric primer keys comprising L-DNA domains and D-DNA. An example of these chimeric primers are shown in FIGS. 10A-10C. Other chimeric primer keys are encompassed herein.

Figure 15:
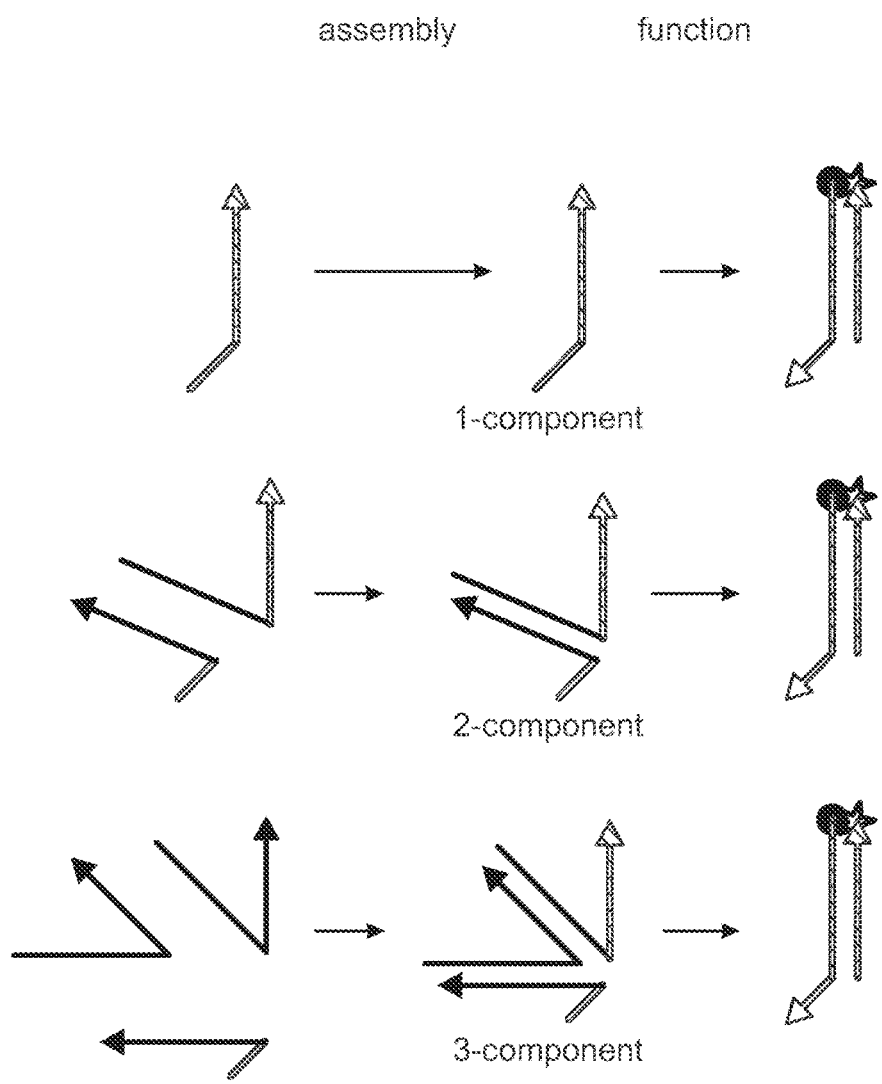
FIG. 15 shows examples of multi-component keys that may be used as provide herein. The schematic designs in the left panel show 1-, 2-, and 3-component keys, and the graph in the right panel shows the respective drop in assembled state relative to drop in key component concentration among the three different key configurations.
Figure 15:
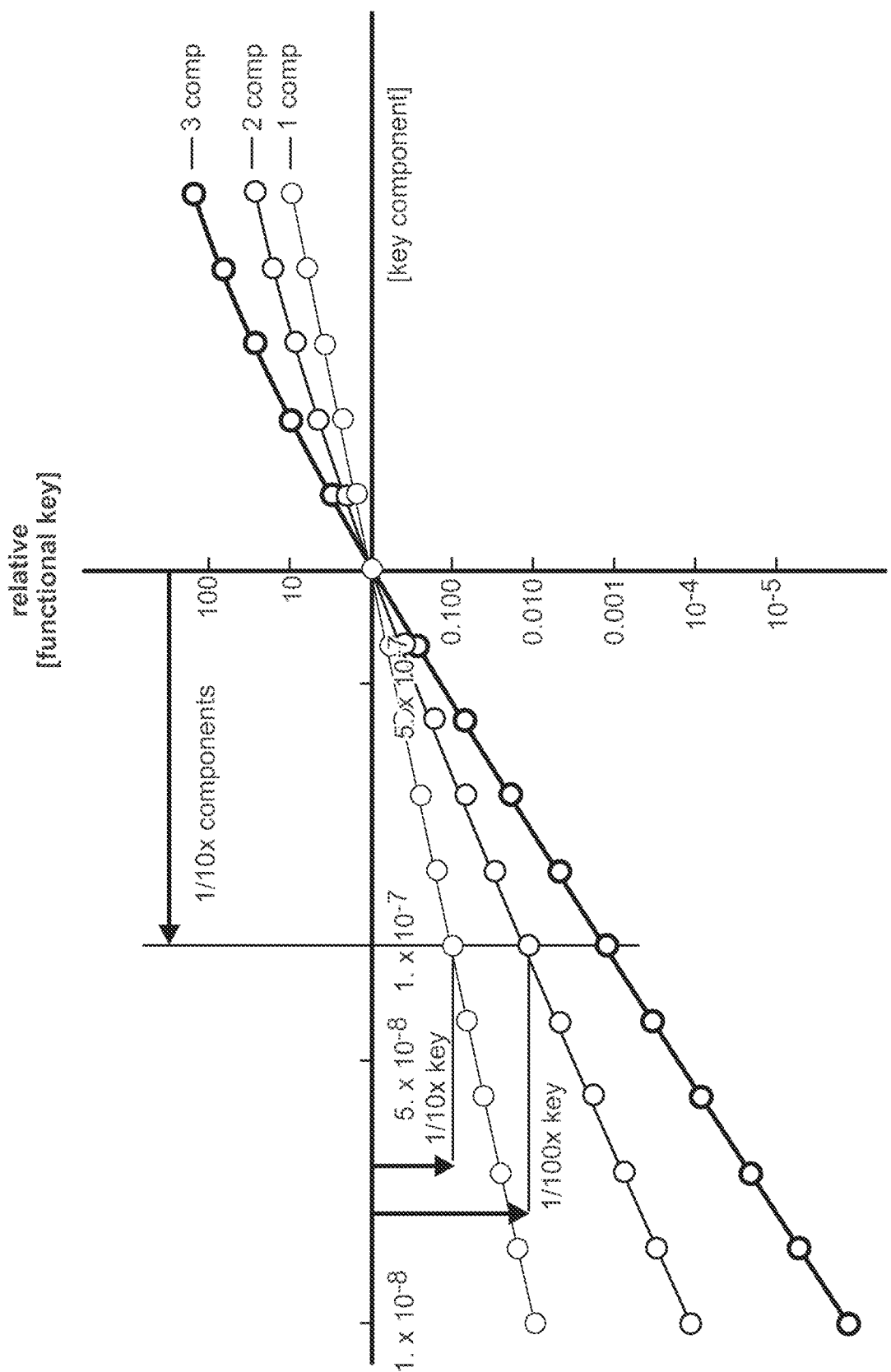

In some instances, diluted substances (e.g., perfume) may test positive under an encryption test because there is some quantity of "real" substance present. In order to combat this solution, the "key" can be split into multiple components held together by weak hybridization, as shown in FIG. 15. Without wishing to be bound by theory, this may render key function more dependent on component concentration. For a single-component key, a 10-fold drop in key concentration yields a ⅒× concentration of key in the test. However, in a 2-component system, the same 10-fold drop yields, for example, a 100-fold drop in functional (assembled) key, decreasing the chance of misidentifying a diluted fake. In some embodiments, the same 10-fold drop may yield a 20-fold to 1000-fold (e.g., 30-fold, 40-fold, 50-fold, 60-fold, 70-fold, 80-fold, 90-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold) or greater drop in functional (assembled) key depending, at least in part on sequence design and reaction conditions. More components lead to a larger effect, as demonstrated by the 3-component model in FIG. 15. Strand interactions that stabilize the key may also be adjusted arbitrarily in design by changing DNA sequences and domain lengths.

Thus, in some embodiments, a key is a complex comprising 2, 3 or more strands weakly bound to each other. In some embodiments, a key comprises (a) a first nucleic acid strand comprising a 5' domain and a 3' domain, and (b) a second nucleic acid strand comprising a 5' domain and a 3' domain, wherein the 3' domain of the second nucleic acid strand is bound (e.g., weakly bound) to the 5' domain of the first nucleic acid strand, wherein the 3' domain of the first nucleic acid strand is complementary to a nucleic acid strand linked to a fluorescent molecule. In other embodiments, a key comprises (a) a first nucleic acid strand comprising a 5' domain and a 3' domain, (b) a second nucleic acid strand comprising a 5' domain and a 3' domain, and (c) a third nucleic acid strand comprising a 5' domain and a 3' domain, wherein the 3' domain of the second nucleic acid strand is bound (e.g., weakly bound) to the 5' domain of the first nucleic acid strand, wherein the 5' domain of the second nucleic acid strand is bound (e.g., weakly bound) to the 3' domain of the third nucleic acid strand, and wherein the 3' domain of the first nucleic acid strand is complementary to a nucleic acid strand linked to a fluorescent molecule.

Catalytic Molecules

Catalytic molecules are used, in some embodiments, as a component of a lock system, to synthesize a trigger key from a starting primer key. A catalytic nucleic acid molecule ("catalytic molecule") generally includes an unpaired (single-stranded) 3' toehold domain and a paired (double-stranded) domain 5' from (and, in some embodiments, directly adjacent to) the 3' toehold domain. "Catalytic hairpin molecules" also include a loop domain. The kinetics of primer exchange reactions can be controlled by modifying the length, composition and concentration of the catalytic molecules (e.g., one or more domains of the catalytic molecules), for example.

A catalytic hairpin (see FIG. 2A as an illustrative example) includes an unpaired 3' toehold domain ("1'") linked to a paired hairpin stem domain (e.g., formed by intramolecular binding of subdomain "2" to subdomain "2'") linked to a hairpin loop domain (loop-like structure). The term "unpaired" is used herein to refer to nucleic acids/nucleotide sequences, more particularly domains of nucleic acids, that are not bound to a complementary nucleic acids/sequences. In some embodiments, an unpaired domain may simple be a region on a single-stranded nucleic acid. In other embodiments, an unpaired domain is a region on a partially double-stranded molecule (a nucleic acid molecule than includes a paired domain and an unpaired domain). An example of an unpaired domain of a partially double-stranded molecule is a toehold domain as shown, for example, in FIG. 2A (domain 1'). Likewise, the term "paired" is used herein to refer to nucleic acids/nucleotide sequences, more particularly domains of nucleic acids, that are bound to a complementary nucleic acids/sequences. An example of a paired domain of a partially double-stranded molecule is a stem domain as shown, for example, in FIG. 2A (domain 2' bound to domain 2).

The length of a catalytic molecule (e.g., catalytic hairpin molecule) may vary. In some embodiments, a catalytic molecule has a length of 25-300 nucleotides. For example, a catalytic molecule may have a length of 25-250, 25-200, 25-150, 25-100, 25-50, 50-300, 50-250, 50-200, 50-150 or 50-100 nucleotides. In some embodiments, a catalytic molecule has a length of 30-50, 40-60, 50-70, 60-80, 70-90, 80-100, 100-125, 100-150 or 100-200 nucleotides. In some embodiments, a catalytic molecule has a length of 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides. A catalytic molecule, in some embodiments, is longer than 300 nucleotides, or shorter than 25 nucleotides.

A "toehold domain" refers to an unpaired sequence of nucleotides located at the 3' end of the catalytic molecule and is complementary to (and binds to) a nucleotide sequence of a primer key (or primer domain of a primer key). The length of a toehold domain may vary. In some embodiments, a toehold domain has a length of 4-17, 4-16, 4-15, 4-14, 4-13, 4-12, 4-11, 4-10, 4-9, 4-8, 5-17, 5-16, 5-15, 5-14, 5-13, 5-12, 5-11, 5-10, 5-9, 5-8, 6-17, 6-16, 6-15, 6-14, 6-13, 6-12, 6-11, 6-10, 6-9, 6-8, 7-17, 7-16, 7-15, 7-14, 7-13, 7-12, 7-11, 7-10, 7-9, 7-8, 8-17, 8-16, 8-15, 8-14, 8-13, 8-12, 8-11, 8-10, 8-9, 9-17, 9-18, 9-15, 9-14, 9-13, 9-12, 9-11, 9-10, 10-17, 10-16, 10-15, 10-14, 10-13, 10-12, 10-11, 10-10, 10-9 or 10-8 nucleotides. In some embodiments, a toehold domain has length of 4, 5, 6, 7, 8, 9, 10, 11, 12, 13, 14, 15, 16, 17 or 18 nucleotides. In some embodiments, a toehold domain has a length of 5-40 nucleotides. For example, a toehold domain may have a length of 2-35, 2-30, 2-25, 2-20, 2-15, 2-10, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a toehold domain has a length of 5, 10, 15, 20, 25, 30, 35 or 40 nucleotides. In some embodiments, a toehold domain has a length of 10, 11, 12, 13, 14, 15, 16, 17, 18, 19, 20, 21, 22, 23, 24 or 25 nucleotides. A toehold domain, in some embodiments, is longer than 40 nucleotides, or shorter than 5 nucleotides.

A primer key (or a primer domain of a primer key), in some embodiments, binds to a 3' unpaired (single-stranded) toehold domain of a catalytic molecule to initial a primer exchange reaction. In this reaction (see FIG. 2A as an illustrative example), the primer key ("1") binds to the toehold domain of a catalytic molecule ("1'"), and extension of the primer key by a strand displacement polymerase present in the reaction solution displaces one of the subdomains ("2") of the stem domain of the catalytic molecule through a branch migration process. The overall effect is that one of the subdomains ("2") of the hairpin stem domain is replaced with an extended (newly synthesized) primer domain.

A "paired domain" or a "stem domain" of a catalytic molecule refers to a paired sequence of nucleotides (e.g., Watson-Crick nucleobase pairing) located 5' from (and, in some embodiments, directly adjacent to) the unpaired toehold domain of a catalytic molecule. The paired stem domain of a catalytic hairpin molecule is formed by intramolecular base pairing (base pairing between nucleotides within the same molecule) of two subdomains of a catalytic hairpin molecule: e.g., an internal/central subdomain located 5' from the toehold domain bound (hybridized) to a subdomain located at the 5' end of the catalytic hairpin. The length of a paired domain may vary. In some embodiments, a paired domain has a length of 5-40 nucleotides. For example, a paired domain may have a length of 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a paired domain has a length of 5, 10, 15, 20, 25, 30, 35 or 40 nucleotides. In some embodiments, a paired domain has a length of 10, 11, 12, 13, 14, 15, 16, 17, 18, 19, 20, 21, 22, 23, 24 or 25 nucleotides. A paired domain, in some embodiments, is longer than 40 nucleotides, or shorter than 5 nucleotides.

While a paired domain is generally formed by intramolecular base pairing of two subdomains of a catalytic molecule (or a toehold switch, as discussed below), it should be understood that a paired stem domain may contain at least one mismatch pair (e.g., pairing of A with C or G, or pairing of T with C or G). In some embodiments, the stem domain has 1-5 mismatch nucleotide base pairs. For example, a paired domain may be have 1, 2, 3, 4 or 5 mismatch nucleotide base pairs.

A "loop domain" of a catalytic hairpin refers to a primarily unpaired sequence of nucleotides that form a loop-like structure at the end (adjacent to) of the stem domain. The length of a loop domain may vary. In some embodiments, an loop domain has a length 3-200 nucleotides. For example, a loop domain may have a length of 3-175, 3-150, 3-125, 3-100, 3-75, 3-50, 3-25, 4-175, 4-150, 4-125, 4-100, 4-75, 4-50, 4-25, 5-175, 5-150, 5-125, 5-100, 5-75, 5-50 or 5-25 nucleotides. In some embodiments, a loop domain has a length of 3-10, 3-15, 32-10, 3-25, 3-30, 3-35, 3-40, 3-35, 3-40, 3-45, 3-50, 4-10, 4-15, 4-10, 4-25, 4-30, 4-35, 4-40, 4-35, 4-40, 4-45 or 4-50 nucleotides. In some embodiments, a loop domain has a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49 or 50 nucleotides. A loop domain, in some embodiments, is longer than 300 nucleotides.

In some embodiments, a catalytic molecule does not contain a hairpin loop domain. For example, a catalytic molecule may simply be a duplex comprising a 3' unpaired toehold domain adjacent to a paired domain, similar to a stem domain (without the adjacent loop domain). Catalytic molecules that do not include a loop domain may be stabilized at the end opposite the 3' toehold domain through crosslinking or nucleotide base complementarity between a stretch (e.g., 10 or more) nucleotide base pairs.

A "set of catalytic molecules" specifies the synthesis of a trigger key. Thus, a set of catalytic molecules typically includes all domains of a trigger key needed to open a toehold switch lock. In some embodiments, a set of catalytic molecules includes 3-20 catalytic molecules. For example, a set of catalytic molecules may include 3, 4, 5, 6, 7, 8, 9, 10, 12, 15, or 20 catalytic molecules. In some embodiments, a set of catalytic molecules includes 3-5, 3-10, 3-15, 5-10, 5-15, or 5-20 catalytic molecules. Catalytic molecules of a set are typically different from each other in that each stem domain includes a different sequence relative to the stem domains of the other catalytic molecules of the set. However, the toehold domain of each catalytic molecule includes a sequence that is complementary to a stem domain in only one other catalytic molecule of the set. The exception to this rule is the catalytic molecule to which the primer key initially binds. As shown in FIG. 3A, primer 'a' binds to domain a* of catalytic molecule 'A'. For the remaining catalytic molecules of the set, the toehold domain sequence is the same as (or complementary to) the stem sequence of one other catalytic molecule of the set. Toehold domain 'b*' of catalytic molecule 'B' is complementary to domain 'b' of catalytic molecule 'A'. Toehold domain 'c*' of catalytic molecule 'C' is complementary to domain 'c' of catalytic molecule 'B'. Toehold domain 'd*' of catalytic molecule 'D' is complementary to domain 'd' of catalytic molecule 'C'. Toehold domain 'e*' of catalytic molecule 'E' is complementary to domain 'e' of catalytic molecule 'D'.

Figure 19A:
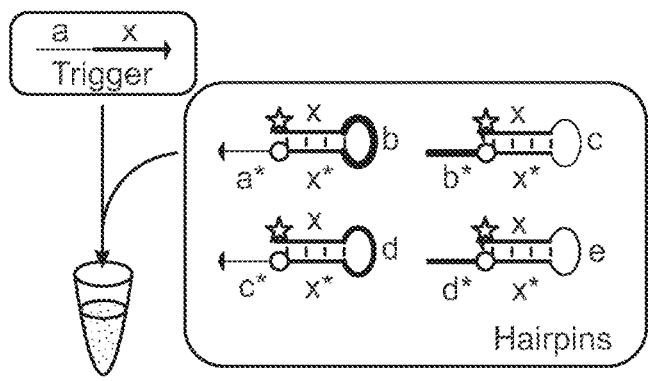
FIGS. 19A-19C are schematics depicting further mechanisms of fixed amplification, as described in Example 10.
Figure 19B:
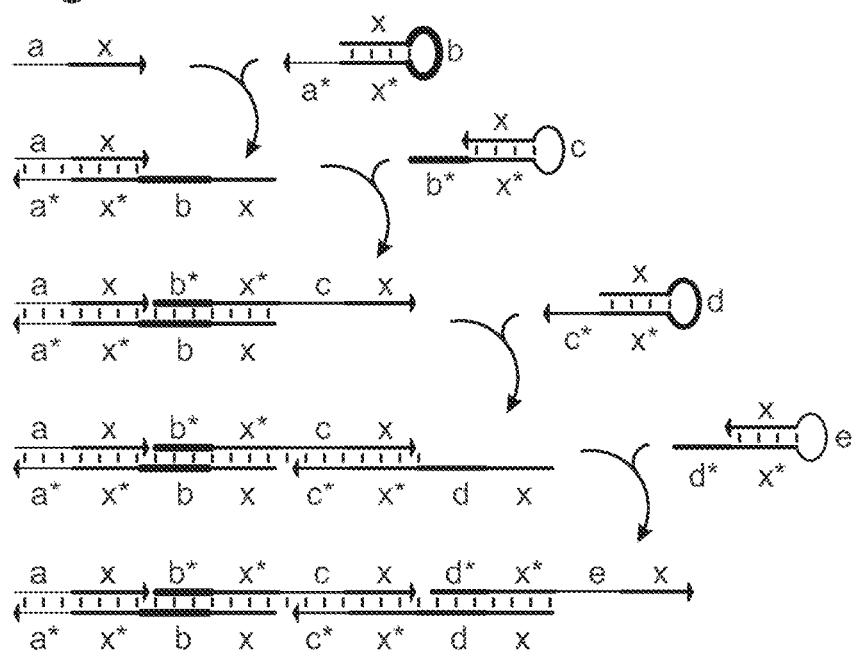
Figure 19C:
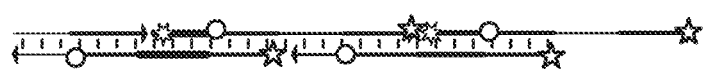

In some embodiments, the set of catalytic molecules may be used in a programmed manner (i.e., hybridization chain reaction, HCR) to amplify a fluorescent signal. As shown in FIGS. 19A-19C, the hairpins may hold one or more fluorophore and/or quencher moieties, and then undergo the PER described above, leading to a double-stranded product with an amplified and programmed level of fluorescence. Note that both the hairpin/inactive state and the activated polymer state are thermodynamic equilibrium states, giving the system stability in storage.

Trigger Keys

A trigger key is capable of opening a toehold switch lock (altering the hairpin/stem domain of a toehold switch lock). These trigger keys work in trans, and thus may be referred to herein as trans-activating nucleic acids (e.g., trans-activating RNA or taRNA).

A trigger key, in some embodiments, is synthesized using a primer exchange reaction that includes a primer key and a "set of catalytic molecules." Each catalytic molecule of a set includes a domain corresponding to a domain on the toehold switch lock, thus each catalytic molecule "specifies" a reverse complement domain that is complementary to and capable of binding to a domain on a particular toehold switch lock.

Trigger keys may be DNA or RNA, or a combination of both DNA and RNA. In some embodiments, the trigger key is mRNA. In some embodiments, the trigger key is rRNA or any other non-coding RNA (e.g., sRNA).

Those of ordinary skill will be able to identify suitable trigger key sequences. This can be accomplished, for example, by screening switch toehold domain sequences for their ability to bind specifically and selectively to only the trigger(s) of interest. Such screens can be performed under conditions that mimic conditions under which the switch will bind to its cognate trigger.

The length of a trigger key depends, at least in part, on the length of the toehold switch lock. In some embodiments, a trigger key has a length of 20-100 nucleotides. For example, a trigger key may have a length of 20-90, 20-80, 20-70, 20-60, 20-50, 20-40, 20-30, 30-100, 30-90, 30-80, 30-70, 30-60, 30-50, 30-40, 40-100, 40-90, 40-80, 40-70, 40-60, 40-50, 50-100, 50-90, 50-80, 50-70, 50-60, 60-100, 60-90, 60-80, 60-70 nucleotides. In some embodiments, a trigger key has a length of 20, 25, 30, 35, 40, 45, 50, 55, 60, 65, 70, 75, 80, 85, 90, 95 or 100 nucleotides. In some embodiments, a trigger key has a length of longer than 100 nucleotides.

The trigger may comprise a first domain that hybridizes to a toehold domain of any of the foregoing riboregulator switches and that comprises no or minimal secondary structure, and a second domain that hybridizes to a sequence downstream (3') of the toehold domain (a sequence contributing to the stem domain including optionally the first paired region of the stem domain). The first domain may be 100% complementary to the toehold domain. The second domain may be less than 100% complementary to the sequence downstream of the toehold domain.

The trigger may consist of more than one nucleic acid strand, and such multiple strands in combination provide the first and second domain for hybridization with the toehold riboregulator switch. In some embodiments, one or more other nucleic acids may be used to bring multiple triggers (or partial trigger sequences) into close proximity via hybridization to enable them to efficiently hybridize with the riboregulator switch.

In some embodiments, a trigger key hybridizes to the toehold domain and the first paired domain of the toehold switch lock and does not hybridize to the unpaired bulge.

A trigger key may comprise secondary structure, such as for example hairpin structures, provided such hairpin structures do not interfere with hybridization of the trigger key to the switch lock or to each other.

Fluorescent Molecules and Quenching Molecules

In some embodiments, the nucleic acids of the present disclosure include a (at least one) fluorescent molecule, such as a fluorophore. Non-limiting examples of fluorescent molecules include 5-FAM, Calcein, DiO, Fluorescein, FLUO-3, FLUO-4, EGFP, GFP, Oregon Green 514, QuantiFluor™ dsDNA, QuantiFluor™ ssDNA, QuantiFluor™ RNA, Rhodamine Green, SYBR Gold, SYBR Green, SYTO 9, SYTOX® Green, YFP, Alexa Fluor 555, Cy3, Ethidium Bromide, Ethidium Homodimer-1, Propidium Iodide, Resorufin, RFP, Rhod-2, Rhodamine Red, SYTOX Orange, TAMRA, Texas Red, TRITC, Allophycocyanin, Cy5, DRAQS, SYTOX Red, SYTOX Blue and wtGFP.

In some embodiments, the nucleic acids of the present disclosure include a (at least one) quenching molecule. Quenching refers to any process which decreases the fluorescence intensity of a given substance. A variety of processes can result in quenching, such as excited state reactions, energy transfer, complex-formation and collisional quenching. Molecular oxygen, iodide ions and acrylamide are non-limiting examples of chemical quenchers. The chloride ion is a well-known quencher for quinine fluorescence.

When fluorescent molecules and quencher molecules are used in a key/lock authentication system of the present disclosure, in some embodiments, at least one fluorescent molecule is positioned on a nucleic acid key strand and at least one molecule is positioned on a nucleic acid lock strand such that when then key stand binds to the lock strand, a fluorescent molecule and a quencher molecule are brought into close proximity to each other (e.g., are juxtaposed), resulting in quenching of fluorescent signal otherwise emitted by the fluorescent molecule. In other embodiments, at least one fluorescent molecule is positioned on a nucleic acid lock strand and at least one molecule is positioned on a nucleic acid key strand such that when then key stand binds to the lock strand, a fluorescent molecule and a quencher molecule are brought into close proximity to each other, resulting in quenching of fluorescent signal.

In some embodiments, a fluorescent molecule and a quencher molecule are both located on the same lock strand or the same key strand, and the strand is configured such that the fluorescent molecule and the quencher molecule are brought into close proximity to each other, resulting in quenching of fluorescent signal. For example, the strand containing both the fluorescent molecule and the quencher molecule may form a hairpin (see, e.g., FIG. 10B).

It should be understood that in any of the embodiments provided herein where a nucleic acid strand containing a fluorescent molecule binds to a nucleic acid strand containing a quencher molecule, a quencher molecule on a nucleic acid strand (key strand or lock strand) may be substituted for a fluorescent molecule, provided the fluorescent molecule on the complementary strand is substituted with a quencher molecule, such that binding of the two strands results in quenching of fluorescent signal. Likewise, a fluorescent molecule on a nucleic acid strand (key strand or lock strand) may be substituted for a quencher molecule, provided the quencher molecule on the complementary strand is substituted with a fluorescent molecule, such that binding of the two strands results in quenching of fluorescent signal.

Figure 18A:
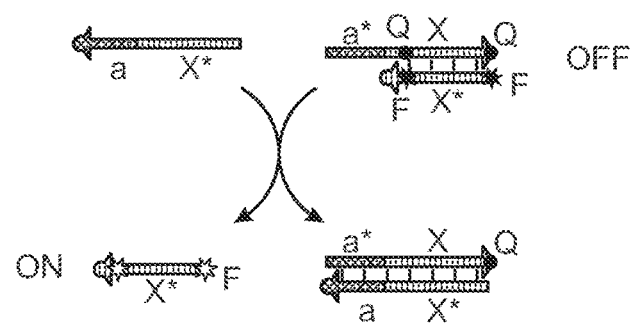
FIGS. 18A-18B are schematics depicting mechanisms of fixed amplification described in Example 10.

In some embodiments, a key/lock system (including compositions, kits, and/or methods) includes (a) a first nucleic acid strand (e.g., a key strand) comprising a 5' domain and a 3' domain, (b) a second nucleic acid strand (e.g., a lock strand) comprising a 5' domain complementary to the 3' domain of the first strand, a 3' domain complementary to the 5' domain of the first strand, and two quencher molecules separated from each other by x nucleotides of the 3' domain of the second strand, and (c) a third nucleic acid strand (e.g., another lock strand) comprising a 5' domain complementary to the 3' domain of the second strand, and two fluorescent molecules separated from each other by x nucleotides of the 5' domain of the third strand, wherein binding of the third nucleic acid strand to the second nucleic acid strand quenches fluorescent signal emitted by the two fluorescent molecules, and x is greater than zero (see, e.g., FIG. 18A).

In some embodiments, the second nucleic acid strand comprises the fluorescent molecules and the third nucleic acid strand comprises the quencher molecules. Thus, in some embodiments, a key/lock system (including compositions, kits, and/or methods) includes (a) a first nucleic acid strand (e.g., a key strand) comprising a 5' domain and a 3' domain, (b) a second nucleic acid strand (e.g., a lock strand) comprising a 5' domain complementary to the 3' domain of the first strand, a 3' domain complementary to the 5' domain of the first strand, and two fluorescent molecules separated from each other by x nucleotides of the 3' domain of the second strand, and (c) a third nucleic acid strand (e.g., another lock strand) comprising a 5' domain complementary to the 3' domain of the second strand, and two quencher molecules separated from each other by x nucleotides of the 5' domain of the third strand, wherein binding of the third nucleic acid strand to the second nucleic acid strand quenches fluorescent signal emitted by the two fluorescent molecules, and x is greater than zero.

In some embodiments, x is 1-50, 2-50, 3-50, 4-50, 5-50, 1-20, 2-20, 3-20, 4-20, 5-20, 1-10, 2-10, 3-10, 4-10, or 5-10 nucleotides.

Figure 18B:
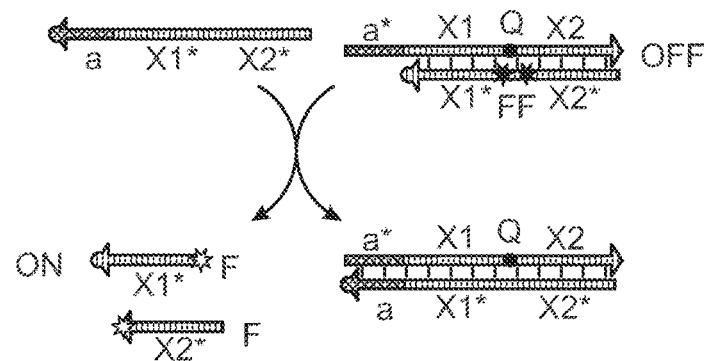

In some embodiments, a key/lock system (including compositions, kits, and/or methods) includes (a) a first nucleic acid strand comprising a first 5' subdomain, a second 5' subdomain, and a 3' domain, (b) a second nucleic acid strand comprising a 5' domain complementary to the 3' domain of the first strand, a first 3' subdomain complementary to the second 5' subdomain of the first strand, a second 3' subdomain complementary to the first 5' subdomain of the first strand, and a quencher molecule separating the first 3' subdomain of the second strands from the second 3' subdomain of the second strand, (c) a third nucleic acid strand comprising a 5' domain complementary to the first 3' subdomain of the second strand, and a 5' fluorescent molecule, and (d) a fourth nucleic acid strand comprising a 5' domain complementary to the second 3' subdomain of the second strand, and a 3' fluorescent molecule, wherein binding of the third nucleic acid strand and the fourth nucleic acid strand to the second nucleic acid strand quenches fluorescent signal emitted by the 5' fluorescent molecule and the 3' fluorescent molecule (see, e.g., FIG. 18B).

In some embodiments, a key/lock system (including compositions, kits, and/or methods) includes (a) a first nucleic acid strand comprising a first 5' subdomain, a second 5' subdomain, and a 3' domain, (b) a second nucleic acid strand comprising a 5' domain complementary to the 3' domain of the first strand, a first 3' subdomain complementary to the second 5' subdomain of the first strand, a second 3' subdomain complementary to the first 5' subdomain of the first strand, and a fluorescent molecule separating the first 3' subdomain of the second strands from the second 3' subdomain of the second strand, (c) a third nucleic acid strand comprising a 5' domain complementary to the first 3' subdomain of the second strand, and a 5' quencher molecule, and (d) a fourth nucleic acid strand comprising a 5' domain complementary to the second 3' subdomain of the second strand, and a 3' quencher molecule, wherein binding of the third nucleic acid strand and the fourth nucleic acid strand to the second nucleic acid strand quenches fluorescent signal emitted by the fluorescent molecule.

In some embodiments, a key/lock system (including compositions, kits, and/or methods) includes (a) a first nucleic acid strand comprising a 5' domain, a 3' domain, and a 5' fluorescent molecule or a 5' quencher molecule, and (b) a second nucleic acid strand comprising a 5' domain complementary to the 3' domain of the first strand, a 3' domain complementary to the 5' domain of the first strand, and a 3' quencher molecule or 3' fluorescent molecule, wherein binding of the second nucleic acid strand to the first nucleic acid strand quenches fluorescent signal emitted by the 5' fluorescent molecule or the 3' fluorescent molecule (see, e.g., FIG. 10A). In some embodiments, the first strand comprises a 5' fluorescent molecule and the second strand comprises a 3' quencher molecule, and binding of the first strand to the second strand quenches fluorescent signal emitted by the 5' fluorescent molecule. In other embodiments, the first strand comprises a 5' quencher molecule and the second strand comprises a 3' fluorescent molecule, and binding of the first strand to the second strand quenches fluorescent signal emitted by the 3' fluorescent molecule.

In some embodiments, a key/lock system (including compositions, kits, and/or methods) includes (a) a first nucleic acid strand comprising a 5' domain, a loop domain, and a 3' domain complementary to the 5' domain, and (b) a second nucleic acid strand comprising a 5' end, a 5' domain, a loop domain, a 3' domain complementary to the 5' domain, and a 3' end, wherein one end comprises a fluorescent molecule and the other end comprises a quencher molecule, wherein binding of the 5' domain of the second strand to the 3' domain of the second strand quenches fluorescent signal emitted by the fluorescent molecule (see, e.g., FIG. 10B (top)). In some embodiments, a key/lock system (including compositions, kits, and/or methods) includes (a) a first nucleic acid strand comprising a 5' domain and a 3' domain, and (b) a second nucleic acid strand comprising a 5' domain, a loop domain, a first 3' subdomain complementary to the 5' domain of the second strand and complementary to the 3' domain of the first strand, and a second 3' subdomain complementary to the 5' domain of the first strand, wherein the loop domain is flanked by a fluorescent molecule and a quencher molecule, and binding of the 5' domain of the second strand to the first 3' subdomain of the second strand quenches fluorescent signal emitted by the fluorescent molecule (see, e.g., FIG. 10B (middle)).

In some embodiments, a key/lock system (including compositions, kits, and/or methods) includes (a) a first nucleic acid strand comprising a 5' domain and a 3' domain, (b) a second nucleic acid strand comprising a 5' end comprising a quencher molecule, a 5' domain complementary to the 3' domain of the first strand, and a 3' domain complementary to the 5' domain of the first strand, and (c) a third nucleic acid strand comprising a domain complementary to the 5' domain of the second strand, and a 3' end comprising a fluorescent molecule, wherein binding of the second strand to the third strand quenches fluorescent signal emitted by the fluorescent molecule (see, e.g., FIG. 10B (bottom)).

Primer Exchange Reactions

During a primer exchange reaction (PER), a discrete nucleotide sequence (domain) is added (synthesized) to a "growing" nucleic acid strand, using a strand displacement polymerase and a partially-paired molecule (e.g., hairpin molecule) that acts catalytically (see, e.g., FIGS. 2A-2B). The basic primer exchange reaction occurs in three general steps. First, a primer (e.g., primer key) (domain 1) binds reversibly to a catalytic molecule (e.g., hairpin molecule), which facilitates elongation. Then, a strand displacement polymerase extends the primer to copy the stem sequence (domain 2') in the catalytic molecule, until a stop sequence (or other molecule that terminates polymerization) is reached. After elongation has terminated, the displaced stem region of the molecule can re-hybridize with its opposing strand on the molecule to displace the primer sequence to a point that it can spontaneously dissociate from the catalytic molecule and is free to interact with another cognate catalytic molecule in solution. This primer exchange reaction is capable of appending sequences onto growing strands in a specific, programmable manner, to produce, for example, a trigger key. These reactions all operate isothermally and are powered by dNTPs in solution. Primer exchange reactions can easily be connected together by having the output primer sequence of one molecular-catalyzed reaction serve as the input primer to another one. Primer exchange reactions are described in U.S. Provisional Application No. 62/296,310, filed Feb. 17, 2016 and U.S. Provisional Application No. 62/299,206, filed Feb. 24, 2016, each of which is incorporated by reference herein in its entirety.

In some embodiments, extension of a primer key by a displacing polymerase is terminated by the presence of a molecule or modification in the catalytic molecule that terminates polymerization. Thus, in some embodiments, catalytic molecules of the present disclosure comprise a molecule or modification that terminates polymerization. A molecule or modification that terminates polymerization ("stopper") is typically located in a paired domain (e.g., stem domain) of a catalytic molecule such that polymerization terminates extension of the primer through the paired domain. For catalytic molecules arranged in the form of a hairpin, a molecule or modification that terminates polymerization may be located between the paired stem domain and the loop domain. In some embodiments, the molecule that terminate polymerization is a synthetic non-DNA linker, for example, a triethylene glycol spacer, such as the Int Spacer 9 (iSp9) or Spacer 18 (Integrated DNA Technologies (IDT)). It should be understood that any non-native linker that terminates polymerization by a polymerase may be used as provided herein. Other non-limiting examples of such molecules and modifications include a three-carbon linkage (/iSpC3/) (IDT), ACRYDITE™ (IDT), adenylation, azide, digoxigenin (NHS ester), cholesteryl-TEG (IDT), I-LINKER™ (IDT), and 3-cyanovinylcarbazole (CNVK) and variants thereof. Typically, but not always, short linkers (e.g., iSp9) lead to faster reaction times.

In some embodiments, the molecule that terminates polymerization is a single or paired non-natural nucleotide sequence, such as iso-dG and iso-dC (IDT), which are chemical variants of cytosine and guanine, respectively. Iso-dC will base pair (hydrogen bond) with Iso-dG but not with dG. Similarly, Iso-dG will base pair with Iso-dC but not with dC. By incorporating these nucleotides in a pair on opposite sides of the hairpin, at the stopper position, the polymerase will be halted, as it does not have a complementary nucleotide in solution to add at that position.

In some embodiments, the efficiency of performance of a "stopper" modification is improved by lowering dNTP concentrations (e.g., from 200 µM) in a reaction to 100 µM, 10 µM, 1 µM, or less.

Inclusion of a molecule or modification that terminates polymerization often creates a "bulge" in a paired domain of catalytic molecule (e.g., a stem domain for hairpin structures), because the molecule or modification is not paired. Thus, in some embodiments, catalytic molecules are designed to include, opposite the molecule or modification, a single nucleotide (e.g., thymine), at least two of same nucleotide (e.g., a thymine dimer (TT) or trimer (TTT)), or an non-natural modification.

A complete "step" of a primer exchange reaction is depicted in FIG. 2A. An primer key ("1") binds to a toehold domain ("1'") of a catalytic molecule to start the primer exchange reaction. Upon binding to the catalytic molecule in reaction solution containing polymerase (e.g., strand displacing polymerase) and dNTPs, the primer key is extended through the paired domain, displacing a subdomain ("2") of the paired domain. The displaced subdomain ("2") then competes with the extended primer ("1+2") for binding (reannealing) with its complementary subdomain ("2'"), thereby displacing the extended output primer "1+2". This completes a step of the primer exchange reaction. The displaced output primer "1+2" may then go on to function as an input primer in the next step of the reaction.

For example, as shown in FIG. 2B, the displaced output primer "1+2," in another step of a primer exchange reaction, serves as an input primer, binding through its primer domain "2" to the toehold domain "2'" of another catalytic molecule, thereby initiating another step in the primer exchange reaction. Upon binding to the catalytic molecule in reaction solution containing polymerase and dNTPs, input primer "1+2" is extended through the paired domain, displacing a subdomain ("3'") of the paired domain. The displaced subdomain ("3") then competes with the extended primer ("1+2+3") for binding (reannealing) with its complementary subdomain ("3'"), thereby displacing the extended output primer "1+2+3". This completes another step of the primer exchange reaction. The displaced output primer "1+2+3" may then go on to function as an input primer in the next step of the reaction.

Primer exchange reactions require the use of a polymerase. In some embodiments, the polymerase is a DNA polymerase (DNAP), such as a DNA polymerase having DNA strand displacement activity (a strand displacement polymerase). "Strand displacement" describes the ability to displace downstream DNA encountered during synthesis. Examples of polymerases having DNA strand displacement activity that may be used as provided herein include, without limitation, phi29 DNA polymerase (e.g., NEB #M0269), Bst DNA polymerase, large fragment (e.g., NEB #M0275), or Bsu DNA polymerase, large fragment (e.g., NEB #M0330). Other polymerases having strand displacement activity may be used. In some embodiments, the polymerase is a RNA polymerase.

In some embodiments, the polymerase is phi29 DNA polymerase. In such embodiments, the reaction conditions may be as follows: 1× reaction buffer (e.g., 50 mM Tris-HCl, 10 mM $MgCl_2$, 10 mM $(NH_4)_2SO_4$, 4 mM DTT) supplement with purified bovine serum albumin (BSA), pH 7.5, incubated at 30° C.

In some embodiments, the polymerase is Bst DNA polymerase, large fragment. In such embodiments, the reaction conditions may be as follows: 1× reaction buffer (e.g., 20 mM Tris-HCl, 10 mM $(NH_4)_2SO_4$, 10 mM KCl, 2 mM $MgSO_4$, 0.1% TRITON® X-100), pH 8.8, incubated at 65° C.

In some embodiments, the polymerase is Bsu DNA polymerase. In such embodiments, the reaction conditions may be as follows: 1× reaction buffer (e.g., 50 mM NaCl, 10 mM Tris-HCl, 10 mM $MgCl_2$, 1 mM DTT), pH 7.9, incubated at 37° C.

The concentration of primer keys, catalytic molecules and dNTPs in a primer exchange reaction system may be varied depending, for example, on the particular application and kinetics required for that particular application.

The concentration of primer key in a primer exchange reaction may be, for example, 10 nM to 1000 nM. In some embodiments, the primer key concentration in a primer exchange reaction is 10-20, 10-30, 10-40, 10-50, 10-60, 10-70, 10-80, 10-90, 10-100, 10-125, 10-150, 10-200, 25-50, 25-75, 25-100, 25-150, 25-200, 50-75, 50-100, 50-150 or 50-200 nM. In some embodiments, the primer key concentration in a primer exchange reaction is 100-200, 100-300, 100-400, 100-500, 100-600, 100-70, 100-800, 100-900 or 100-1000 nM. In some embodiments, the primer key concentration in a primer exchange reaction is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the primer key concentration in a primer exchange reaction is 100, 200, 300, 400, 500, 600, 700, 800, 900 or 1000 nM. The concentration of primer key in a primer exchange reaction may be less than 10 nM or greater than 1000 nM.

The concentration of catalytic molecules (e.g., catalytic hairpins) in a primer exchange reaction may be, for example, 5 nM to 1000 nM. In some embodiments, the catalytic molecule concentration in a primer exchange reaction is 5-10, 5-20, 5-30, 5-40, 5-50, 5-60, 5-70, 5-80, 5-90, 5-100, 5-125, 5-150, 5-200, 10-50, 10-75, 10-100, 10-150, 10-200, 25-75, 25-100, 25-125 or 25-200 nM. In some embodiments, the catalytic molecule concentration in a primer exchange reaction is 10-200, 10-300, 10-400, 10-500, 10-600, 10-70, 10-800, 10-900 or 10-100 nM. In some embodiments, the catalytic molecule concentration in a primer exchange reaction is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the catalytic molecule concentration in a primer exchange reaction is 10, 20, 30, 40, 50, 60, 70, 80, 90 or 100 nM. The concentration of catalytic molecule in a primer exchange reaction may be less than 5 nM or greater than 1000 nM.

The ratio of primer to catalytic molecule in primer exchange reaction may be 2:1 to 100:1. In some embodiments, the ratio of primer to catalytic molecule is 2:1, 3:1, 4:1, 5:1, 6:1, 7:1, 8:1, 9:1, 10:1, 11:1, 12:1, 13:1, 14:1, 15:1, 16:1, 17:1, 18:1, 19:1 or 20:1. In some embodiments, the ratio of primer to catalytic molecule is 30:1, 40:1, 50:1, 60:1, 70:1, 80:1 or 90:1.

The number of different catalytic molecules in a primer exchange reaction in non-limiting. A primer exchange reaction may comprise 1-$10^{10}$ different catalytic molecules (each with a specific toehold domain sequence, for example). In some embodiments, a primer exchange reaction comprises 1-10, 1-$10^2$, 1-$10^3$, 1-$10^4$, 1-$10^5$, 1-$10^6$, 1-$10^7$, 1-$10^8$, 1-$10^9$, 1-$10^{10}$, or more, different catalytic molecules. In some embodiments, a primer exchange reaction comprises 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 10-15, 10-20, 10-25, 10-30, 10-35, 10-40, 10-45, 10-50, 10-55, 10-60, 10-65, 10-70, 10-75, 10-80, 10-85, 10-90, 10-95 or 10-100 different catalytic molecules. In some embodiments, a primer exchange reaction comprises 1, 2, 3, 4, 5, 6, 7, 8, 9, 10, 11, 12, 13, 14, 15, 16, 17, 28, 19, 20, 21, 22, 23, 24 or 25 different catalytic molecules. Catalytic molecules are different from each other if their toehold domains differ from each other, for example.

The kinetics of a primer exchange reaction may be controlled by varying temperature, time, buffer/salt conditions, and deoxyribonucleotide triphosphate (dNTP) concentrations, for example. Polymerases, like most enzymes, are sensitive to many buffer conditions, including ionic strength, pH and types of metal ions present (e.g., sodium ions vs. magnesium ions). Thus, the temperature at which a primer exchange reaction is performed may vary from, for example, 4° C. to 65° C. (e.g., 4° C., 25° C., 37° C., 42° C. or 65° C.). In some embodiments, the temperature at which a primer exchange reaction is performed is 4-25° C., 4-30° C., 4-35° C., 4-40° C., 4-45° C., 4-50° C., 4-55° C., 4-60° C., 10-25° C., 10-30° C., 10-35° C., 10-40° C., 10-45° C., 10-50° C., 10-55° C., 10-60° C., 25-30° C., 25-35° C., 25-40° C., 25-45° C., 25-50° C., 25-55° C., 25-60° C., 25-65° C., 35-40° C., 35-45° C., 35-50° C., 35-55° C., 35-60° C., or 35-65° C. In some embodiments, a primer exchange reaction is performed at room temperature, while in other embodiments, a primer exchange reaction is performed at 37° C.

A primer exchange reaction may be performed (incubated) for 30 minutes (min) to 24 hours (hr). In some embodiments, a primer exchange reaction is carried out for 10 min, 35 min, 40 min, 45 min, 50 min, 55 min, 60 min, 1 hr, 2 hr, 3 hr, 4 hr, 5 hr, 6 hr, 7 hr, 8 hr, 9 hr, 10 hr, 11 hr, 12 hr, 18 hr or 24 hr.

Deoxyribonucleotides (dNTPs) are the "fuel" that drives a primer exchange reaction. Thus, the kinetics of a primer exchange reaction, in some embodiments, depends heavily on the concentration of dNTPs in a reaction. The concentration of dNTPs in a primer exchange reaction may be, for example, 2-1000 µM. In some embodiments, the dNTP concentration in a primer exchange reaction is 2-10 µM, 2-15 µM, 2-20 µM, 2-25 µM, 2-30 µM, 2-35 µM, 2-40 µM, 2-45 µM, 2-50 µM, 2-55 µM, 2-60 µM, 2-65 µM, 2-70 µM, 2-75 µM, 2-80 µM, 2-85 µM, 2-90 µM, 2-95 µM, 2-100 µM, 2-110 µM, 2-120 µM, 2-130 µM, 2-140 µM, 2-150 µM, 2-160 µM, 2-170 µM, 2-180 µM, 2-190 µM, 2-200 µM, 2-250 µM, 2-300 µM, 2-350 µM, 2-400 µM, 2-450 µM, 2-500 µM, 2-600 µM, 2-700 µM, 2-800 µM, 2-900 µM or 2-1000 µM. For example, the dNTP concentration in a primer exchange reaction may be 2 µM, 5 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 105 µM, 110 µM, 115 µM, 120 µM, 125 µM, 130 µM, 135 µM, 140 µM, 145 µM, 150 µM, 155 µM, 160 µM, 165 µM, 170 µM, 175 µM, 180 µM, 185 µM, 190 µM, 195 µM or 200 µM. In some embodiments, the dNTP concentration in a primer exchange reaction is 10-20 µM, 10-30 µM, 10-40 µM, 10-50 µM, 10-60 µM, 10-70 µM, 10-80 µM, 10-90 µM or 10-100 µM.

In some embodiments, dNTP variants are used. For example, primer exchange reactions may use hot start/clean amp dNTPs, phosphorothioate dNTPs, or fluorescent dNTPs. Other dNTP variants may be used. Because some modified dNTPs are less favorable than normal (unmodified) DNA-DNA binding, the hairpin back displacement process may be increased with their usage. Similarly, a hairpin comprised of a different type of nucleic acid (e.g., LNA, RNA or interspersed modified bases such as methyl dC or super T IDT modifications) may be used in some embodiments to increase the speed of a PER by forming stronger bonds than the synthesized primer with respect to the catalytic molecule.

Toehold Switch Locks

Riboregulator switches generally. Toehold switch locks are riboregulator switches, which are typically RNA molecules that can be used to control translation of an open reading frame and thus production of a protein. The switch forms through complementary base pairing a hairpin comprising a stem domain and a loop domain. The hairpin blocks access to the RNA transcript by the ribosome, thereby preventing translation. The hairpin typically sequesters a ribosome binding site (RBS) in its stem domain or its loop domain.

The alteration in the hairpin domain that occurs upon binding of a trigger nucleic acid (e.g., trigger key) to the switch allows the ribosome to gain access to the region of the transcript upstream of the start codon, thereby releasing the switch from its repressed state and facilitating protein translation from the transcript. The switches are typically engineered RNA molecules and/or are produced by engineered DNA sequences. The triggers may also be engineered nucleic acids.

Further general teachings relating to riboregulator switches are found in published International PCT Application Nos. WO 2004/046321, WO 2014/074648 and WO2016/011089, the content of each of which is incorporated by reference herein.

Toehold Switch Lock. In a toehold switch lock system, the interaction between the switch and the trigger is mediated through an unpaired (single-stranded) nucleic acid domain that is located to the 5' end of the hairpin. This unpaired nucleic acid domain, which is referred to as the toehold domain, provides the trigger with sufficient binding affinity to enable it to unwind the stem domain of the hairpin. Thus, also provided herein are toehold riboregulator switches (toehold switch locks) comprising an RNA comprising (a) an unpaired toehold domain that comprises a sequence complementary to the 3' subdomain of one of the catalytic molecules, (b) a hairpin comprising (i) a paired stem domain comprising an initiation codon located 3' of the unpaired toehold domain and a sequence complementary to the 3' toehold domain of one of the catalytic molecules, and (ii) a loop domain comprising a ribosome binding site, and (c) a coding domain encoding a reporter protein. Typically, the coding domain encodes a reporter protein (e.g., green fluorescent protein, GFP).

The degree of complementarity between a trigger key and the toehold domain may vary. In some embodiments, it is at least 60%, at least 70%, at least 80%, at least 90%, at least 95%, or 100%. For optimal riboregulator kinetics, the trigger key should possess minimal secondary structure and full complementarity (i.e., 100%) to the toehold domain of the toehold switch lock. As used herein, secondary structure refers to non-linear structures including for example hairpin structures, stem loop structures, and the like. Accordingly, in some embodiments, the trigger includes (e.g., consists of) a sequence with little to no probability of forming secondary structure under the conditions of its use. Those of ordinary skill in the art are able to determine such sequences either manually or through the use of computer programs available in the art.

In some embodiments, the toehold switch lock comprises more than one coding domain, and thus encodes more than one protein. The coding domains may be arranged in linear manner downstream (3') of the hairpin domain.

The unpaired toehold domain, in some embodiments, may be complementary to a primer key or a toehold or stem domain of a catalytic nucleic acid molecule (e.g., a catalytic hairpin molecule).

The length of a toehold domain of a toehold switch lock may vary. In some embodiments, a toehold domain may have a length of 2-35, 2-30, 2-25, 2-20, 2-15, 2-10, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a toehold domain has a length of 5, 10, 15, 20, 25, 30, 35 or 40 nucleotides. In some embodiments, a toehold domain has a length of 10, 11, 12, 13, 14, 15, 16, 17, 18, 19, 20, 21, 22, 23, 24 or 25 nucleotides. A toehold domain, in some embodiments, is longer than 40 nucleotides, or shorter than 5 nucleotides. In some embodiments, an unpaired toehold domain has a length of 15, 16, 17, 18 nucleotides, or longer.

In some embodiments, the fully or partially paired stem domain is a partially paired stem domain, wherein the initiation codon is located in an unpaired bulge that separates first and second paired domains. In some embodiments, the first paired domain is adjacent to the toehold domain. In some embodiments, the loop domain is adjacent to the second paired domain.

The fully or partially paired stem domain may comprise one or more additional unpaired bulges, and such bulges may have a length of 1, 2 or 3 nucleotides, although they are not so limited.

In some embodiments, the initiation codon is wholly or partially present in an unpaired bulge in the stem domain.

In some embodiments, sequence downstream of the initiation codon does not encode a stop codon.

In some embodiments, the first paired domain may have a length of 11-100, 11-50, 11-40, 11-30, or 11-20 nucleotide base pairs. In some embodiments, the first paired domain may have a length of 11, 12, 13, 14, 15, 16, 17, 18, 19, 20, 21, 22, 23, 24, 25, 26, 27, 28, 29, 30 base pairs, or longer. In some embodiments, the first paired domain may have a length longer than 100 base pairs, including for example up to 120, 140, 160, 180, or 200 or more base pairs.

The length of a paired stem domain of a toehold switch lock may vary. In some embodiments, a paired domain has a length of 5-40 nucleotides. For example, a paired domain may have a length of 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a paired domain has a length of 5, 10, 15, 20, 25, 30, 35 or 40 nucleotides. In some embodiments, a paired domain has a length of 10, 11, 12, 13, 14, 15, 16, 17, 18, 19, 20, 21, 22, 23, 24 or 25 nucleotides. A paired domain, in some embodiments, is longer than 40 nucleotides, or shorter than 5 nucleotides.

A paired stem domain may have a first paired domain (subdomain) and a second paired domain (subdomain). In some embodiments, the first paired domain has a length of 11 or 12 bases pairs. In some embodiments, the first paired domain is longer than the second paired domain. In some embodiments, the second paired domain has a length of less than 11 base pairs. In some embodiments, the second paired domain has a length of 10, 9, 8, 7, or 6 base pairs. In some embodiments, the second paired domain has a length of 5 or 6 base pairs. In some embodiments, the first paired domain as a length of 11 base pairs and the second paired domain has a length of 5 base pairs. In some embodiments, the first paired domain has a length of 12 base pairs and the second paired domain has a length of 6 base pairs. In some embodiments, the loop domain has a length of 12-14 nucleotides, although it is not so limited.

In some embodiments, the toehold switch lock further comprises a spacer domain located downstream (3') of the hairpin and between the stem domain and/or the first paired domain and the coding domain. In some embodiments, the spacer domain encodes low molecular weight amino acids. In some embodiments, the spacer domain has a length of about 9-33 nucleotides, or about 21 nucleotides.

Toehold switch locks typically do not sequester the RBS within their stem domain. Instead, RBS are confined to the loop domain formed by the repressing stem domain. This allows the region immediately before (upstream or 5') and after (downstream or 3') the initiation codon to be sequestered within the stem domain, thus frustrating translation initiation. The respective lengths of the toehold, stem, and loop domains can be changed to a large extent without affecting the performance of the toehold switch lock as will be detailed below. In addition, the stem domain can retain its repression efficiency even if it contains a number of bulges or mispaired bases, which enables triggers that do not contain the start codon AUG sequence to trigger the toehold switch lock. In principle, the tolerance of bulges enables arbitrary nucleic acid sequences, including endogenous RNAs, to act as triggers into the toehold switch lock, although other criteria such as high secondary structure can affect the response of the regulator.

An exemplary, non-limiting, class of toehold switch locks possesses a toehold domain that is about 12-nucleotides (nts) long and a loop domain that is about 11-nts long and that contains, optionally at its 3' end, an RBS sequence AGAG-GAGA. Immediately adjacent to this loop domain is a stem domain comprising a 6-bp duplex spacer region and a 9-bp duplex region flanking a start codon (AUG). The 9-nts downstream (3') of the start codon were programmed to ensure they did not code for any stop codons since this would lead to early termination of translation. As will be understood based on this disclosure, the trigger is responsible for unwinding the stem domain. In addition, the 3-nt region opposite the start codon triad was completely unpaired leading to a stem domain having a 3-nt long bulge. (This design precludes a trigger from having an AUG sequence at positions programmed to hybridize to this bulge.) To reduce the likelihood that the 9-nt duplex region codes for amino acids that affect folding of the protein of interest, a common 21-nt (7-amino-acid) spacer domain containing a number of low molecular weight residues was inserted between the stem domain and the coding domain (e.g., the domain coding the protein of interest). Thus, in some instances, the toehold switch locks add 11 residues to the N-terminus of the encoded protein, which includes the 12-nt translated portion of the stem and the common 21-nt linker region immediately thereafter.

It is to be understood that this embodiment is non-limiting and that other toehold switch locks of differing lengths and functions are encompassed by this disclosure. Thus, the length of the toehold domain, the stem domain, the loop domain and the linker domain, as well as the duplex regions within the stem domain may differ in length from this embodiment.

It is to be understood that the aforementioned conditions imposed on the trigger key and effector protein can be avoided with a few modifications to the toehold switch design. The sequence constraints on the trigger key are a byproduct of the base-pairing conditions specified for the stem domain and the trigger-toehold domain complex. However, these particular secondary structures are not strictly required for switch operation. High performance switches may have less than a 3-nt bulge at the AUG position or an additional base pair at the base of the stem domain. Design modifications that add and subtract base pairs from the switch will still allow the toehold switches to modulate protein translation while simultaneously providing sufficient design flexibility to eliminate the stop-codon- and AUG-bulge-related constraints on the trigger sequence.

The toehold switch, in some instances, comprise a consensus prokaryotic RBS. However, any of a variety of alternative naturally occurring or engineered sequences may be used as the RBS. The sequences of a large number of bacterial RBS have been determined, and the important features of these sequences are known. Preferred RBS sequences for high level translation contain a G-rich region at positions −6 to −11 with respect to the AUG and typically contain an A at position −3. Exemplary RBS sequences include, but are not limited to, AGAGGAGA (or subsequences of this sequence, e.g., subsequences at least 6 nucleotides in length, such as AGGAGG). Shorter sequences are also acceptable, e.g., AGGA, AGGGAG, GAGGAG, etc. Numerous synthetic RBSs have been created, and their translation initiation activity has been tested. The activity of any candidate sequence to function as an RBS may be tested using any suitable method. For example, expression may be measured as described in Example 1 of published PCT application WO 2004/046321, or as described in reference 53 of that published PCT application, e.g., by measuring the activity of a reporter protein encoded by an mRNA that contains the candidate RBS appropriately positioned upstream of the AUG. Preferably an RBS sequence supports translation at a level of at least 10% of the level at which the consensus RBS supports translation (e.g., as measured by the activity of a reporter protein). For example, if the candidate RBS is inserted into a control plasmid in place of the consensus RBS, the measured fluorescence will be at least 10% of that measured using the consensus RBS. In some embodiments, an RBS that supports translation at a level of at least 1%, 5%, 10%, 20%, 30%, 40%, 50%, 60%, 70%, 80%, 90%, or more relative to the level at which the consensus RBS supports translation may be used. In some embodiments, an RBS that supports translation at higher levels than the consensus RBS may be used.

Moreover, the toehold switch locks can also be modified to incorporate the coding sequence of the output protein directly into the switch stem domain. Switches of this type would be compatible with any protein sensitive to N-terminal modifications. The specificity of toehold-mediated interactions, redistribution of bulges in the stem domain, and the use of synonymous codons provide sufficient sequence space for these toehold switches to operate with high dynamic range and orthogonality.

In some instances, a toehold domain having a length of at least 5 or 6 nucleotides is used for initial trigger binding. The toehold domain is therefore, in some embodiments, 5, 6, 7, 8, 9, 10, 11, 12, 13, 14, 15, 16, 17, 18, 19, 20, or more nucleotides. Moreover, it was also found that a trigger key need only unwind two-thirds of the stem domain (or two thirds of the first double stranded region of the stem domain) in order to allow translation of the encoded protein. Based on these findings, the stem domain may be as small as 12 nucleotide base pairs for adequate repression. The stem domain may however be longer than 12 nucleotide base pairs, including 13, 14, 15, 16, 17, 18, 19, 20, or more base pairs. Furthermore, expanding the loop length to 12-nts and replacement of the RBS with a slightly stronger version with the canonical Shine-Dalgarno sequence did not decrease the degree of repression by the switch. Accordingly, the length of the loop domain may be 11, 12, 13, 14, 15, 16, 17, 18, 19, 20 or more nucleotides.

Toehold switch locks may have additional features. In some instances, the top three bases of the stem domain may be A-U base pairs. In some instances, the bottom three base pairs of the stem domain may comprise two strong G-C base pairs and one A-U base pair. In some instances, the length of the switch toehold may range from about 12- to about 15-nts. This latter feature may in some instances strengthen the initial binding between a trigger and its cognate toehold domain. In some instances, the size of the loop domain may range from about 11- to about 15-nts to enhance translation of the effector protein upon switch activation. In some instances, the loop size is 15-nts. In yet other instances, a cognate trigger may be used that unwinds the first 15 of the 18 bases in the stem domain. In some instances, one or more, including all, of these features may be used simultaneously.

A trigger key, which may be an RNA, and a toehold switch lock are cognates if they are able to bind to each other and effect structural and functional changes to the toehold switch lock, but are not able to bind to other triggers and toehold switch lock with the same structural and functional effect. In some embodiments, the trigger key may be comprised of one or more domains, with at least one domain being 100% complementary to the toehold domain of the toehold switch lock or able to hybridize under stringent conditions to the toehold domain of the toehold switch lock. Thus, the triggers and toehold switch locks are specific for each other, intending that they bind to each other specifically and selectively, and not to other non-cognate nucleic acids.

It will be understood in the context of this and other embodiments provided herein the terms switches, toehold switches, toehold riboregulators, toehold riboregulator switches, riboregulator switches, toehold repressors, crRNA, crRNA riboregulators, crRNA repressors, and the like are used interchangeably. Similarly, in the context of this and other embodiments provided herein, the terms input and trigger/trigger key and the like refer to the nucleic acid that binds to a toehold switch locks, typically at its toehold domain, in whole or in part, and/or which binds to other input (e.g., primer key) or trigger keys thereby forming a nucleic acid complex that binds to a toehold domain of a toehold switch lock and effects a change in the lock structure and/or function. The latter category of inputs include those that contribute to an AND gate. Thus, an AND gate, in some embodiments, involves two or more trigger keys that must hybridize to each other to form a complex that itself is capable of binding to the toehold riboregulator switch and causing structural and functional changes to the riboregulator switch. Some but not all such AND gate triggers may comprise nucleotide sequence that is complementary and capable of hybridizing to the toehold domain of the riboregulator switch.

In some embodiments, the ratio of toehold switch lock to trigger key is less than 1, less than 0.5, or less than 0.1.

In some embodiments, the toehold switch lock is comprised or encoded in a first nucleic acid. In some embodiments, the first nucleic acid is a first plasmid. In some embodiments, the first plasmid comprises a medium copy origin of replication. The plasmids may be DNA plasmids or RNA plasmids. It will be understood that upon transcription of the DNA plasmid, the resultant RNA species will include the toehold switch lock in RNA form.

It will be further understood that any given nucleic acid construct, whether DNA or RNA in nature, such as but not limited to a plasmid or an expression vector, may comprise or encode one or more toehold switch locks.

Encoded proteins. The switch may encode one or more than one detectable molecule (e.g., a molecule that emits a detectable signal, such as a fluorescent or chemiluminescent signal), such as a reporter protein (e.g., fluorescent protein). As used herein, an encoded protein encompasses proteins and peptides, although reference will be made to proteins herein for brevity. It is to be understood that proteins and peptides are equally encompassed by the present disclosure unless stated otherwise. The presence of a reporter in a cell or organism is readily observed.

A reporter protein refers to a protein that can be used to measure gene expression and generally produce a measurable signal such as fluorescence, luminescence or color. For example, fluorescent proteins (e.g., GFP) cause a solution (or other medium) to fluoresce when excited with light of a particular wavelength, luciferases cause a catalytic reaction that produces light, and enzymes such as β-galactosidase convert a substrate to a colored product.

In some embodiments, a reporter protein is a fluorescent protein. Fluorescence can be readily quantified using a microscope, plate reader, flow cytometer or other device (e.g., handheld device) equipped to excite the fluorescent protein with the appropriate wavelength of light. Several different fluorescent proteins are available. Examples of genes encoding fluorescent proteins that may be used in accordance with the present disclosure include, without limitation, those proteins provided in U.S. Patent Application No. 2012/0003630 (see Table 59), incorporated herein by reference.

In some embodiments, a reporter protein is a luciferase. Luminescence can be readily quantified using a plate reader or luminescence counter. Examples of genes encoding luciferases for that may be used in accordance with the present disclosure include, without limitation, dmMyD88-linker-Rluc, dmMyD88-linker-Rluc-linker-PEST191, and firefly luciferase (from *Photinus pyralis*).

Logic Solutions

In some embodiments, logical operations are used to unlock a toehold switch lock. For example, a toehold switch lock may be opened only in the presence of primer key A but not in the presence of primer key B. Other, more complex logic operations are encompassed herein. For example, a toehold switch lock may be opened only if two primer keys are present, but not a third primer key (see, e.g., FIGS. 6A-6D).

Boolean logic function is based on logic gates that can be used to assemble combinations of functions that will implement any digital component. There are at least sixteen logic gates: NOT, AND, OR, NOT, NOR, NAND, XOR, XNOR, A IMPLY B, B IMPLY A, A NIMPLY B, B NIMPLY A, A, B, FALSE or TRUE.

Use in Drug Authentication Procedures

In some applications, such as prescription drug authentication and tracking, it may be preferable that the DNA keys not be modified out of regulatory and safety concerns. Unmodified DNA keys can be used by changing the key sequence frequently, in order to protect against key reading and counterfeiting.

Figure 20A:
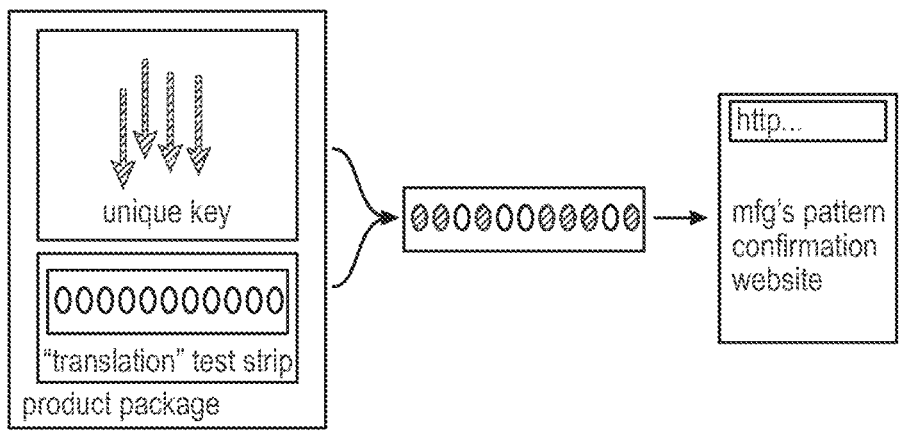
FIGS. 20A-20B show examples of the lock and key system using unmodified key strands described in Example 11.

In one embodiment, shown in FIG. 20A, each product contains a unique key strand. The product further includes the test strip, which translates the product key into a visible code. Application of the product to the test strip results in a long and unique barcode pattern. The pattern is checked on the manufacturer's web site for authenticity, for example, with a phone camera, manual input, or other method. Each test strip result can be checked only once because repeat testing or a wrong key will result in a negative result that indicates likely forgery. Diluting a real product into several copied products is also protected against. This application also does not necessarily require that lock strands are protected against reading.

Figure 20B:
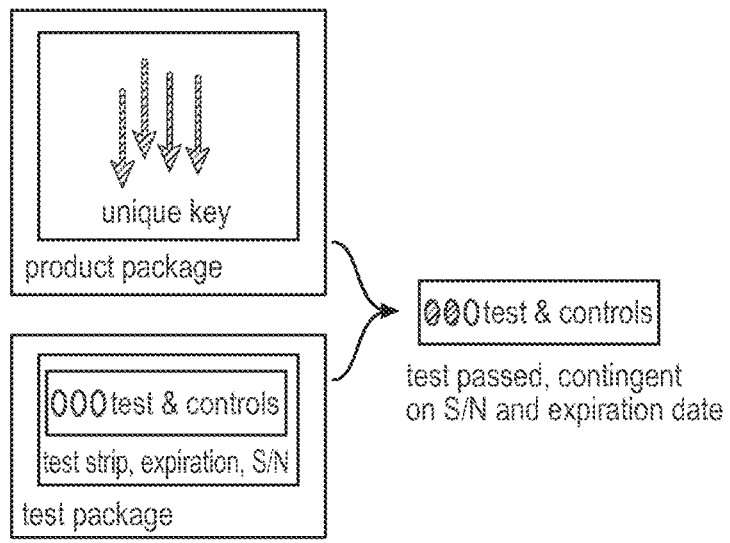

In another embodiment, depicted in FIG. 20B, a given key sequence is used for a short period of time, for example, when a specific unmodified DNA strand is mixed within a liquid or solid drug formulation. The paper-based test, received from a separate source (the legitimate drug manufacturer) on a separate occasion, allows for authentication of the specific key. The test strip is marked with an expiration date, after which it is no longer valid, as well as a range of serial numbers or other batch numbers with which the test is compatible. In some embodiments, the lock strands are protected from reading by covalent modification or other. As an added level of protection, when the test strip expires, the manufacturer changes the incorporated key strand, so that reading the key strands from current drug batches is only profitable for the very short term.

Nucleic Acids

It should be understood that the nucleic acids of the present disclosure do not occur in nature. Thus, the nucleic acids may be referred to as "engineered nucleic acids." An "engineered nucleic acid" is a nucleic acid (e.g., at least two nucleotides covalently linked together, and in some instances, containing phosphodiester bonds, referred to as a phosphodiester "backbone") that does not occur in nature. Engineered nucleic acids include recombinant nucleic acids and synthetic nucleic acids. A "recombinant nucleic acid" is a molecule that is constructed by joining nucleic acids (e.g., isolated nucleic acids, synthetic nucleic acids or a combination thereof) and, in some embodiments, can replicate in a living cell. A "synthetic nucleic acid" is a molecule that is amplified or chemically, or by other means, synthesized. A synthetic nucleic acid includes those that are chemically modified, or otherwise modified, but can base pair with (also referred to as "binding to," e.g., transiently or stably) naturally-occurring nucleic acid molecules. Recombinant and synthetic nucleic acids also include those molecules that result from the replication of either of the foregoing.

While an engineered nucleic acid, as a whole, is not naturally-occurring, it may include wild-type nucleotide sequences. In some embodiments, an engineered nucleic acid comprises nucleotide sequences obtained from different organisms (e.g., obtained from different species). For example, in some embodiments, an engineered nucleic acid includes a murine nucleotide sequence, a bacterial nucleotide sequence, a human nucleotide sequence, a viral nucleotide sequence, or a combination of any two or more of the foregoing sequences. In some embodiments, an engineered nucleic acid contain one or more random bases.

In some embodiments, an engineered nucleic acid of the present disclosure may comprise a backbone other than a phosphodiester backbone. For example, an engineered nucleic acid, in some embodiments, may comprise phosphoramide, phosphorothioate, phosphorodithioate, O-methylphophoroamidite linkages, peptide nucleic acids or a combination of any two or more of the foregoing linkages. An engineered nucleic acid may be single-stranded (ss) or double-stranded (ds), as specified, or an engineered nucleic acid may contain portions of both single-stranded and double-stranded sequence. In some embodiments, an engineered nucleic acid contains portions of triple-stranded sequence, or other non-Watson-Crick base pairing such as G-quartets, G-quadruplexes, and i-motifs. An engineered nucleic acid may comprise DNA (e.g., genomic DNA, cDNA or a combination of genomic DNA and cDNA), RNA or a hybrid molecule, for example, where the nucleic acid contains any combination of deoxyribonucleotides and ribonucleotides (e.g., artificial or natural), and any combination of two or more bases, including uracil, adenine, thymine, cytosine, guanine, inosine, xanthine, hypoxanthine, isocytosine and isoguanine.

Engineered nucleic acids of the present disclosure may be produced using standard molecular biology methods (see, e.g., Green and Sambrook, *Molecular Cloning*, A Laboratory Manual, 2012, Cold Spring Harbor Press). In some embodiments, nucleic acids are produced using GIBSON ASSEMBLY® Cloning (see, e.g., Gibson, D. G. et al. *Nature Methods*, 343-345, 2009; and Gibson, D. G. et al. *Nature Methods*, 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed domains. A DNA ligase then seals the nick and covalently links the DNA fragments together. The overlapping sequence of adjoining fragments is much longer than those used in Golden Gate Assembly, and therefore results in a higher percentage of correct assemblies. Other methods of producing engineered nucleic acids are known in the art and may be used in accordance with the present disclosure.

Reading Molecule Verification Systems

To output the result of the verification reaction, several readout strategies can be used. For example, the readout may be a visible color change in a solution containing components of a verification systems. This color change may be the result of protein expression encoded by a toehold switch lock that has been opened. This can be achieved, for example, by activating a toehold switch that produces a protein that causes a change in color.

Figure 16:
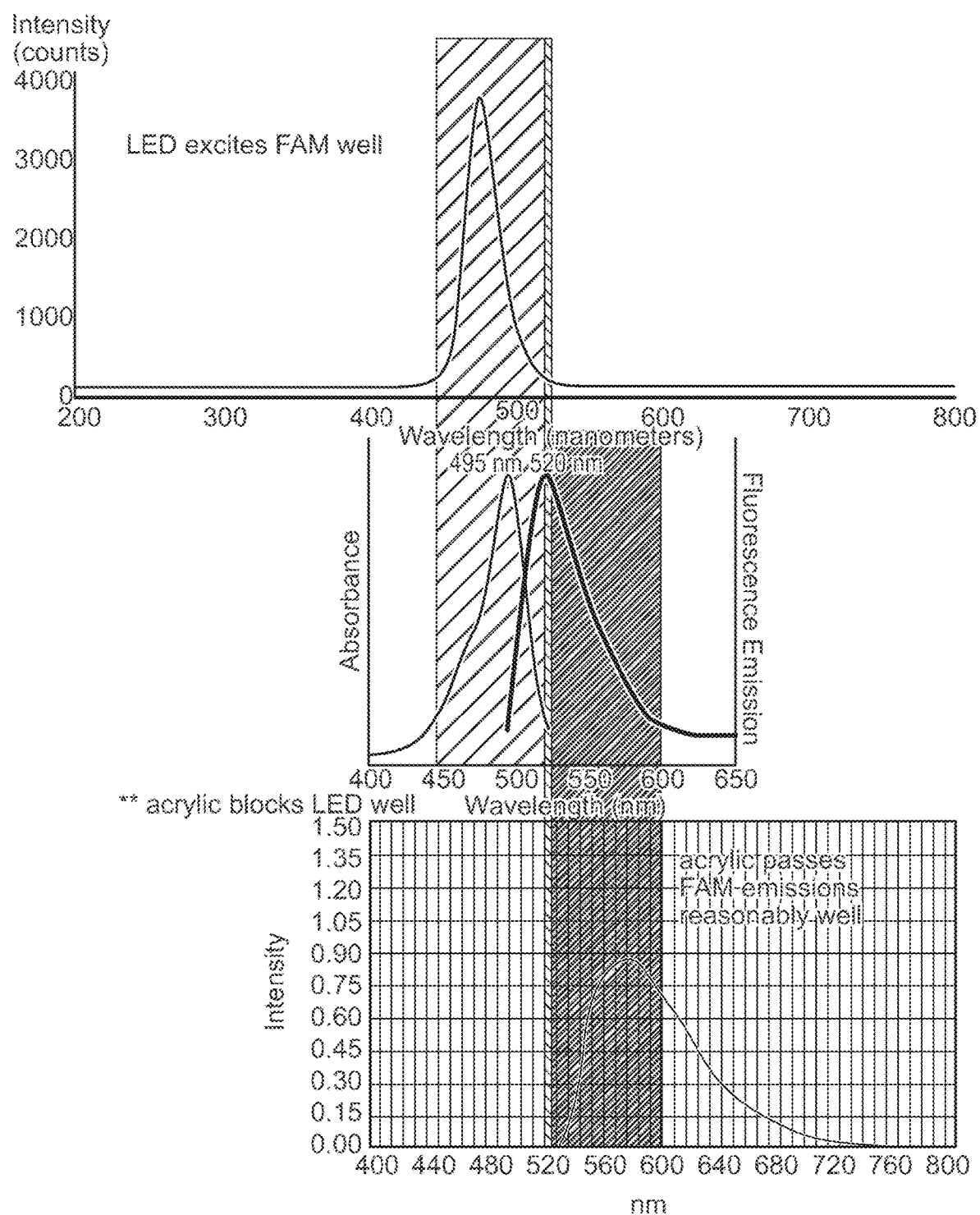
FIG. 16 shows the blue LED emission spectrum (top), FAM spectra (middle), and long-pass filter (McMaster amber acrylic transmissivity) used for the imager device described in Example 8.
Figure 17:
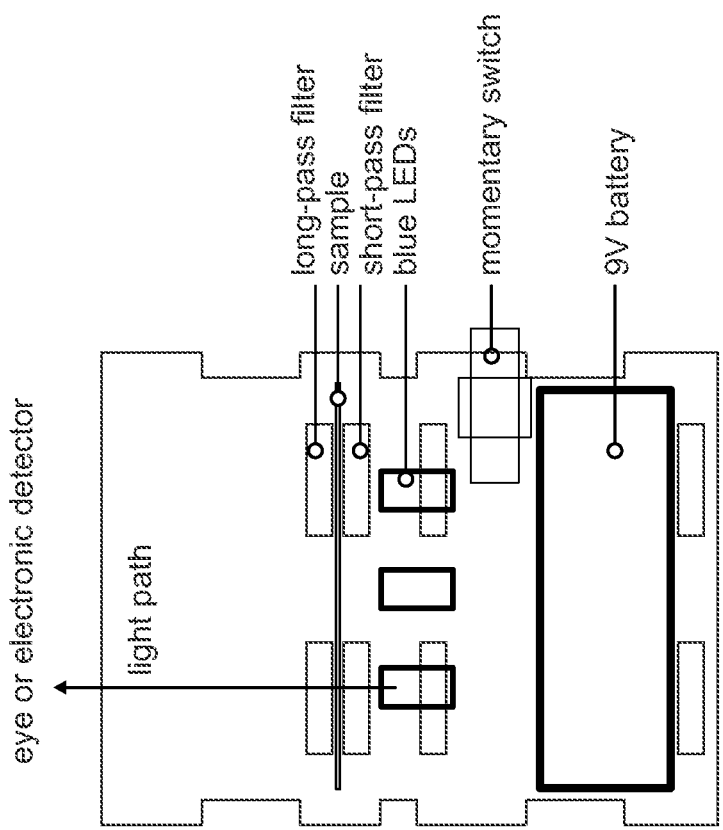
FIG. 17 shows a schematic and example of the imager device described in Example 8.

As another example, the readout may be fluorescence detected using a transilluminator, such as a blue light flashlight or other specific wavelength. For example, a primer exchange reaction may include nucleotides sequences that recruit incorporation of Thioflavin T (ThT), which fluoresces when illuminated under blue light (see, e.g., FIG. 4E). Fluorescent intercalating dyes (e.g., SYBR® Green) can also be used. Further, for the detection of certain fluorophores (for example, fluorescein), a combination of short- and long-pass optical filters may be used following blue light excitation of the substrate (see, e.g., FIG. 16). For example, a short-pass filter can be used to modify incident blue light, which is then directed to the long-pass filter (for example, the McMaster amber acrylic filter) to detect the fluorophore. An example of a handheld detector combining use of a filter unit and blue LEDs, is shown in FIG. 17.

Physical Implementation

The molecular verification systems may be implemented in one of several formats, including droplets, inks, capillary strips, or spray.

Droplets. Two solutions—one with the molecular identifiers and one with the molecular decoders—can be mixed together to initiate the decoding PER and/or toehold switch reactions. The result is read out in one of the ways described above.

Ink. Toehold switch locks can be operated on paper, for example, and dried DNA can be stored stably on paper for significant periods of time, particularly if it is lyophilized. This, therefore, makes ink, especially dried ink, an appealing mode of storage of molecular identifying and/or decoding systems. For example, a person may carry a pen containing primer keys. Alternatively, ink may be stamped or written and dried onto a piece of paper (or hand, or other surface) that can be rehydrated upon the need for verification and mixed with the appropriate molecular decoders (e.g., catalytic molecules and toehold switch locks). Similarly, the molecular decoder may be a pen that is written over a dried molecular identifying recording to verify identity by the analysis and readout strategies described above.

Capillary strip. Capillary action can be used to pull a molecular identifying solution up to a dried deposited molecular decoding solution for verification or vice versa. Strips have the added benefit of being able to easily include positive and negative control lanes to further verify no spoofing has been attempted, while still required the strip to be set in the appropriate aqueous solution only once.

Spray. Toehold switch locks can be operated on a substrate, such as paper. In some embodiments, the toehold lock(s) are deposited within a defined area or graphic design, which may be defined by a hydrophobic barrier, such as wax. The locks, which comprise fluorescent molecules that are prevented from fluorescing by quenchers, are exposed to a "key" solution through spraying. When the matching key is sprayed on the locks, the quencher is displaced from the fluorescent molecule. The graphic design can then be assayed for fluorescence.

Additional Security Measures

Several additional aspects of molecular verification systems can be used to add additional layers of security to the protocol:

Short primer keys. Short nucleic acid sequences (e.g., less than 18 nucleotides) are difficult to amplify and sequence, which makes molecular identifying solutions particularly hard to replicate (spoof).

Modified primer keys. Modifications on the primer key may be further included to inhibit the potential of replication through methods such as polymerase chain reaction (PCR).

Specific sequences of primer keys. Primer keys may be designed to have sequences that are purposefully difficult to sequence and replicate, such as a series of repeated domains.

Relative and exact concentrations. By designing molecular verification system to distinguish between solutions with the correct relative and/or exact concentrations of species in solution, additional security is achieved. Even if someone managed to sequence the species present in solution, it would be very difficult to also identify the relative and/or exact concentrations of them to effectively break the code.

Obfuscation. By including additional species, as mentioned above, correctly determining the identifying characteristics of primer keys and the decoding programs becomes significantly more difficult.

Temperature or light sensitive species. By including species that become degraded at elevated temperatures or in the presence of light, for example, the potential for someone to obtain and replicate a solution can be further protected against.

Time sensitive species. Reaction mixtures can be further protected by designing them to degrade after a certain amount of time after rehydration, which further limits the potential for someone to replicate them. These solutions are read in a timely fashion and, because of the imminent degradation, can only be read once after deposition.

Controls. Positive and negative control mechanisms can be implemented to determine if someone is trying to spoof a molecular identifying reaction mixture. For example, a reaction mixture may include a chemical that renders all toehold switches constitutively active. By including and testing with a negative control of a toehold switch that should not be activated, for example, in the presence of the cognate key, the possibility of false access is eliminated. Positive controls can be used to verify that samples are properly mixed and materials haven't expired. Positive controls are particularly easy to add to capillary strips (as dehydrated lanes) or to pens, for example, where a person can test with the reaction, as well as control pens to validate a key.

Authentication Via Nucleic Acid Nanostructure Self-Assembly

In some embodiments, a product may be authenticated by assaying for the presence of a nucleic acid nanostructure using, for example, atomic force microscopy (AFM) or electron microscopy (EM). In some embodiments, the nucleic acid nanostructure is present (e.g., attached to) the product. In other embodiments, the nucleic acid nanostructure is present on (e.g., attached to) the product packaging. In some embodiments, the product is a liquid product, such as perfume, ink or other oil-based or aqueous-based product. In some embodiments, the product is a solid. The nucleic acid nanostructure may self-assemble from DNA, RNA or a combination of DNA and RNA. In some embodiments, the nucleic acid nanostructure is assembled via a known DNA origami method. In some embodiments, the nucleic acid nanostructure is assembled via a single-stranded tile-based (SST-based) method, (see, e.g., Wei B. et al. Nature 485: 626, 2012 and International Publication Number WO 2014/074597, published 15 May 2014, International Publication Number WO 2013/022694, published Feb. 14, 2013, and International Publication Number WO 2014/018675, published Jan. 30, 2014, each incorporated by reference herein). In some embodiments, the nucleic acid nanostructure comprises a recognizable shape, e.g., letter, e.g., as described in US 2015/0218204. In some embodiments, the nucleic acid nanostructure is assembled via folding of one single strand of nucleic acid, e.g., as described in WO 2016/144755, incorporated herein by reference. In some embodiments, the nucleic acid nanostructure is assembled prior to attachment to the product and/or packaging. In other embodiments, the nucleic acid nanostructure is assembled during assembling of the product and/or packaging. Thus, in some embodiments, a method comprising visualizing presence of a particular nucleic acid nanostructure (e.g., having a defined, two- or three-dimensional shape) in a sample of a product or packaging, and authenticating the identity of the product based on the presence or absence of the nucleic acid nanostructure in the sample.

Additional Embodiments

1. A kit, comprising:
  (a) a composition comprising a set of catalytic molecules, each catalytic molecule comprising (i) an unpaired 3' toehold domain, (ii) a paired stem domain formed by intramolecular nucleotide base pairing between a 3' subdomain of the molecule and a 5' subdomain of the molecule, and optionally (iii) a loop domain;
  (b) a composition comprising a primer key that is complementary to and binds to the 3' toehold domain of one of the catalytic molecules;
  (c) a composition comprising a RNA toehold switch lock comprising
    (i) an unpaired toehold domain that comprises a sequence complementary to the 3' subdomain of one of the catalytic molecules,
    (ii) a hairpin comprising
      a paired stem domain comprising an initiation codon located 3' of the unpaired toehold domain and a sequence complementary to the 3' toehold domain of one of the catalytic molecules, and
      a loop domain comprising a ribosome binding site, and
    (iii) a coding domain encoding a reporter protein.

2. The kit of paragraph 1, wherein the key primer has a length of less than 18 nucleotides.

3. The kit of paragraph 2, wherein the key primer has a length of 4-15 nucleotides 4. The kit of any one of paragraphs 1-3, wherein the composition of (c) further comprises at least one molecule that does not bind to the catalytic hairpin molecule 5. The kit of any one of paragraphs 1-4, wherein the set of catalytic molecules comprises 3-20 catalytic molecules.

6. The kit of any one of paragraphs 1-5, wherein catalytic molecules of the set have a length of 25-100 nucleotides.

7. The kit of any one of paragraphs 1-6, wherein the toehold domain of catalytic molecules of the set has a length of 4-17 nucleotides.

8. The kit of any one of paragraphs 1-7, wherein the stem domain of catalytic molecules of the set has a length of 5-40 nucleotides.

9. The kit of any one of paragraphs 1-8, wherein the loop domain of catalytic molecules of the set has a length of 3-20 nucleotides 10. The kit of any one of paragraphs 1-9, wherein the toehold domain of the RNA toehold switch lock has a length of 5-20 nucleotides.

11. The kit of any one of paragraphs 1-10, wherein the stem domain of the RNA toehold switch lock has a length of 2-100 nucleotides.

12. The kit of any one of paragraphs 1-11, wherein the ribosome binding site of the RNA toehold switch lock comprises sequence AGAGGAGA 13. The kit of any one of paragraphs 1-12, wherein the reporter protein is a fluorescent protein.

14. A method, comprising:
combining in a first reaction buffer comprising a polymerase having strand displacement activity, and deoxyribonucleotide triphosphates (dNTPs)
  (a) a set of catalytic molecules, each catalytic hairpin molecule comprising
    (i) an unpaired 3' toehold domain, (ii) a paired stem domain formed by intramolecular nucleotide base pairing between a 3' subdomain of the molecule and a 5' subdomain of the molecule, and (iii) a loop domain; and
  (b) a primer key that is complementary to and binds to the 3' toehold domain of one of the catalytic molecules;
incubating the first reaction mixture under conditions that result in nucleic acid polymerization, strand displacement and annealing, for a time sufficient to produce a single-stranded nucleic acid trigger;
combining in a second reaction buffer
  (c) the single-stranded nucleic acid trigger, and
  (d) a RNA toehold switch lock comprising
    (i) an unpaired toehold domain that comprises a sequence complementary to the 3' subdomain of one of the catalytic molecules,
    (ii) a hairpin comprising
      a paired stem domain comprising an initiation codon located 3' of the unpaired toehold domain and a sequence complementary to the 3' toehold domain of one of the catalytic molecules, and
      a loop domain comprising a ribosome binding site, and
    (iii) a coding domain encoding a reporter protein, thereby forming a second reaction mixture; and
incubating the second reaction mixture under conditions that result in nucleic acid hybridization, RNA transcription and protein translation, for a time sufficient to express the reporter protein.

15. A kit, comprising:
  (a) a composition comprising a nucleic acid strand linked to a fluorescent molecule and having a 5' domain and a 3' domain; and
  (b) a composition comprising a nucleic acid strand linked to a quenching molecule and having (i) a 5' domain complementary to the 3' domain of the nucleic acid strand of (a) and (ii) a 3' domain complementary to the 5' domain of the nucleic acid strand of (a).

16. The kit of paragraph 15, wherein the nucleic acid strand of (a) and/or (b) comprises at least one stopper 17. The kit of paragraph 16, wherein the at least one stopper is selected from spacers, synthetic nucleotides and modified nucleotides.

18. A method, comprising:
combining in a reaction buffer comprising the composition of (a) and the composition of (b) of any one of paragraphs 15-17; and
incubating the reaction buffer under conditions that result in nucleic acid hybridization.

19. A kit, comprising:
  (a) a composition comprising a nucleic acid hairpin molecule having a loop domain and a stem domain formed by pairing of a 5' end domain and a 3' end domain of the nucleic acid molecule, wherein one end domain includes a fluorescent molecule and the other end includes a quenching molecule; and
  (b) a composition comprising a nucleic acid hairpin molecule having a loop domain and a stem domain formed by pairing of a 5' end domain and a 3' end domain of the nucleic acid hairpin molecule, wherein one end domain comprises a sequence complementary to a sequence of the 5' end domain of the hairpin molecule of (a), the other end domain comprises a sequence complementary to a sequence of the 3' end domain of the hairpin molecule of (a), and the loop domain comprises a sequence complementary to a sequence of the loop domain of (a).

20. The kit of paragraph 19, wherein the nucleic acid hairpin molecule of (a) and/or (b) comprises at least one stopper.

21. The kit of paragraph 20, wherein the at least one stopper is selected from spacers, synthetic nucleotides and modified nucleotides.

22. A method, comprising:
combining in a reaction buffer comprising the composition of (a) and the composition of (b) of any one of paragraphs 19-21; and
incubating the reaction buffer under conditions that result in nucleic acid hybridization.

23. A kit, comprising:
  (a) a composition comprising a catalytic molecule having (i) an unpaired toehold domain, (ii) a paired stem domain comprising a fluorescent molecule opposing a quenching molecule, and optionally (iii) a loop domain; and
  (b) a composition comprising a nucleic acid strand having two adjacent domains, one domain complementary to the toehold domain of the catalytic molecule of (a) and the other domain complementary to the stem domain of the catalytic molecule of (a).

24. The kit of paragraph 23, wherein the catalytic molecule of (a) and/or the nucleic acid strand of (b) comprises at least one stopper.

25. The kit of paragraph 24, wherein the at least one stopper is selected from spacers, synthetic nucleotides and modified nucleotides.

26. A method, comprising:
combining in a reaction buffer comprising the composition of (a) and the composition of (b) of any one of paragraphs 23-25; and
incubating the reaction buffer under conditions that result in nucleic acid hybridization.

27. A kit, comprising:
  (a) a first nucleic acid strand comprising a 5' domain and a 3' domain;
  (b) a second nucleic acid strand comprising a 5' domain that is complementary to the 3' domain of the first nucleic acid strand;

(c) a third nucleic acid strand comprising (i) a 5' domain that is complementary to the 3' domain of the first nucleic acid strand and (ii) a 3' domain that is complementary to the 5' domain of the first nucleic acid strand;

(d) a fourth nucleic acid strand comprising a 5' domain and a 3' domain;

(e) a fifth nucleic acid strand comprising a 5' domain that is complementary to the 3' domain of the fourth nucleic acid strand;

(f) a sixth nucleic acid strand comprising (i) a 5' domain that is complementary to the 3' domain of the fourth nucleic acid strand and (ii) a 3' domain that is complementary to the 5' domain of the fourth nucleic acid strand;

(g) quencher molecules; and (h) fluorescent molecules, wherein the 3' domain of the first nucleic acid strand and the 3' domain of the fourth nucleic acid strand have nucleotide compositions that are different from each other.

28. The kit of 27, wherein at least one of the quencher molecules is linked to the 3' domain of the first nucleic acid strand and/or is linked to the 3' domain of the fourth nucleic acid strand.

29. The kit of 27 or 28, wherein the fluorescent molecule is linked to the 5' domain of the second nucleic acid strand and/or is linked to the 5' domain of the fifth nucleic acid strand.

30. The kit of any one of paragraphs 27-29 comprising a first solution that comprises the first nucleic acid strand bound to the second nucleic acid strand.

31. The kit of any one of paragraphs 27-30 comprising a second solution that comprises the fourth nucleic acid strand bound to the fifth nucleic acid strand.

32. A solution, comprising:

(a) a first nucleic acid strand comprising a 5' domain and a 3' domain linked to a quencher molecule;

(b) a second nucleic acid strand comprising a 5' domain linked to a fluorescent molecule and bound to the 3' domain of the first nucleic acid strand;

(c) a third nucleic acid strand comprising (i) a 5' domain that is complementary to the 3' domain of the first nucleic acid strand and (ii) a 3' domain that is complementary to the 5' domain of the first nucleic acid strand;

(d) a fourth nucleic acid strand comprising a 5' domain and a 3' domain linked to a quencher molecule;

(e) a fifth nucleic acid strand comprising a 5' domain linked to a fluorescent molecule and bound to the 3' domain of the fourth nucleic acid strand; and (f) a sixth nucleic acid strand comprising (i) a 5' domain that is complementary to the 3' domain of the fourth nucleic acid strand and (ii) a 3' domain that is complementary to the 5' domain of the fourth nucleic acid strand;

wherein the 3' domain of the first nucleic acid strand and the 3' domain of the fourth nucleic acid strand have nucleotide compositions that are different from each other.

33. A substrate, comprising:

(a) at least one discrete region comprising (i) a first nucleic acid strand comprising a 5' domain and a 3' domain linked to a quencher molecule, and (ii) a second nucleic acid strand comprising a 5' domain linked to a fluorescent molecule and bound to the 3' domain of the first nucleic acid strand; and (b) at least one discrete region comprising (i) a third nucleic acid strand comprising a 5' domain and a 3' domain linked to a quencher molecule, and (ii) a fourth nucleic acid strand comprising a 5' domain linked to a fluorescent molecule and bound to the 3' domain of the third nucleic acid strand, wherein the 3' domain of the first nucleic acid strand and the 3' domain of the third nucleic acid strand have nucleotide compositions that are different from each other.

34. A method comprising:

patterning a substrate with a graphic design;

depositing onto the graphic design in a predetermined pattern at least one of:

(a) a first nucleic acid strand comprising a 5' domain and a 3' domain linked to a quencher molecule, and a second nucleic acid strand comprising a 5' domain linked to a fluorescent molecule and bound to the 3' domain of the first nucleic acid strand; and (b) a third nucleic acid strand comprising a 5' domain and a 3' domain linked to a quencher molecule, and a fourth nucleic acid strand comprising a 5' domain linked to a fluorescent molecule and bound to the 3' domain of the third nucleic acid strand.

35. The method of paragraph 34 further comprising depositing onto the graphic design at least one of:

(c) a fifth nucleic acid strand comprising (i) a 5' domain that is complementary to the 3' domain of the first nucleic acid strand and (ii) a 3' domain that is complementary to the 5' domain of the first nucleic acid strand; and (d) a sixth nucleic acid strand comprising (i) a 5' domain that is complementary to the 3' domain of the third nucleic acid strand and (ii) a 3' domain that is complementary to the 5' domain of the third nucleic acid strand.

36. The method of paragraph 35 further comprising assaying the graphic design for fluorescence.

37. The method of paragraph 36, wherein the assay comprises exposing the graphic design to a transilluminator, optionally through a filter unit.

38. The method of any one of paragraphs 34-37, wherein the substrate is paper.

39. A product authentication system comprising:

(a) a first nucleic acid comprising (i) a 5' domain and (ii) a 3' domain;

(b) a second nucleic acid comprising (i) a 5' domain complementary to the 3' domain of the first nucleic acid and (ii) a 3' domain;

(c) a third nucleic acid comprising (i) a 5' domain complementary to the 3' domain of the second nucleic acid and (ii) a 3' domain; and (d) a fourth nucleic acid comprising (i) a 5' domain complementary to the 3' domain of the third nucleic acid and (ii) a 3' domain.

40. A product authentication system comprising:

(a) a first nucleic acid comprising a first domain, a second domain, a loop domain and a fourth domain complementary to and bound to the second domain; and (b) a second nucleic acid comprising a first domain, a second domain, a loop domain and a fourth domain complementary to and bound to the second domain of the second nucleic acid, wherein the loop domain of the first nucleic acid is complementary to the loop domain of the second nucleic acid.

41. A product authentication system comprising:

(a) a first circular nucleic acid comprising a first domain and a second domain; and (b) a second circular nucleic acid comprising a first domain and a second domain, wherein the first domain of the first circular nucleic acid is complementary to the first domain of the second circular nucleic acid.

42. A product authentication system comprising:

(a) a first nucleic acid comprising a 5' domain and a 3' domain;

(b) a second nucleic acid comprising (i) a 5' domain complementary to the 3' domain of the first nucleic acid and linked to a quencher molecule and (ii) a 3' domain complementary to the 5' domain of the first nucleic acid; and (c) a third nucleic acid comprising a 3' domain complementary to the 5' domain of the second nucleic acid and linked to a fluorescent molecule.

43. A product authentication system comprising:
   (a) a first nucleic comprising a 5' domain and a 3' domain;
   (b) a second nucleic acid comprising (i) a 5' domain and (ii) a 3' domain complementary to the 5' domain of the first nucleic acid;
   (c) a third nucleic acid comprising (i) a 5' domain complementary to the 3' domain of the first nucleic acid and linked to a quencher molecule and (ii) a 3' domain complementary to the 5' domain of the second nucleic acid; and
   (d) a fourth nucleic acid comprising a 3' domain complementary to the 5' domain of the third nucleic acid and linked to a fluorescent molecule.

44. A product authentication system comprising:
   (a) a first nucleic comprising a 5' domain and a 3' domain;
   (b) a second nucleic acid comprising (i) a 5' domain and (ii) a 3' domain complementary to the 5' domain of the first nucleic acid;
   (c) a third nucleic acid comprising (i) a 5' domain and (ii) a 3' domain complementary to the 5' domain of the second nucleic acid
   (d) a fourth nucleic acid comprising (i) a 5' domain complementary to the 3' domain of the first nucleic acid and linked to a quencher molecule and (ii) a 3' domain complementary to the 5' domain of the third nucleic acid; and
   (e) a fifth nucleic acid comprising a 3' domain complementary to the 5' domain of the fourth nucleic acid and linked to a fluorescent molecule.

EXAMPLES

Example 1

FIG. 3A shows a schematic for combining several PER hairpins and other reagents for automatic stepwise growth of a primer sequence. FIG. 3B shows a reaction diagram for five elongation steps, patterned by hairpins A, B, C, D, and E. FIG. 2C shows a denaturing gel demonstrating differential extension with different subsets of the hairpin species present. Reactions were incubated for 4 hours at 37° C., with primer concentrations at 100 nM, hairpins at 10 nM, and dATP, dTTP, and dCTP at 10 µM each.

Example 2

Figure 5D:
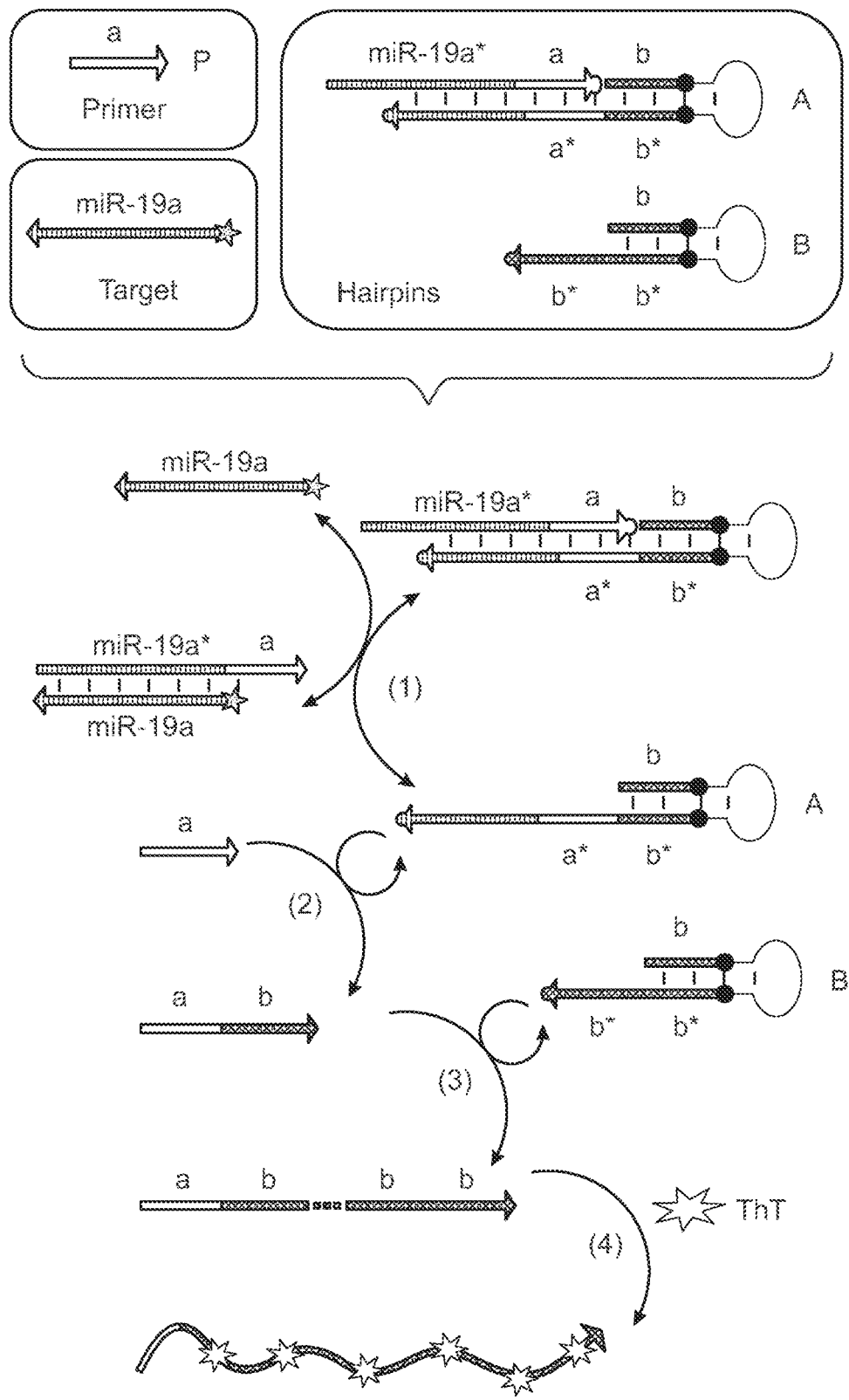

FIG. 5A shows a schematic for implementing a synthetic telomerase with a single PER hairpin. FIG. 5B shows a PAGE denaturing gel showing telomerization under different hairpin concentrations. Primers were incubated with the given hairpin concentrations for 4 hours at 37° C. FIG. 5C shows a schematic for label-free biosensor, where a miRNA target activates the synthesis of fluorescent telomere strands. FIG. 5D shows system components and reaction diagram for the biosensor. A gated hairpin ('A') and telomerase hairpin ('B') were designed to react to the detection of a miRNA signal and concatenate repeats of the human telomeric sequence TTAGGG, into which Thioflavin (ThT) intercalates and becomes fluorescent. FIG. 5E shows a native PAGE gel showing conditional telomerization in the presence of 10 nM miRNA signal. Target detection could be visualized directly with a blue light transilluminator through the amber filter unit (vis), and the fluorescence of the reactions was also visualized on a Typhoon scanner under the FAM channel (FAM).

Example 3

Figure 6C:
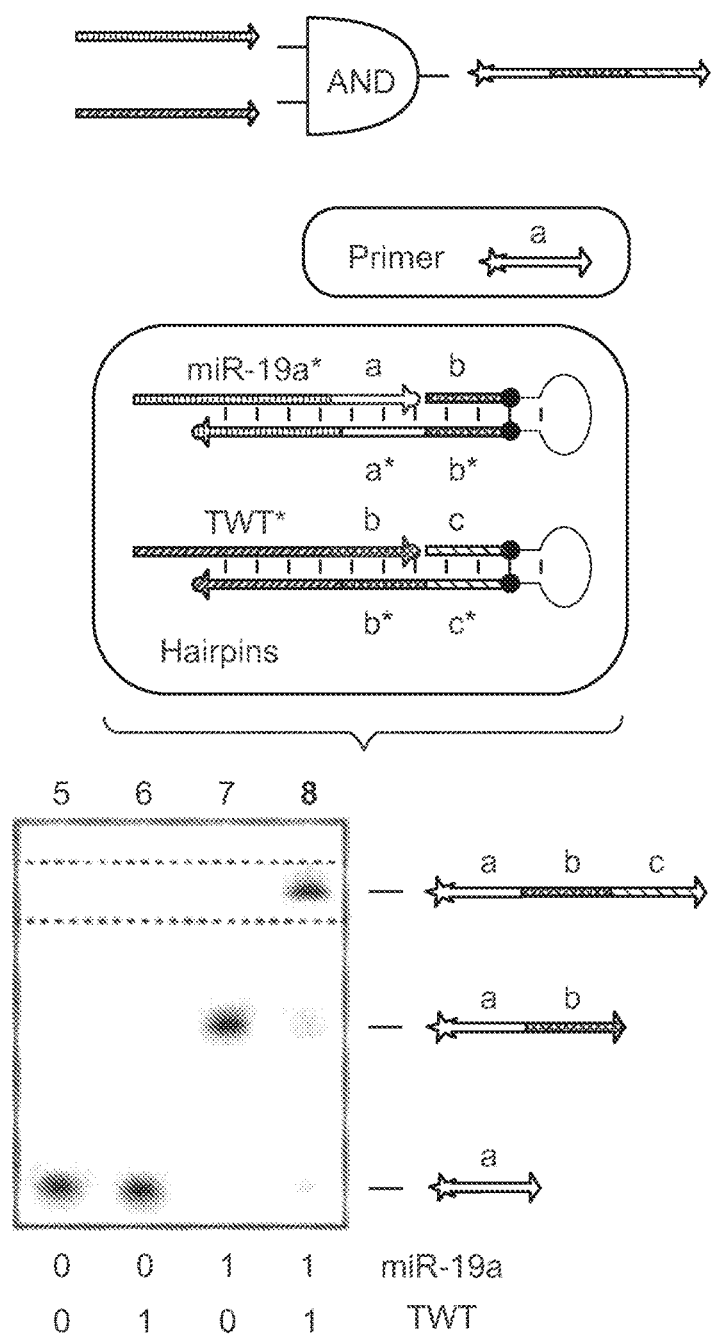
Figure 6D:
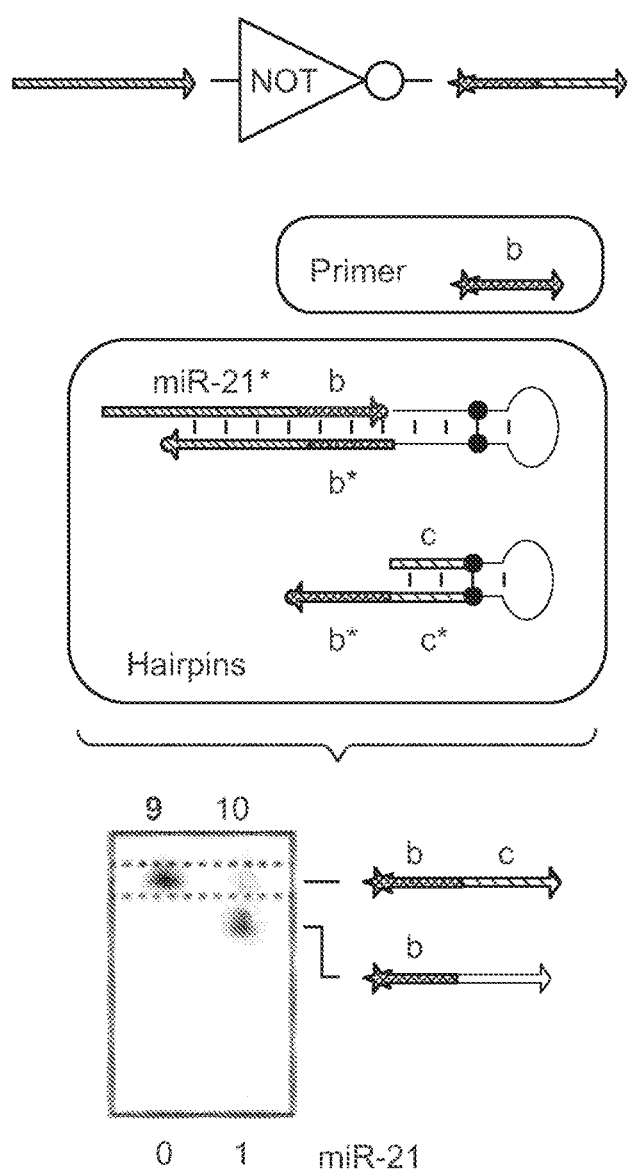
Figure 6E:
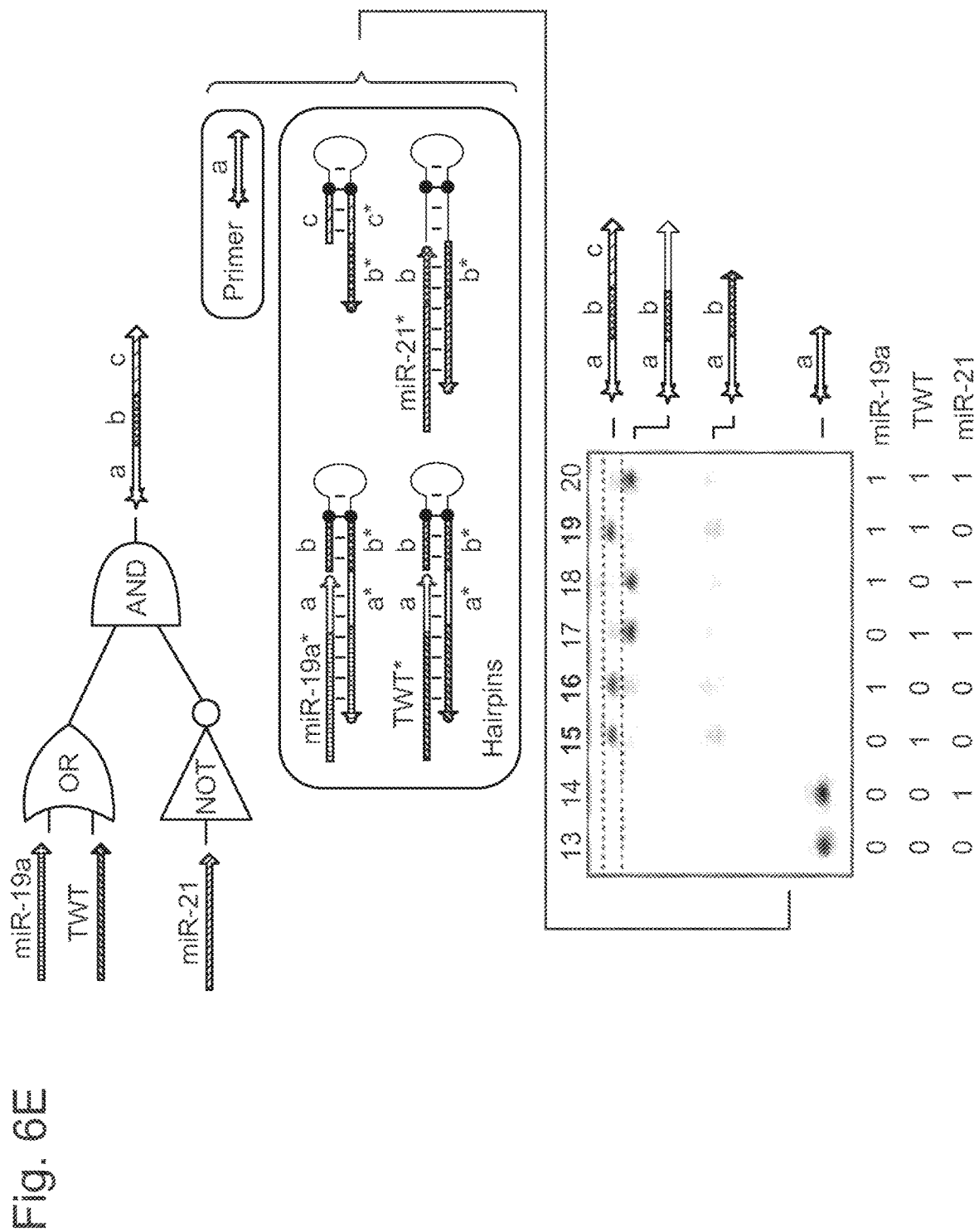

FIG. 6A shows an operational schematic for evaluating logic expressions with RNA inputs. FIG. 6B shows miR-19a OR TWT gate reaction components and a PAGE denaturing gel depicting transcript production in response to the different RNA inputs. True outputs are read by looking for transcripts of a particular length, indicated by the dotted lines. Reaction setup and PAGE denaturing gel results are also shown for miR-19a AND TWT (FIG. 6C), NOT miR-21 (FIG. 6D), and (miR-19a OR TWT) AND (NOT miR-21) (FIG. 6E).

Example 4

In this study, two different toehold switches '2_4' and '2_10' followed by GFP encoded on a plasmid were tested. Several DNA triggers as well as RNA triggers encoded on plasmids were also tested. A GFP gene encoded on the plasmid without the switch construct was used as a positive control. Very little crosstalk was observed with the non-cognate switch, trigger pairs ('Sw2_4+Trig2_10.35' and 'Sw2_10+Trig2_4.35') (FIG. 7).

The relevant sequences on plasmids follow. For the switches, the sequences start with GCGC and a T7 promoter and end with a linker sequence. For the triggers, the sequences start with GCGC and a T7 promoter and end with parts of a T7 terminator.

```
Sw 2_4
                                           (SEQ ID NO: 1)
GCGCTAATACGACTCACTATAGGGAGTAAGATAATGAAGGTAGGTATGT
TAAACTTTAGAACAGAGGAGATAAAGATGAACATACCTACGAACCTGGC
GGCAGCGCAA

Sw 2_10
                                           (SEQ ID NO: 2)
GCGCTAATACGACTCACTATAGGGATTGAATATGATAGAAGTTTAGTAG
TAGACAATAGAACAGAGGAGATATTGATGACTACTAAACTAAACCTGGC
GGCAGCGCAA

Trig2_4
                                           (SEQ ID NO: 3)
GCGCTAATACGACTCACTATAGGGCTCGATCACTAATCTGATCGAGACG
AACATACCTACCTTCATTATCTTACTTGTTAGCATAACCCCTTGGGGC Trig2_10
                                           (SEQ ID NO: 4)
GCGCTAATACGACTCACTATAGGGATACACATAGAATCATGTGTATAAC
ACTACTAAACTTCTATCATATTCAATCACTAGCATAACCCCTTGGGGC
```

DNA Trigger Sequences:

```
2_04.32
                                           (SEQ ID NO: 5)
ACGAACATACCTACCTTCATTATCTTACTTGT

2_04.35
                                           (SEQ ID NO: 6)
ACGAACATACCTACCTTCATTATCTTACTCCCCAC

2_04.38
                                           (SEQ ID NO: 7)
ACATTTAACATACCTACCTTCATTATCTTACTCCCCAC

2_10.32
```

```
                                            (SEQ ID NO: 8)
AACACTACTAAACTTCTATCATATTCAATCAC

2_10.35
                                            (SEQ ID NO: 9)
AACACTACTAAACTTCTATCATATTCAATCCCCAC

2_10.38
                                            (SEQ ID NO: 10)
AACTCTACTACTAAACTTCTATCATATTCAATCCCCAC
```

PURExpress® half volume reaction:
 5 µL Solution A
 3.75 µL Solution B (add *to* A)
 Plasmid DNA
 Trigger (1.25 µL of 30 µL stock)
 H$_2$O to 12.5 µL
GFP fluorescence was measured on a BioTek plate reader after 4 hours, incubation at 37° C.
Components in the reactions (Switch, Trigger):
2_4, 2_10.35
2_4, 2_4.32
2_4, 2_4.35
2_4, 2_4.38
2_4, 2_4 RNA trigger
2_10, 2_4.35
2_10, 2_10.32
2_10, 2_10.35
2_10, 2_10.38
2_10, 2_10 RNA trigger
GFP positive control

Example 5

This study tested the extension of primers by a PER reaction to generate DNA trigger sequence for a toehold switch. A 3-step extension reaction or 1-step extension reaction works well (FIG. 8).
DNA Sequences for the PER Hairpins:

```
h1.1.2_04
                                            (SEQ ID NO: 11)
ACCTACCTTCGGGCCTTTTGGCCCGAAGGTAGGT ATGTTCGT/
3InvdT/ h2.1.2_04
                                            (SEQ ID NO: 12)
ATTATCTTGGGCCTTTTGGCCCAAGATAATGAAGGTAGG/3InvdT/ h3.1.2_04
                                            (SEQ ID NO: 13)
ACTCCCCACGGGCCTTTTGGCCCGTGGGGAGT AAGATAATGA/
3InvdT/ h1.2.2_04
                                            (SEQ ID NO: 14)
ACCTACCTTCGGGCCTTTTGGCCCGAAGGTAGGT ATGTTCG/
3InvdT/ h2.2.2_04
                                            (SEQ ID NO: 15)
ATTATCTTGGGCCTTTTGGCCCAAGATAATGAAGGTAG/3InvdT/ h3.2.2_04
                                            (SEQ ID NO: 16)
ACTCCCCACGGGCCTTTTGGCCCGTGGGAGTAAGATAATG/3InvdT/ hfull.2_04
                                            (SEQ ID NO: 17)
ACCTACCTTCATTATCTTACTCCCCACGGGCCTTTTGGCC
CGTGGGGAGTAAGATAATGAAGGTAGGT ATGTTCGT/3InvdT/
```

PER (50 µL reactions):
 12.5 µL BST LF
 12.5 µL p.2_04 to 1 µM final concentration
 12.5 µL Hairpins to 100 nM final concentration
 12.5 µL dNTPs (A, T, C only) to 100 µM final concentration
Control: h2.*.2_04+h3.*.2_04
3-step: h1.*.2_04+h2.*.2_04+h3.*.2_04
*=11, 21
Reactions:
A) No hairpins
B) Control (no h.1.*.2_04 hairpin) (4 lanes)
C) 3-step (8 lanes)
D) 1-step (h.full.2_04)

Example 6

In this study, the resulting reaction mix of a PER reaction was added to a PURExpress® system with toehold switches. The negative control has no trigger. The positive control has 100 nM DNA trigger (ordered from Integrated DNA Technologies). The numbers located above the bars in the graph of FIG. 9 are the estimated concentration of DNA products based on gel analysis. ON/OFF ratio: ~10×.

Example 7

Figure 12D:
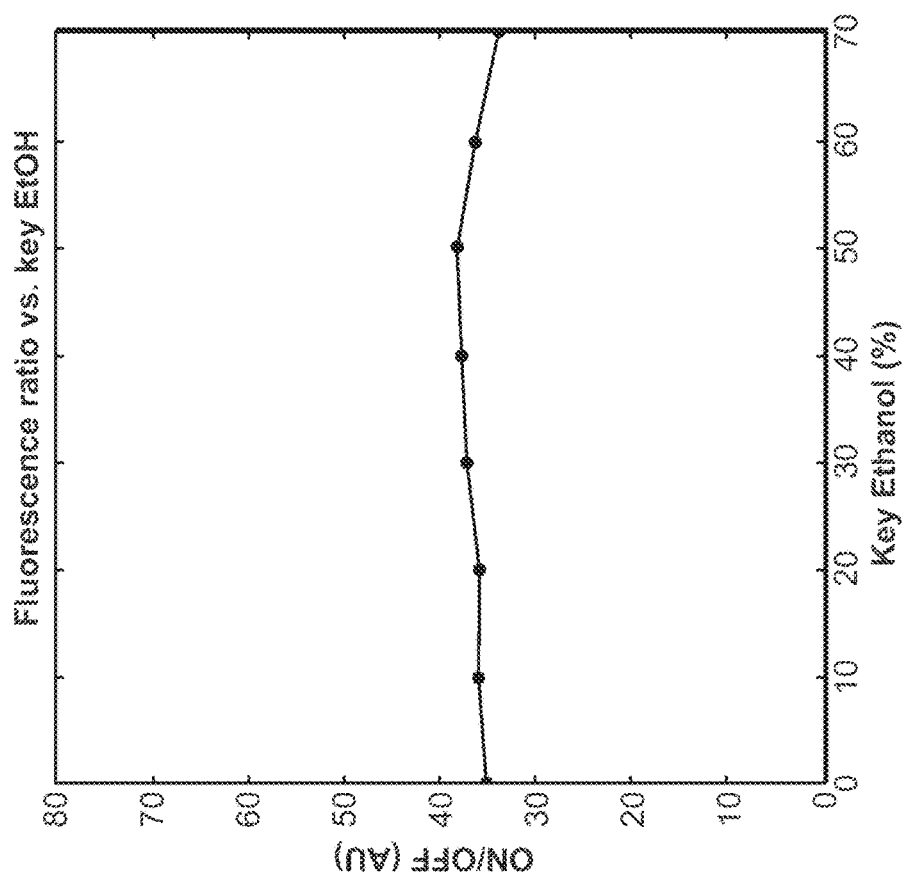
Figure 13:
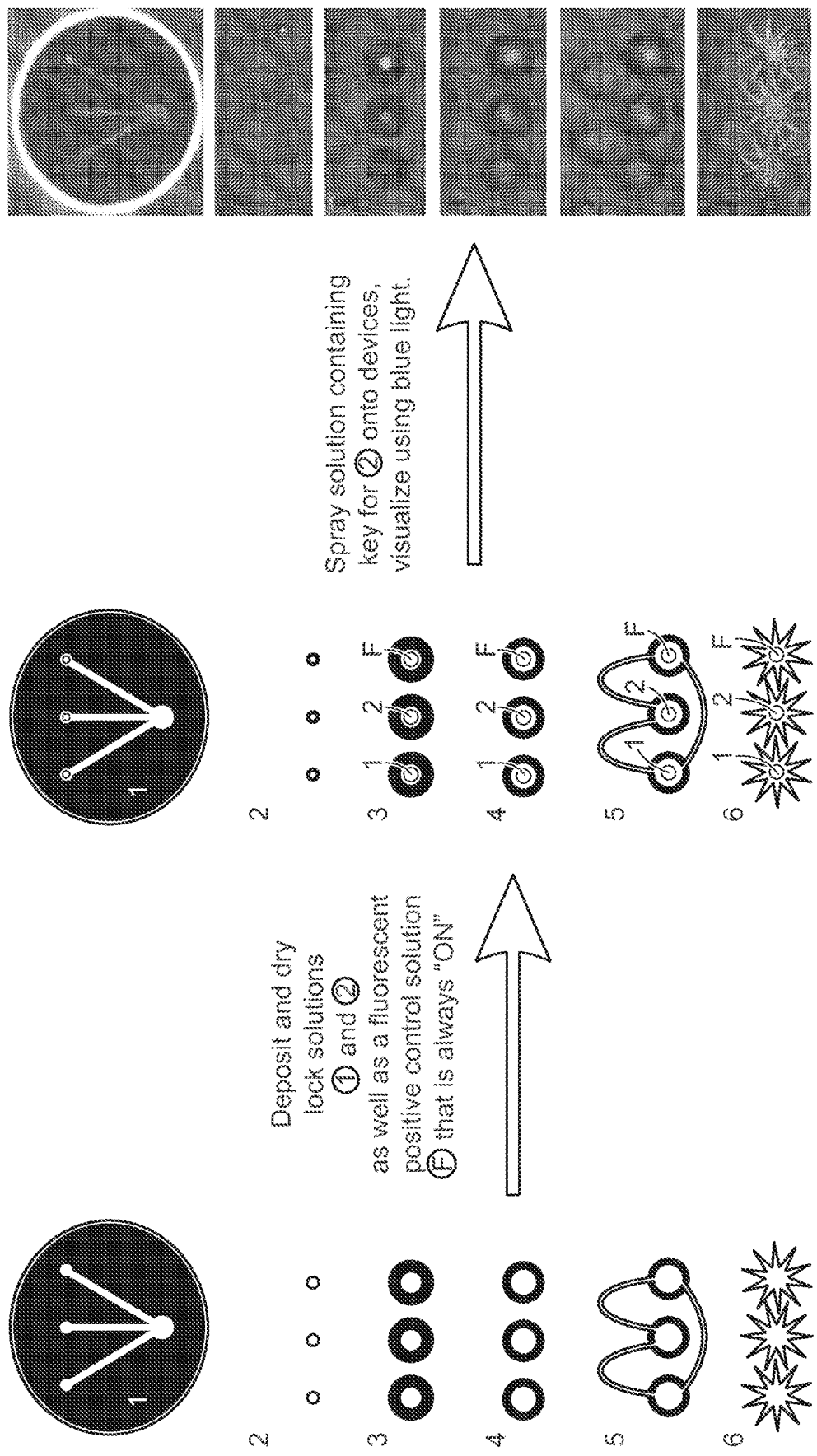
FIG. 13 presents a schematic of one of the experiments described in Example 7, demonstrating that key '2' specifically unlocks lock '2.'

In this example, the performance of six difference graphic designs were tested using the two key/lock pairs depicted in FIG. 12B. A schematic depicting the method as well as images of the results are shown in FIG. 13. Six different graphic designs were first printed onto filter paper using a wax printer. The deposited wax was then heated at 150° C. for 2-3 minutes to melt the wax through the filter paper to create discrete hydrophobic barriers. Each of lock '1' (12 µM), lock '2' (12 µM), and a free fluorescent positive control strand 'F' (5 µM) was deposited within a discrete hydrophobic barrier of each of graphic designs. A solution containing only the key for lock '2' (10 µM: 200 µl of the key in 2 ml total volume of solution) was sprayed 2-3 times onto each of the six designs, covering each discrete hydrophobic barrier filled with either a lock or a control fluorescent strand. Visualization through an amber filter unit under a blue light transilluminator showed fluorescent only within hydrophobic barriers containing lock '2' and the control.

Figure 14A:
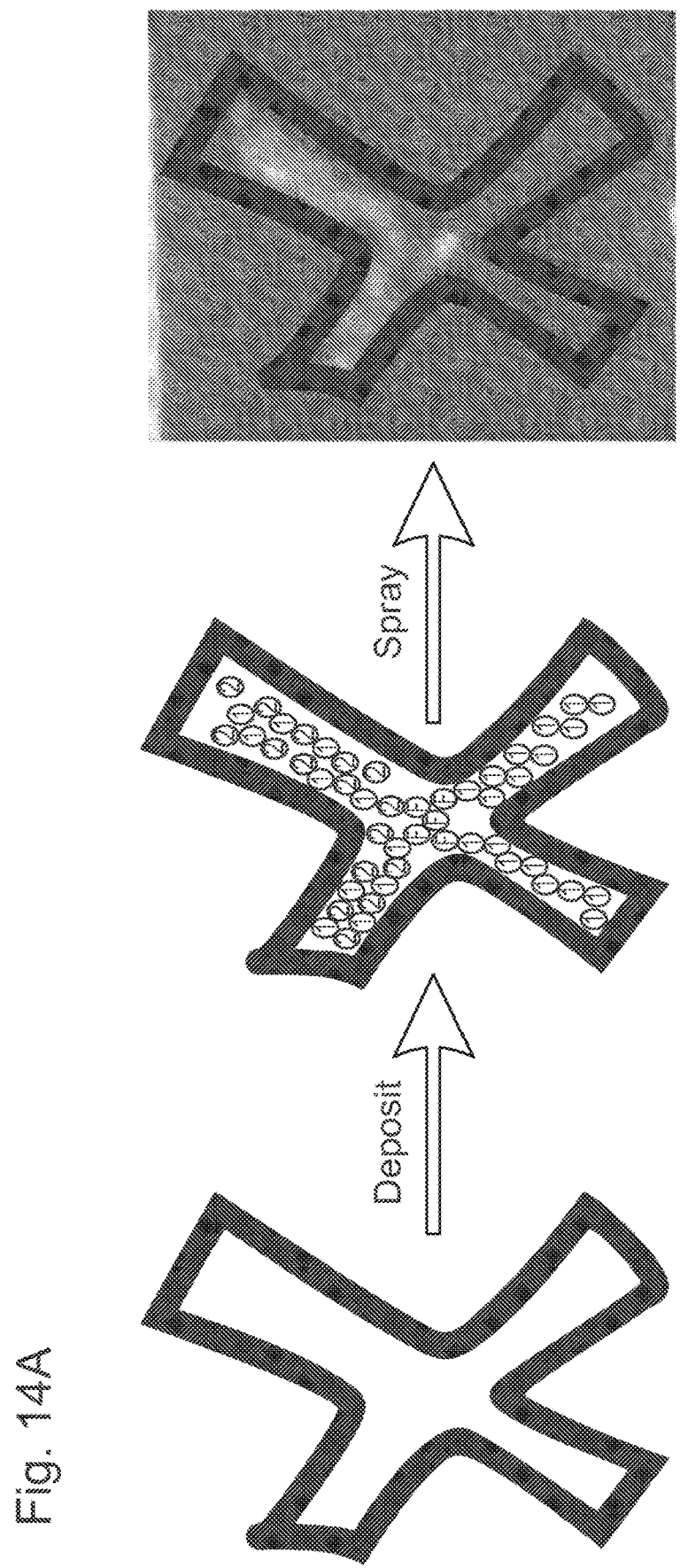
Figure 14B:
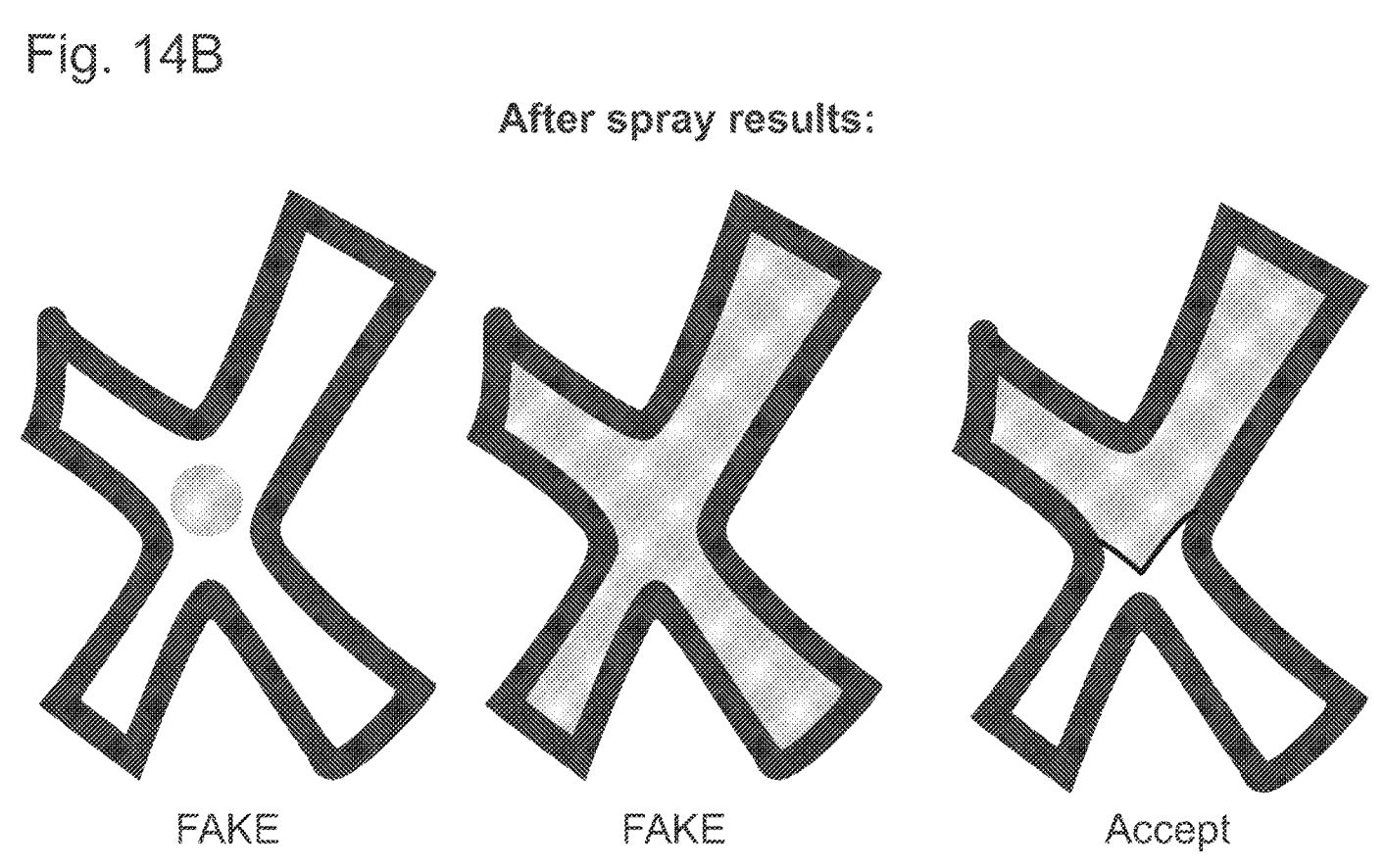

The key/lock pairs shown in FIG. 12B were also applied to another graphic design, depicted in FIG. 14A. The lock '1' and lock '2' solutions were deposited in a pre-determined manner (in discrete regions forming a check-mark pattern) within the graphic 'X' design. The key '2' solution, when applied to the graphic 'X' design, unlocked only the lock '2' regions, depicted by the fluorescent check-mark shape.

Example 8

This example describes an imager used to read a paper-based DNA key assay. Blue light excites fluorescein (FAM) or similar fluorophores safely and effectively. As shown in FIG. 16, short-pass optical filters can modify blue incident light and long-pass filters (such as the McMaster amber acrylic transmissivity) can pass FAM emissions reasonably well, for the optimal detection of FAM. The handheld imager shown in FIG. 17 operates with the optical path described above, utilizing blue LEDs and short- and long-pass filters in a dark box.

Example 9

This example describes a test of the lock/key mechanism in alcohol-containing key solutions. An experiment was designed to evaluate lock and key pairs in key solutions containing up to 70% ethanol (EtOH).

First, the fluorophore/quencher pair 1 depicted in FIG. 12B was annealed by mixing the fluorophore-containing strand (500 nM) with excess quencher (666.7 nM) in a 1×TE+10 mM $MgCl_2$ solution. This solution was then heated to 80° C. for two minutes before being held at room temperature for 20 minutes. Subsequently, 10 µL of the solution was split across each of 24 wells of a 384 plate.

Next, at room temperature, the wells were mixed with 10 µL of one of the 24 solutions containing either no oligo or one of the two key trigger strands depicted in FIG. 12B and an ethanol percentage ranging from 0% (none) to 70%, diluted from an 100% ethanol solution. Twenty-four different conditions were tested: no key, 0% ethanol; no key, 10% ethanol; no key, 20% ethanol; no key, 30% ethanol; no key, 40% ethanol; no key, 50% ethanol; no key, 60% ethanol; no key, 70% ethanol; wrong key (key strand for fluorophore/quencher pair 2), 0% ethanol; wrong key (key strand for fluorophore/quencher pair 2), 10% ethanol; wrong key (key strand for fluorophore/quencher pair 2), 20% ethanol; wrong key (key strand for fluorophore/quencher pair 2), 30% ethanol; wrong key (key strand for fluorophore/quencher pair 2), 40% ethanol; wrong key (key strand for fluorophore/quencher pair 2), 50% ethanol; wrong key (key strand for fluorophore/quencher pair 2), 60% ethanol; wrong key (key strand for fluorophore/quencher pair 2), 70% ethanol; correct key (key strand for fluorophore/quencher pair 1), 0% ethanol; correct key (key strand for fluorophore/quencher pair 1), 10% ethanol; correct key (key strand for fluorophore/quencher pair 1), 20% ethanol; correct key (key strand for fluorophore/quencher pair 1), 30% ethanol; correct key (key strand for fluorophore/quencher pair 1), 40% ethanol; correct key (key strand for fluorophore/quencher pair 1), 50% ethanol; correct key (key strand for fluorophore/quencher pair 1), 60% ethanol; and correct key (key strand for fluorophore/quencher pair 1), 70% ethanol.

Figure 12C:
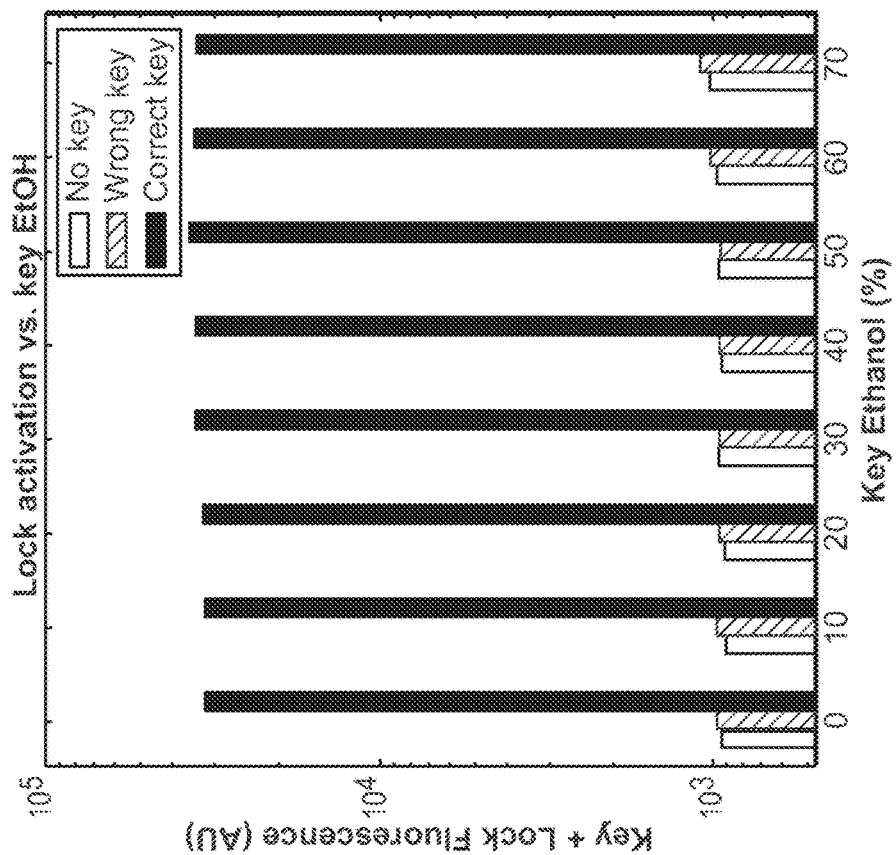

The fluorescence values of these 24 different key/lock reactions were then measured on a plate reader at 33.8° C. Results are shown in FIGS. 12C-12D. FIG. 12C shows the raw fluorescence values for each of the 24 wells plotted on a log scale. In all cases, the fluorescence for the correct key and lock pair is significantly higher than that of the other two conditions with the same ethanol concentration ("No key" and "Wrong key"). FIG. 12D shows the ON/OFF ratios for each of the 8 ethanol conditions tested, calculated by dividing the fluorescence of the correct key and lock pair solution by the fluorescence of the solution with no key. In all cases, the ON/OFF ratio comfortably exceeds 30× and stays roughly constant throughout. These data confirm the hybridization and strand displacement reactions relied on by the design depicted in FIG. 12B can operate in the presence of alcohol.

Example 10

This example describes several mechanisms of fixed amplification. As shown in FIG. 18A, the lock or key strand comprises more than one fluorophore and quencher, resulting in two or three times the fluorescent signal output ("ON" state). In an alternative embodiment, shown in FIG. 18B, a single quencher prohibits fluorophore signaling from two fluorophore strands ("OFF" state; top panel). When the lock and key interact, the two fluorophore strands are removed from the quencher strand, leading to an amplified fluorescent signal (FIG. 18B, bottom panel).

Amplification may also result from hybridization chain reactions, as depicted in FIGS. 19A-19C. Each hairpin in the final product (FIG. 19C) is unique, holding at least one fluorophore and/or quencher moiety. All hairpins are present in solution, forming the lock mechanism (FIG. 19A). The entire cascade of hairpins are triggered to open in sequential order by a single key (strand 'ax' in FIG. 19B), activating a fixed number of fluorophores from the single key strand. All solutions, the hairpin/inactive state and the activated polymer state (FIG. 19C) are thermodynamic equilibriums, and therefore, the system is stabilized in storage.

Example 11

This example describes the use of unmodified key strands, which can be beneficial in systems for authenticating prescription drugs or other substances in which it would be undesirable to introduce modified DNA keys.

FIG. 20A shows an example in which each product contains a unique key strand and a test strip. The key strand may be unmodified. The test strip translates the product key into visible code. The visible code is a long and unique barcode pattern, which is then verified on the manufacturer's website for authenticity. Each test strip can only be used a single time because each test is unique, protecting against the dilution of a real product into a number of copied products.

FIG. 20B shows another example of an unmodified key application. In this instance, a product package, including the key and a test package, including the test strip and controls, are shipped separately for added security. The given key sequence is only valid for a short period of time, such as when a specific unmodified DNA strand is mixed within a liquid or solid drug formulation. The test strip has an expiration date and a range of serial numbers with which the test is compatible. Additionally, the lock strands are protected from reading by covalent modification or other means. Therefore, reading the key strands from current drug batches will only work during a very short time period, as the manufacturer changes the incorporated key strand after the expiration date.

REFERENCES, EACH OF WHICH IS INCORPORATED HEREIN

[1] Grosse, Eric, and Mayank Upadhyay. "Authentication at scale." IEEE Security & Privacy 11.1 (2013): 15-22.
[2] Corcoran, Peter, and Claudia Costache. "Biometric Technology and Smartphones: A consideration of the practicalities of a broad adoption of biometrics and the likely impacts." IEEE Consumer Electronics Magazine 5.2 (2016): 70-78.
[3] Corcoran, Peter M. "Biometrics and consumer electronics: A brave new world or the road to dystopia?" IEEE Consumer Electronics Magazine 2.2 (2013): 22-33.
[4] Fiebig, Tobias, Jan Krissler, and Ronny Hänsch. "Security impact of high resolution smartphone cameras." 8th USENIX Workshop on Offensive Technologies (WOOT 14). 2014.
[5] Green, Alexander A., et al. "Toehold switches: de-novo-designed regulators of gene expression." Cell 159.4 (2014): 925-939.
[6] Pardee, Keith, et al. "Paper-based synthetic gene networks." Cell 159.4 (2014): 940-954.
[7] Tribioli, Carla, and Thomas Lufkin. "Long-term room temperature storage of high-quality embryonic stem cell genomic DNA extracted with a simple and rapid procedure." Journal of biomolecular techniques: JBT 17.4 (2006): 249.

[8] Anchordoquy, Thomas J., et al. "Physical stabilization of DNA-based therapeutics." Drug discovery today 6.9 (2001): 463-470.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A product authentication method, comprising:
    (a) combining
        (i) a surface associated with a product with (ii) a solution comprising a first nucleic acid strand comprising a 5' domain, a 3' domain, and a 5' fluorescent molecule or a 5' quencher molecule,
    wherein the surface comprises
    a second nucleic acid strand comprising a 5' domain complementary to the 3' domain of the first strand, a 3' domain complementary to the 5' domain of the first strand, and a 3' quencher molecule or a 3' fluorescent molecule, wherein binding of the first strand to the second strand quenches fluorescent signal emitted by the 5' fluorescent molecule or the 3' fluorescent molecule and wherein the first strand and/or the second strand comprise(s) L-DNA or a molecule that terminates polymerization; and
    (b) assaying for fluorescence on the surface or in the solution.

2. A product authentication method, comprising:
    (a) combining a sample of a product with a first nucleic acid strand comprising a 5' domain, a 3' domain, and a 5' fluorescent molecule or a 5' quencher molecule,
    wherein the sample comprises
    a second nucleic acid strand comprising a 5' domain complementary to the 3' domain of the first strand, a 3' domain complementary to the 5' domain of the first strand, and a 3' quencher molecule or a 3' fluorescent molecule, wherein binding of the first strand to the second strand quenches fluorescent signal emitted by the 5' fluorescent molecule or the 3' fluorescent molecule and wherein the first strand and/or the second strand comprise(s) L-DNA or a molecule that terminates polymerization; and
    (b) assaying for fluorescence in the sample.

3. The method of claim 1, wherein the first strand comprises a 5' fluorescent molecule and the second strand comprises a 3' quencher molecule, and binding of the first strand to the second strand quenches fluorescent signal emitted by the 5' fluorescent molecule.

4. The method of claim 1, wherein the first strand comprises a 5' quencher molecule and the second strand comprises a 3' fluorescent molecule, and binding of the first strand to the second strand quenches fluorescent signal emitted by the 3' fluorescent molecule.

5. The method of claim 1, wherein the surface is a surface of a package containing the product or an identification tag accompanying the product.

6. The method of claim 1, wherein the first nucleic acid strand and the second nucleic acid strand form an identifiable pattern or shape on the surface.

7. The method of claim 2, wherein the product is a liquid product.

8. A product authentication kit, comprising:
    a first nucleic acid strand comprising a 5' domain, a 3' domain, and a 5' fluorescent molecule or a 5' quencher molecule; and
    a second nucleic acid strand comprising a 5' domain complementary to the 3' domain of the first strand, a 3' domain complementary to the 5' domain of the first strand, and a 3' quencher molecule or 3' fluorescent molecule,
    wherein binding of the second nucleic acid strand to the first nucleic acid strand quenches fluorescent signal emitted by the 5' fluorescent molecule or the 3' fluorescent molecule, and wherein the first strand and/or the second strand comprise(s) L-DNA or a molecule that terminates polymerization.

9. The kit of claim 8, wherein the first strand comprises a 5' fluorescent molecule and the second strand comprises a 3' quencher molecule, and binding of the first strand to the second strand quenches fluorescent signal emitted by the 5' fluorescent molecule.

10. The kit of claim 8, wherein the first strand comprises a 5' quencher molecule and the second strand comprises a 3' fluorescent molecule, and binding of the first strand to the second strand quenches fluorescent signal emitted by the 3' fluorescent molecule.

11. The kit of claim 8, wherein
    the first nucleic acid strand is formulated in a first solution, and the second nucleic acid strand is formulated in a second solution.

12. A product authentication method, comprising:
(a) combining
a surface associated with a product with (ii) a solution comprising a first nucleic acid strand comprising a 5' domain, a loop domain, and a 3' domain complementary to the 5' domain,
wherein the surface comprises
a second nucleic acid strand comprising a 5' end, a 5' domain, a loop domain, a 3' domain complementary to the 5' domain, and a 3' end, wherein one end comprises a fluorescent molecule and the other end comprises a quencher molecule, wherein binding of the 5' domain of the second strand to the 3' domain of the second strand quenches fluorescent signal emitted by the fluorescent molecule, and wherein the first strand and/or the second strand comprise(s) L-DNA or a molecule that terminates polymerization; and
(b) assaying for fluorescence on the surface or in the solution.

13. The method of claim 12, wherein the surface is a surface of a package containing the product or an identification tag accompanying the product.

14. The method of claim 12, wherein the first nucleic acid strand and the second nucleic acid strand form an identifiable pattern or shape on the surface.

15. A product authentication method, comprising:
(a) combining a sample of a product with a first nucleic acid strand comprising a 5' domain, a 3' domain, and a 5' fluorescent molecule,
wherein the sample comprises
a second nucleic acid strand comprising a 5' domain complementary to the 3' domain of the first strand, a 3' domain complementary to the 5' domain of the first strand, and a 3' quencher molecule, wherein binding of the first strand to the second strand quenches fluorescent signal emitted by the fluorescent molecule, and wherein the first strand and/or the second strand comprise(s) L-DNA or a molecule that terminates polymerization; and
(b) assaying for fluorescence in the sample.

16. The method of claim 7, wherein the liquid product comprises at least 5% alcohol.

17. The method of claim 15, wherein the product is a liquid product.

18. The method of claim 17, wherein the liquid product comprises at least 5% alcohol.

19. The method of claim 1, wherein the molecule that terminates polymerization is a non-DNA linker.

20. The method of claim 2, wherein the molecule that terminates polymerization is a non-DNA linker.

21. The kit of claim 8, wherein the molecule that terminates polymerization is a non-DNA linker.

22. The method of claim 12, wherein the molecule that terminates polymerization is a non-DNA linker.

23. The method of claim 15, wherein the molecule that terminates polymerization is a non-DNA linker.

* * * * *